United States Patent
Peterson et al.

(10) Patent No.: US 10,376,187 B2
(45) Date of Patent: Aug. 13, 2019

(54) SUBCUTANEOUS SENSOR INSERTER AND METHOD

(71) Applicant: Nova Biomedical Corporation, Waltham, MA (US)

(72) Inventors: Thomas H. Peterson, Wilmington, MA (US); Scott P. Cionek, Bolton, MA (US); Anthony Florindi, Norfolk, MA (US); Julian I. Hart, Brighton, MA (US)

( * ) Notice: Subject to any disclaimer, the term of this patent is extended or adjusted under 35 U.S.C. 154(b) by 451 days.

(21) Appl. No.: 14/843,694

(22) Filed: Sep. 2, 2015

(65) Prior Publication Data

US 2016/0058473 A1   Mar. 3, 2016

Related U.S. Application Data

(60) Provisional application No. 62/200,387, filed on Aug. 3, 2015, provisional application No. 62/045,096, filed on Sep. 3, 2014.

(51) Int. Cl.
*A61B 5/1473* (2006.01)
*A61M 5/158* (2006.01)
(Continued)

(52) U.S. Cl.
CPC ........ *A61B 5/14532* (2013.01); *A61B 5/0004* (2013.01); *A61B 5/1473* (2013.01);
(Continued)

(58) Field of Classification Search
CPC .............. A61B 5/14532; A61B 5/0004; A61B 5/14503; A61B 5/1473; A61B 5/6848;
(Continued)

(56) References Cited

U.S. PATENT DOCUMENTS 5,299,571 A   4/1994  Mastrotoraro
5,951,521 A   9/1999  Mastrotoraro et al.
(Continued)

FOREIGN PATENT DOCUMENTS

DE   102004025651 A1   12/2005
WO      2006083876 A2    8/2006

OTHER PUBLICATIONS

PCT International Search Report and Written Opinion for PCT/US2015/048275 dated Dec. 11, 2015.

*Primary Examiner* — Navin Natnithithadha
(74) *Attorney, Agent, or Firm* — Sarita L. Pickett

(57) ABSTRACT

An inserter assembly for continuous glucose monitoring with medication delivery capability where the assembly has a deployment button containing a needle deployment mechanism having a sharp held in a pre-release position, a housing body in which the deployment button is movably received within a top end of the housing body, the housing body having a sensor deployment assembly containing a lumen and a sensor disposed within the lumen and extending out of the lumen to a circuit board that is part of the sensor deployment assembly, the sensor deployment assembly matingly connected to the sharp where the sharp extends beyond the sensor deployment assembly and contains the sensor not fixedly attached to the sharp, and a sensor housing releasably received within a lower end of the housing body, the sharp extending into a sensor deployment assembly recess within the sensor housing and directly above a sensor opening in a bottom of the sensor housing.

9 Claims, 40 Drawing Sheets

(51) Int. Cl.
  *A61B 5/145* (2006.01)
  *A61B 5/00* (2006.01)
  *A61B 17/34* (2006.01)
  *A61B 17/00* (2006.01)

(52) U.S. Cl.
  CPC .......... *A61B 5/14503* (2013.01); *A61B 5/686* (2013.01); *A61B 5/6848* (2013.01); *A61B 5/7405* (2013.01); *A61B 5/0031* (2013.01); *A61B 17/3468* (2013.01); *A61B 2017/00367* (2013.01); *A61B 2560/045* (2013.01); *A61B 2560/063* (2013.01); *A61B 2562/04* (2013.01); *A61M 5/158* (2013.01); *A61M 2005/1585* (2013.01); *A61M 2005/1587* (2013.01)

(58) Field of Classification Search
  CPC ..... A61B 5/686; A61B 5/7405; A61B 5/0031; A61B 17/3468; A61B 2017/00367; A61B 2560/045; A61B 2560/063; A61B 2562/04
  USPC .......................................... 600/309, 345–366
  See application file for complete search history.

(56) References Cited

U.S. PATENT DOCUMENTS

| | | | |
|---|---|---|---|
| 6,175,752 B1 * | 1/2001 | Say | A61B 5/14532 128/903 |
| 7,381,184 B2 * | 6/2008 | Funderburk | A61B 5/14532 600/300 |
| 9,615,779 B2 * | 4/2017 | Pryor | A61B 5/6833 |
| 9,931,065 B2 * | 4/2018 | Pryor | A61B 5/6833 |
| 2002/0119711 A1 | 8/2002 | VanAntwerp et al. | |
| 2003/0060781 A1 | 3/2003 | Mogensen et al. | |
| 2003/0225361 A1 | 12/2003 | Sabra | |
| 2006/0142651 A1 | 6/2006 | Brister et al. | |
| 2006/0195029 A1 | 8/2006 | Shults et al. | |
| 2007/0249922 A1 | 10/2007 | Peyser et al. | |
| 2008/0027287 A1 | 1/2008 | Shah et al. | |
| 2008/0097246 A1 | 4/2008 | Stafford | |
| 2008/0208025 A1 | 8/2008 | Shults et al. | |
| 2008/0319414 A1 | 12/2008 | Yodfat et al. | |
| 2009/0054866 A1 * | 2/2009 | Teisen-Simony | A61M 5/14248 604/506 |
| 2010/0022863 A1 | 1/2010 | Mogensen et al. | |
| 2010/0137695 A1 * | 6/2010 | Yodfat | A61B 5/6849 600/345 |
| 2010/0174158 A1 | 7/2010 | Kamath et al. | |
| 2010/0217105 A1 | 8/2010 | Yodfat et al. | |
| 2012/0078072 A1 | 3/2012 | Roesicke et al. | |
| 2012/0184908 A1 | 7/2012 | Gundberg | |
| 2012/0190941 A1 * | 7/2012 | Donnay | A61B 5/15194 600/309 |
| 2012/0226122 A1 | 9/2012 | Meuniot et al. | |
| 2013/0138078 A1 * | 5/2013 | Smith | A61M 5/14248 604/506 |
| 2013/0253289 A1 | 9/2013 | Hadvary et al. | |
| 2013/0267811 A1 * | 10/2013 | Pryor | A61B 5/6833 600/365 |
| 2013/0267812 A1 * | 10/2013 | Pryor | A61B 5/6833 600/365 |
| 2013/0267813 A1 * | 10/2013 | Pryor | A61B 5/6833 600/365 |
| 2014/0187876 A1 | 7/2014 | Ohkoshi | |

\* cited by examiner

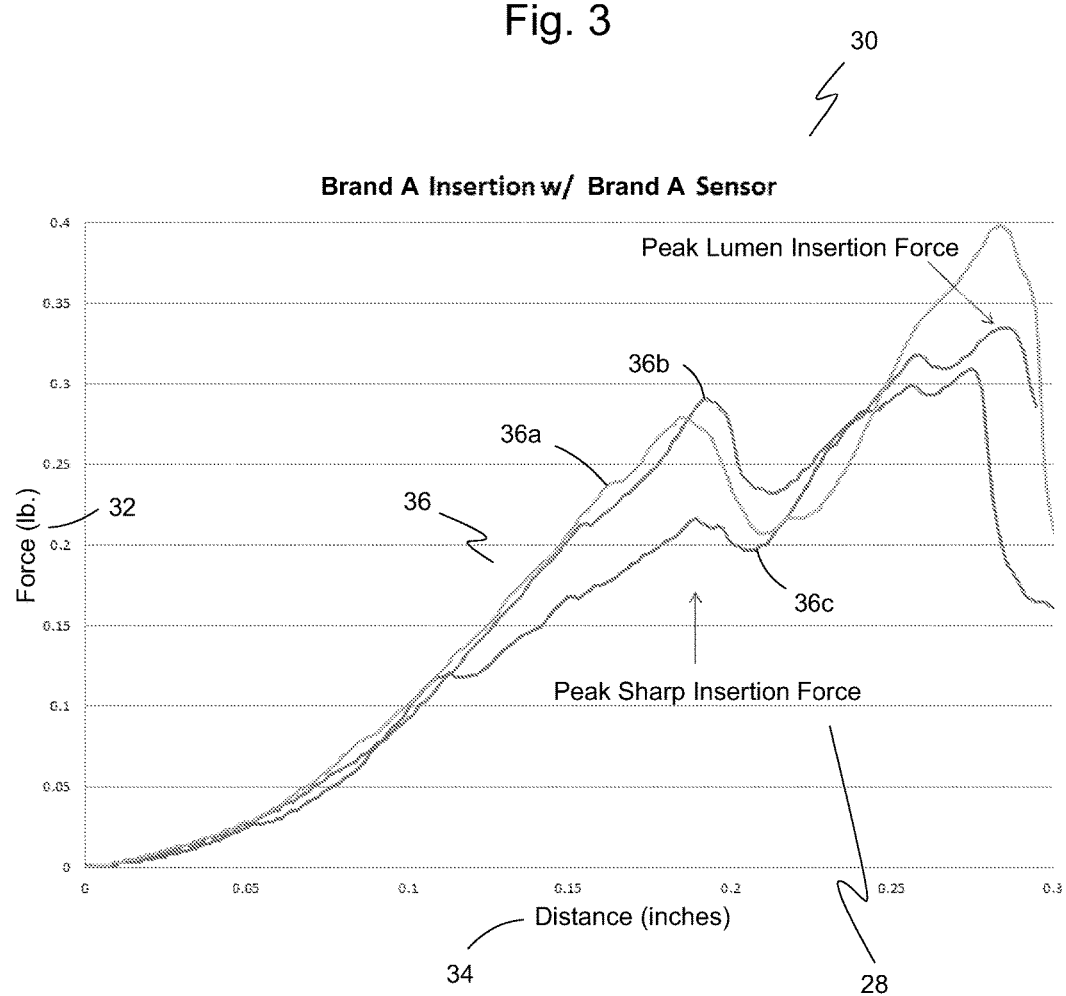

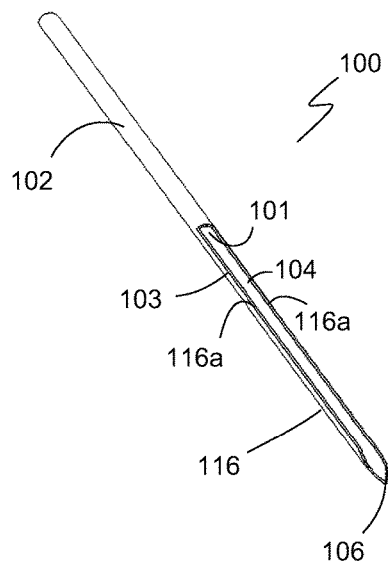
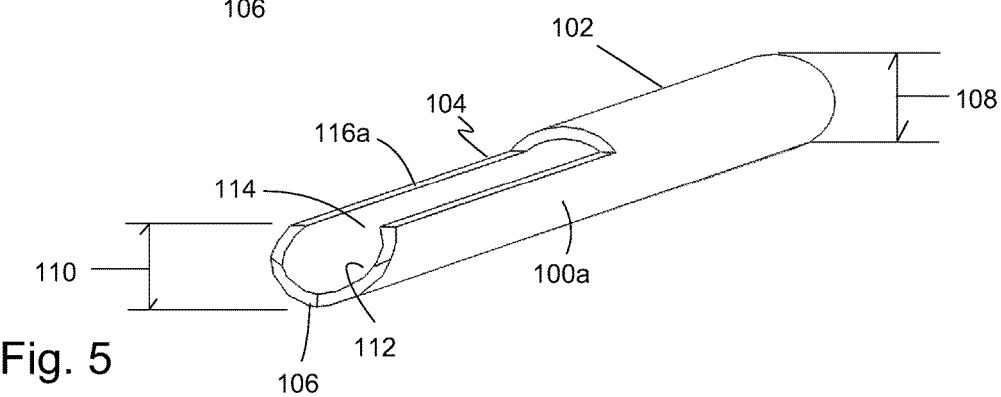
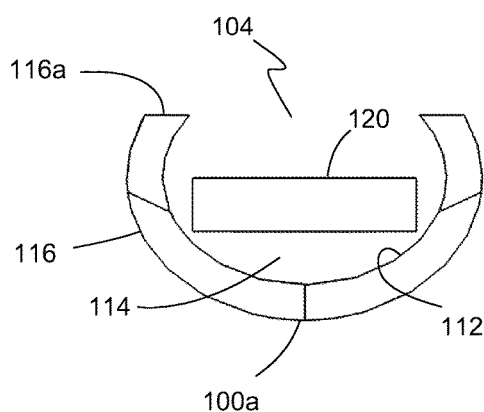

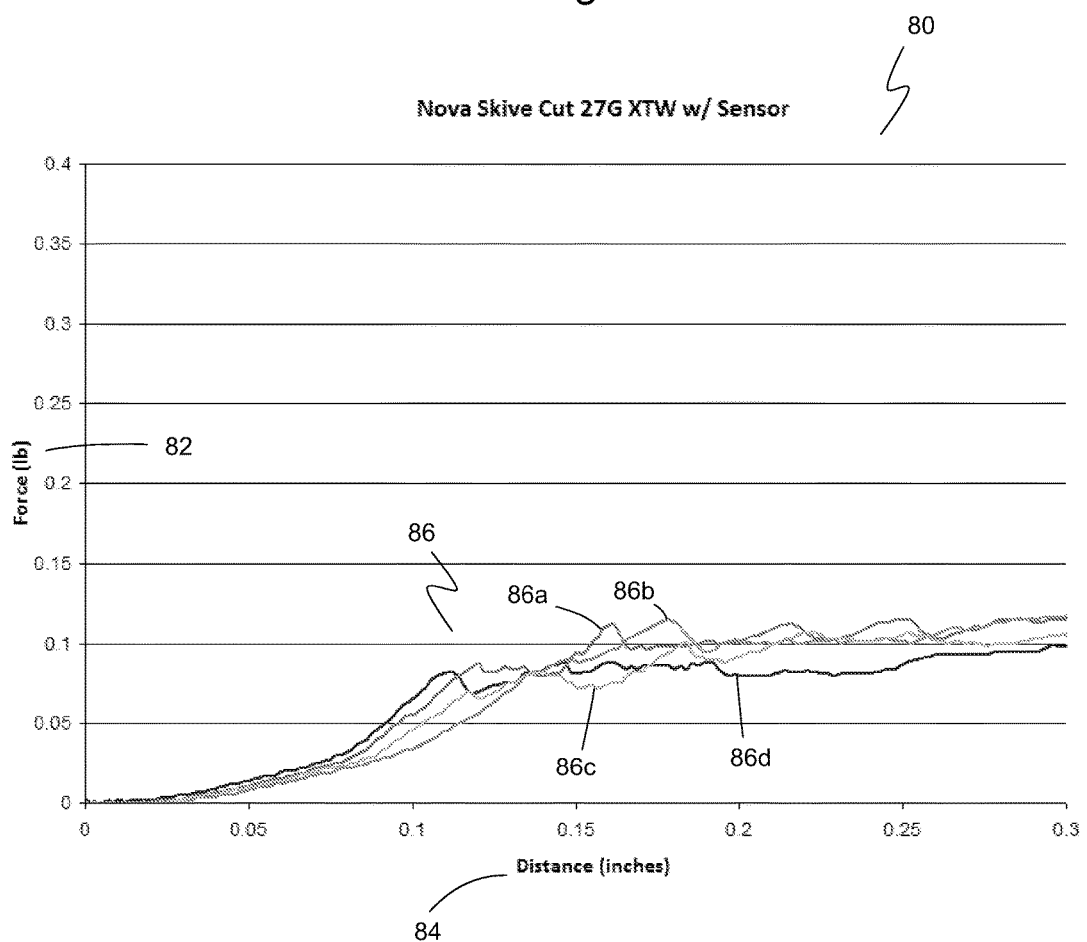

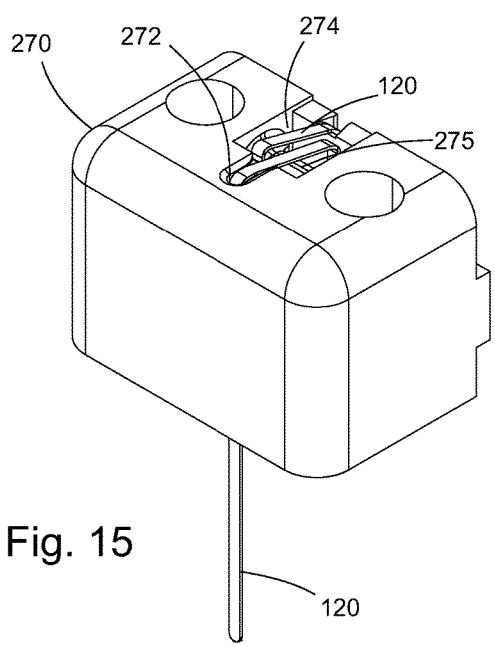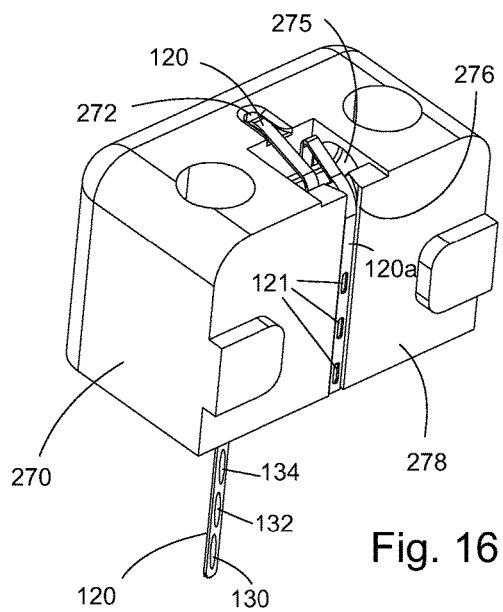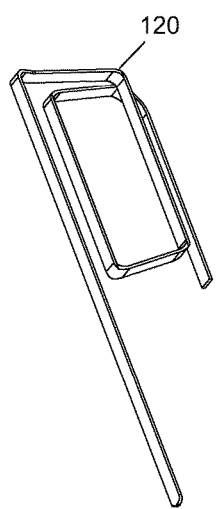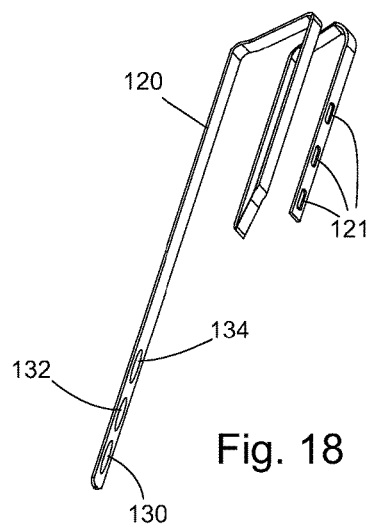
Fig. 15
Fig. 16
Fig. 17
Fig. 18

Fig. 21
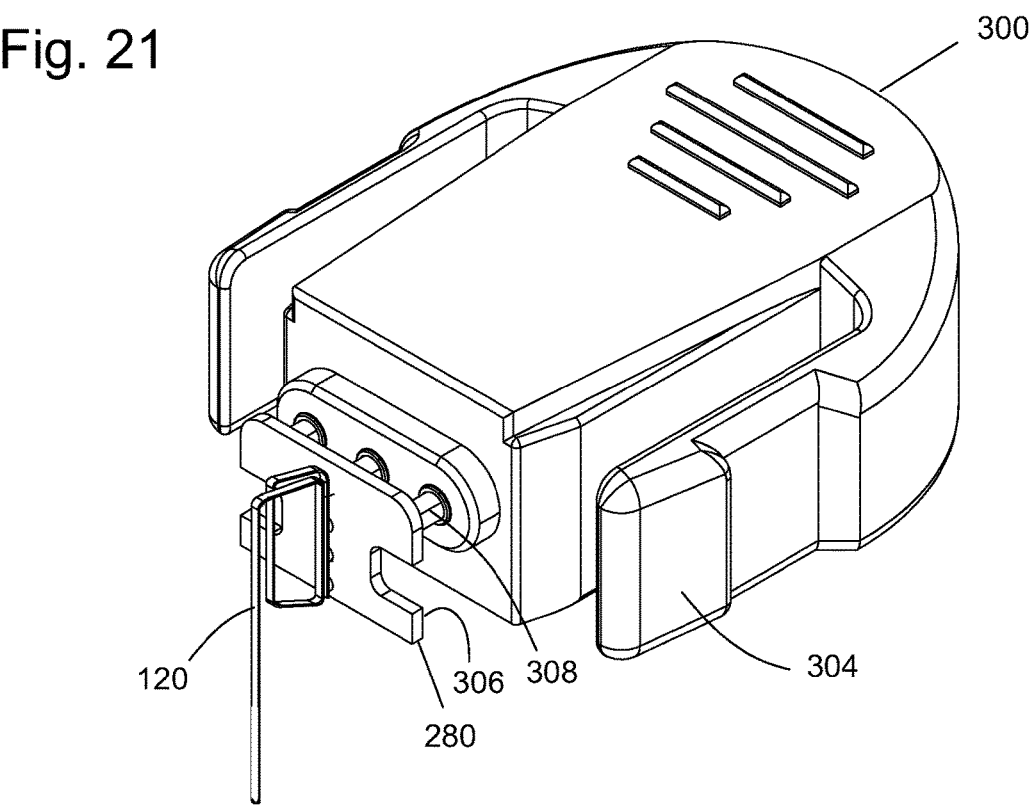
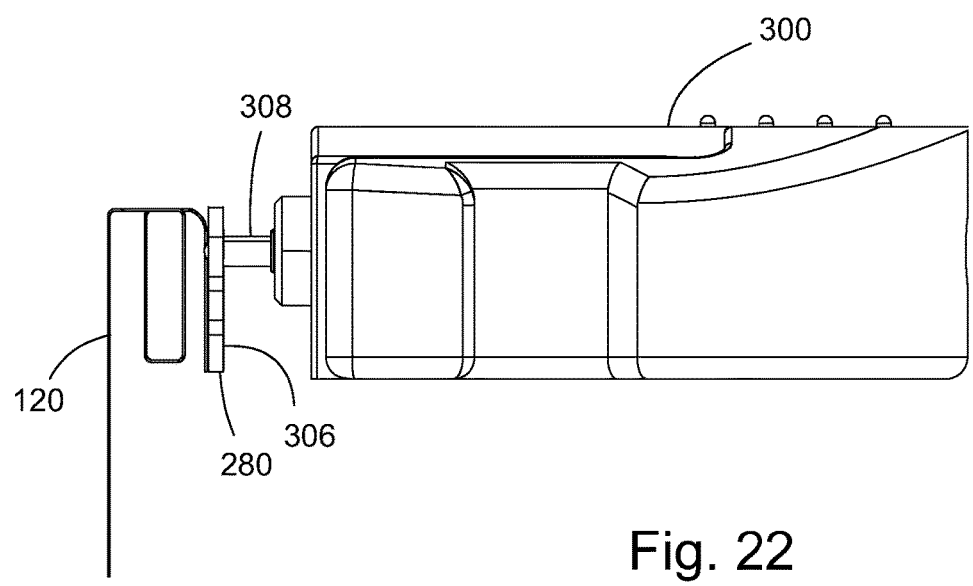
Fig. 22

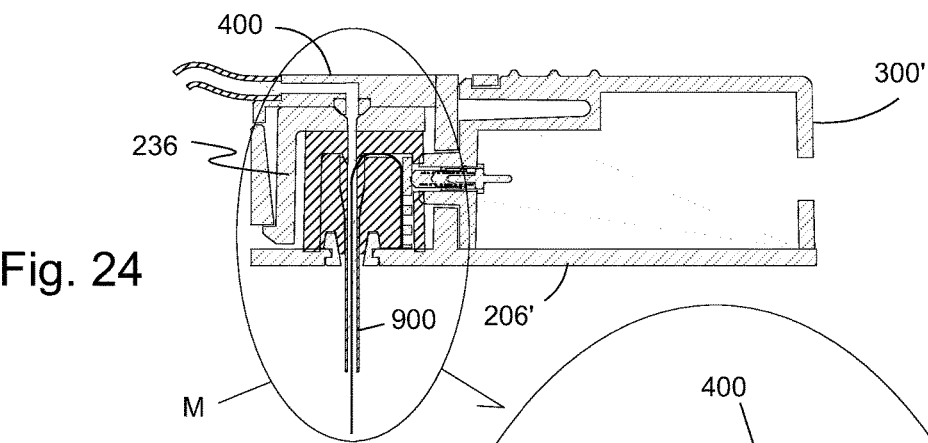
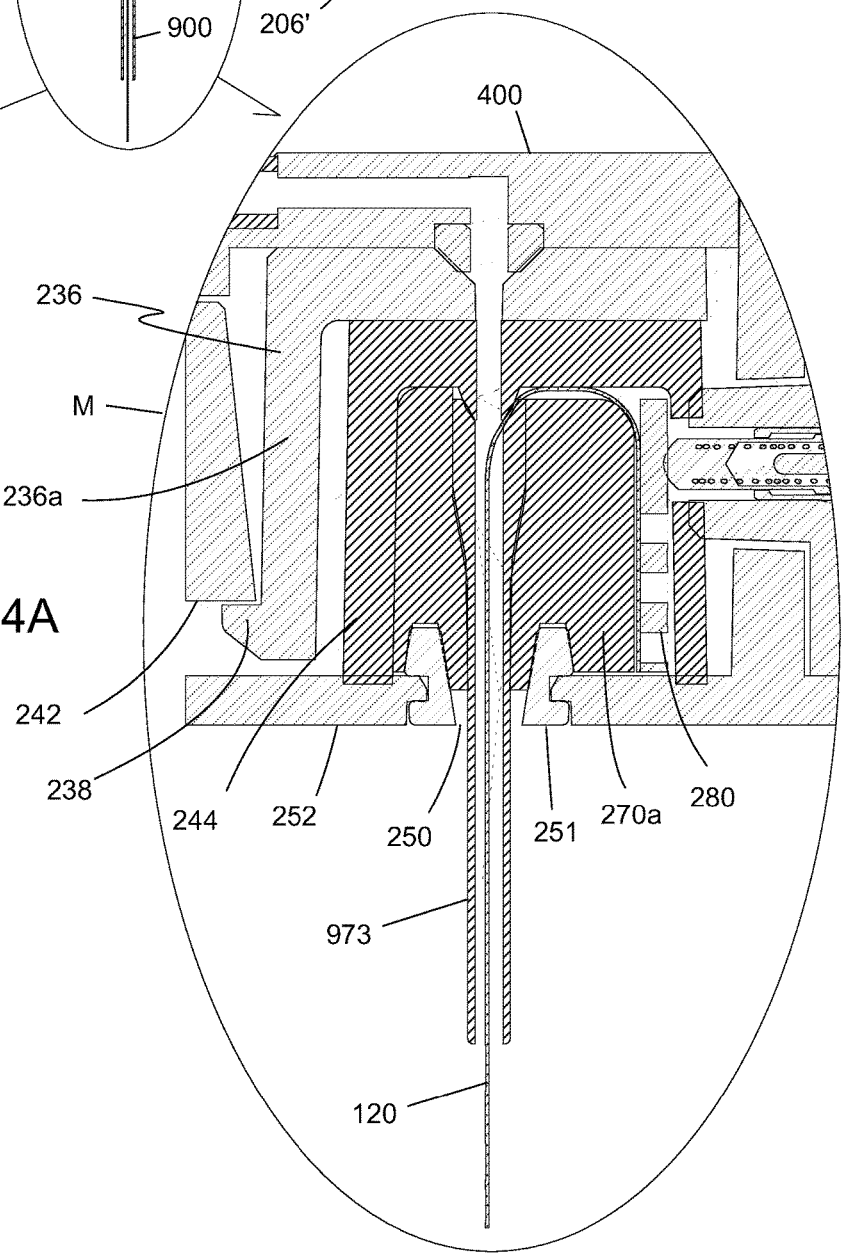

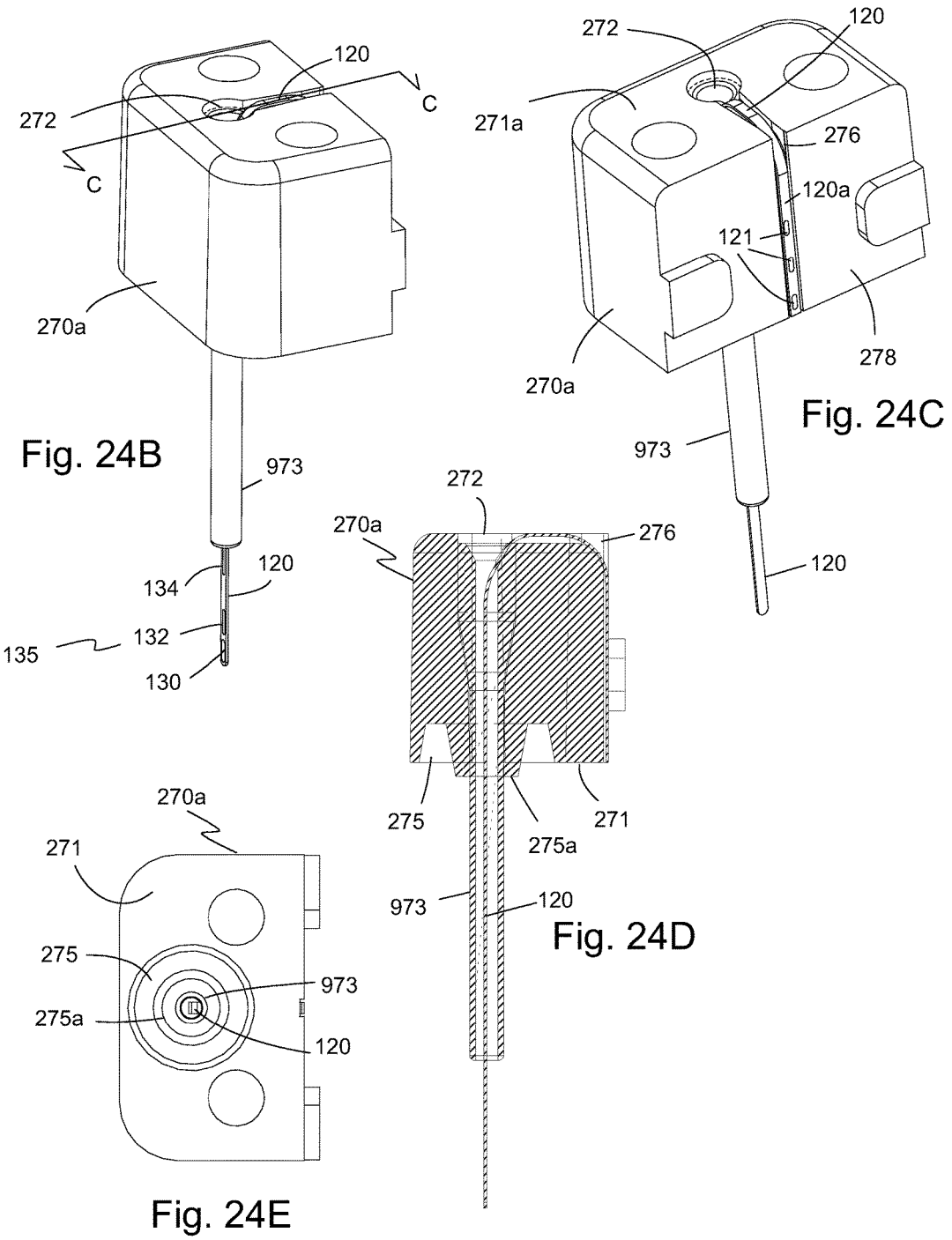

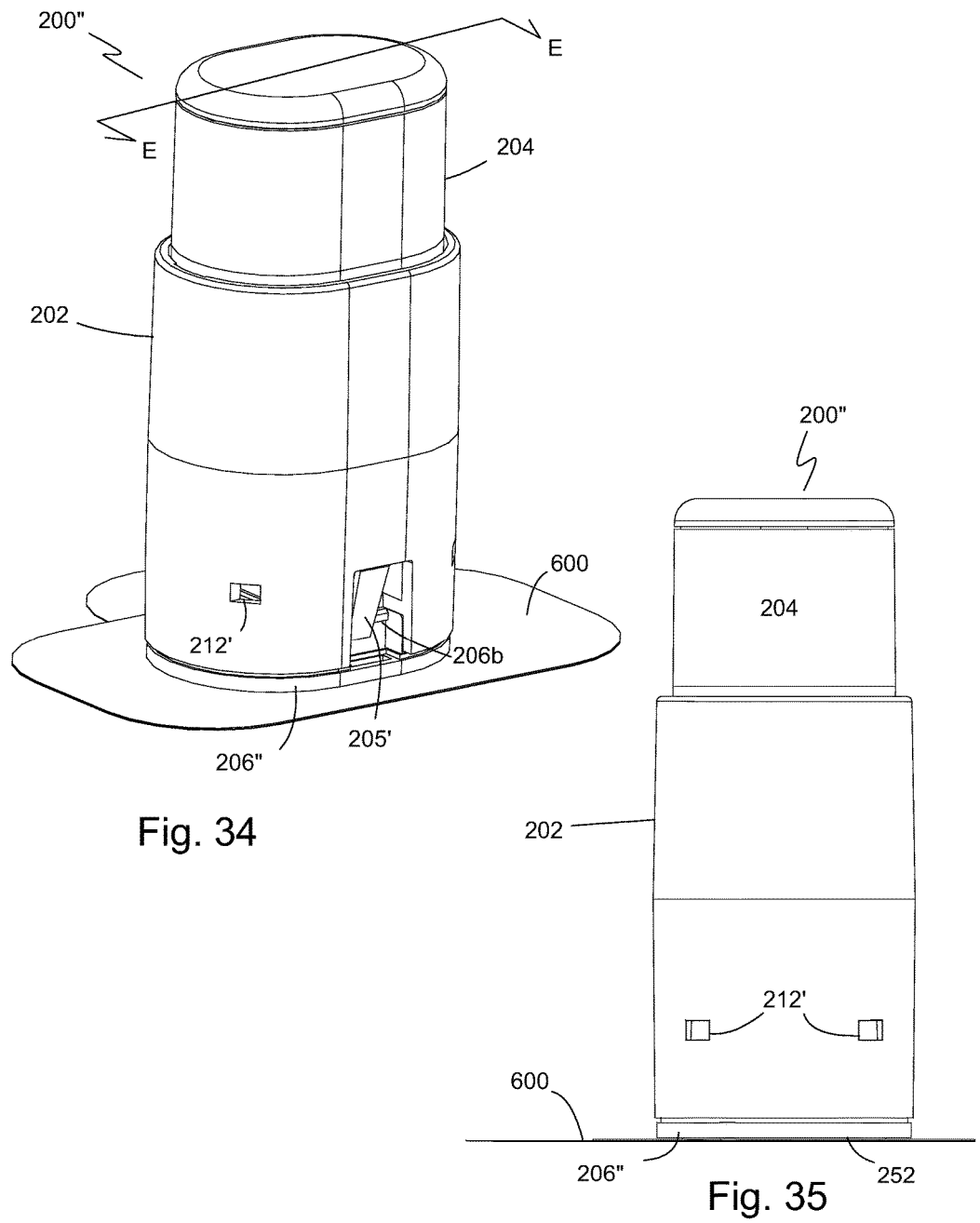

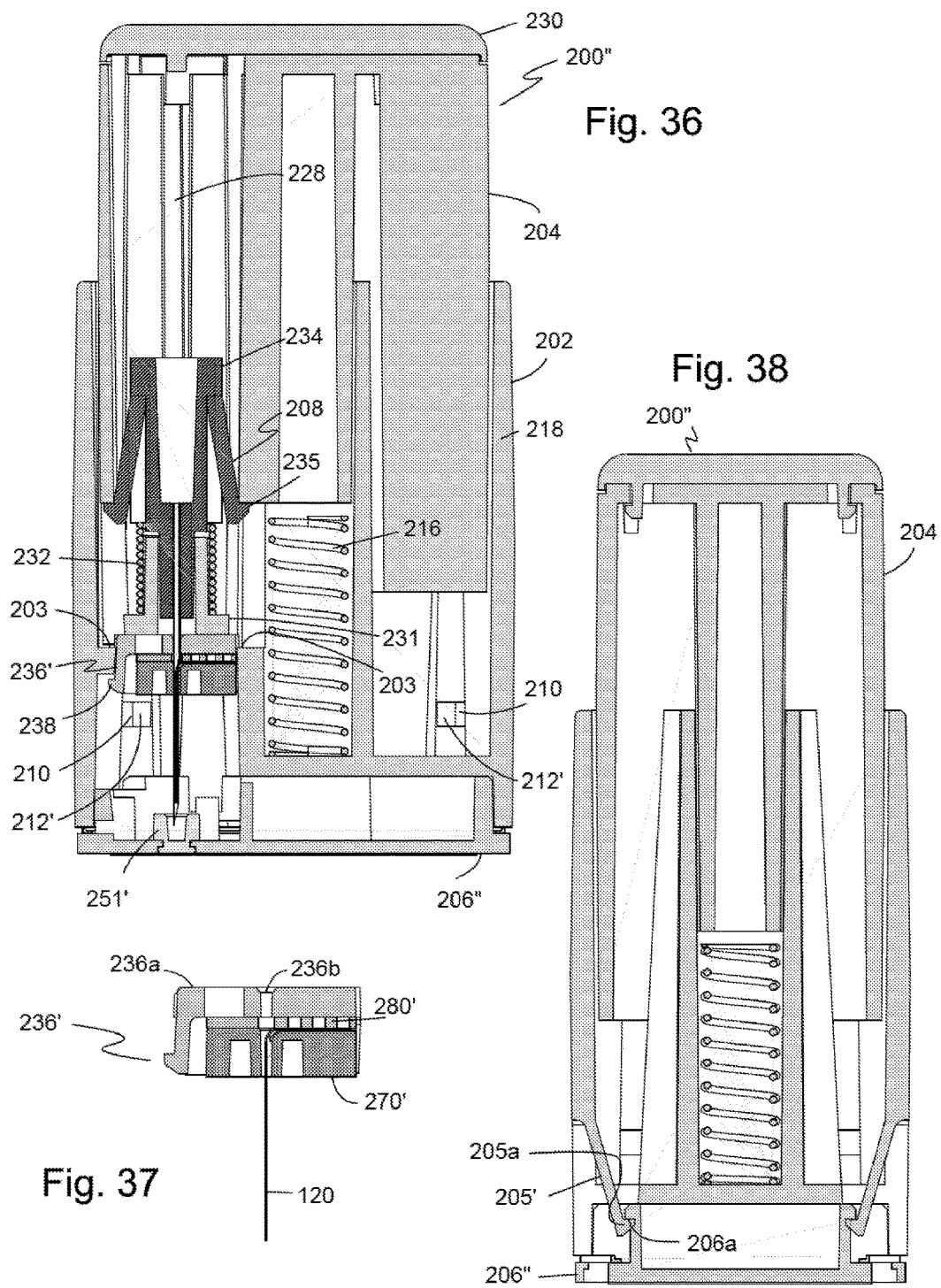

Fig. 46
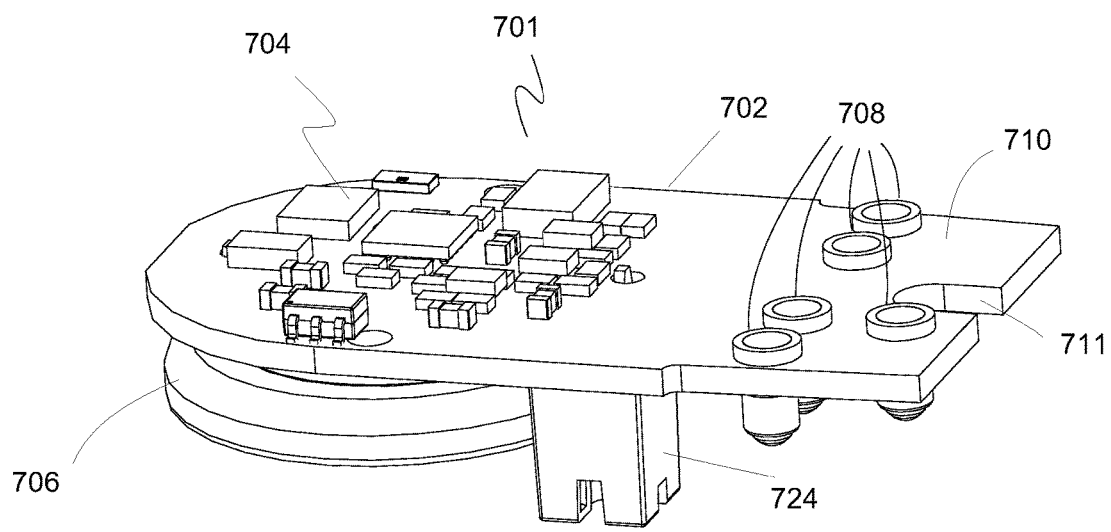
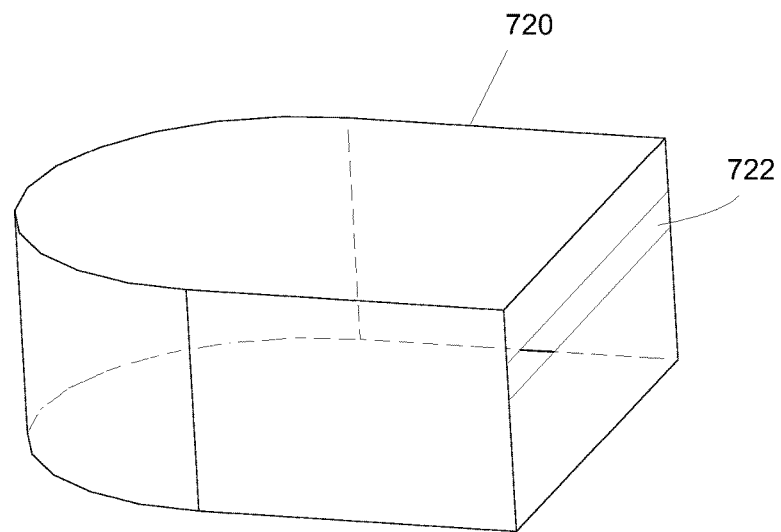
Fig. 47

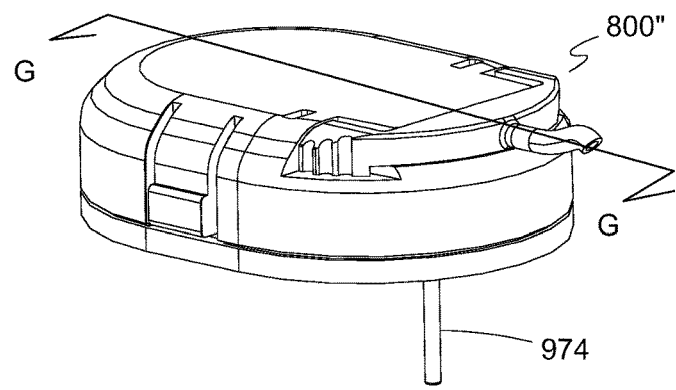
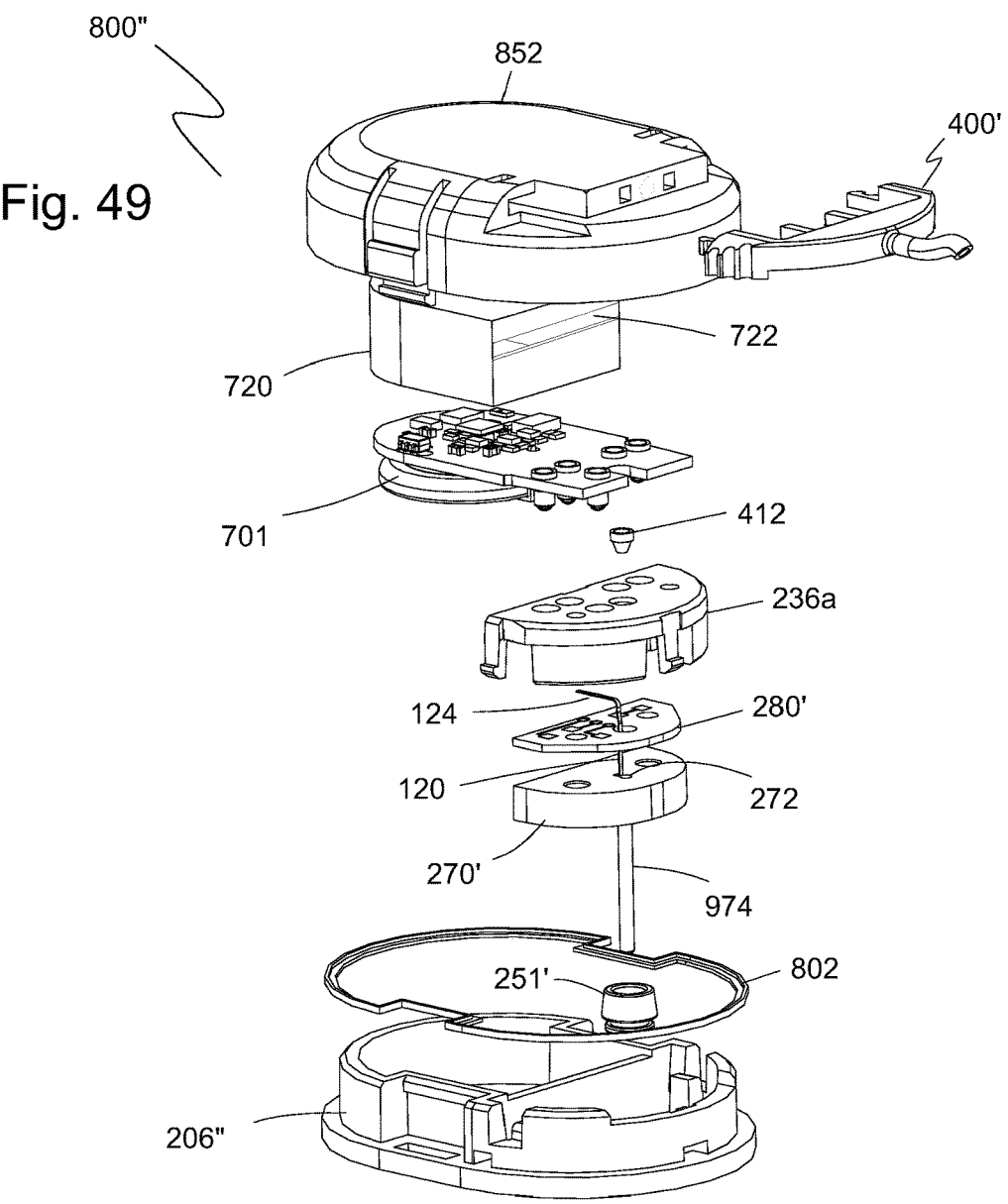

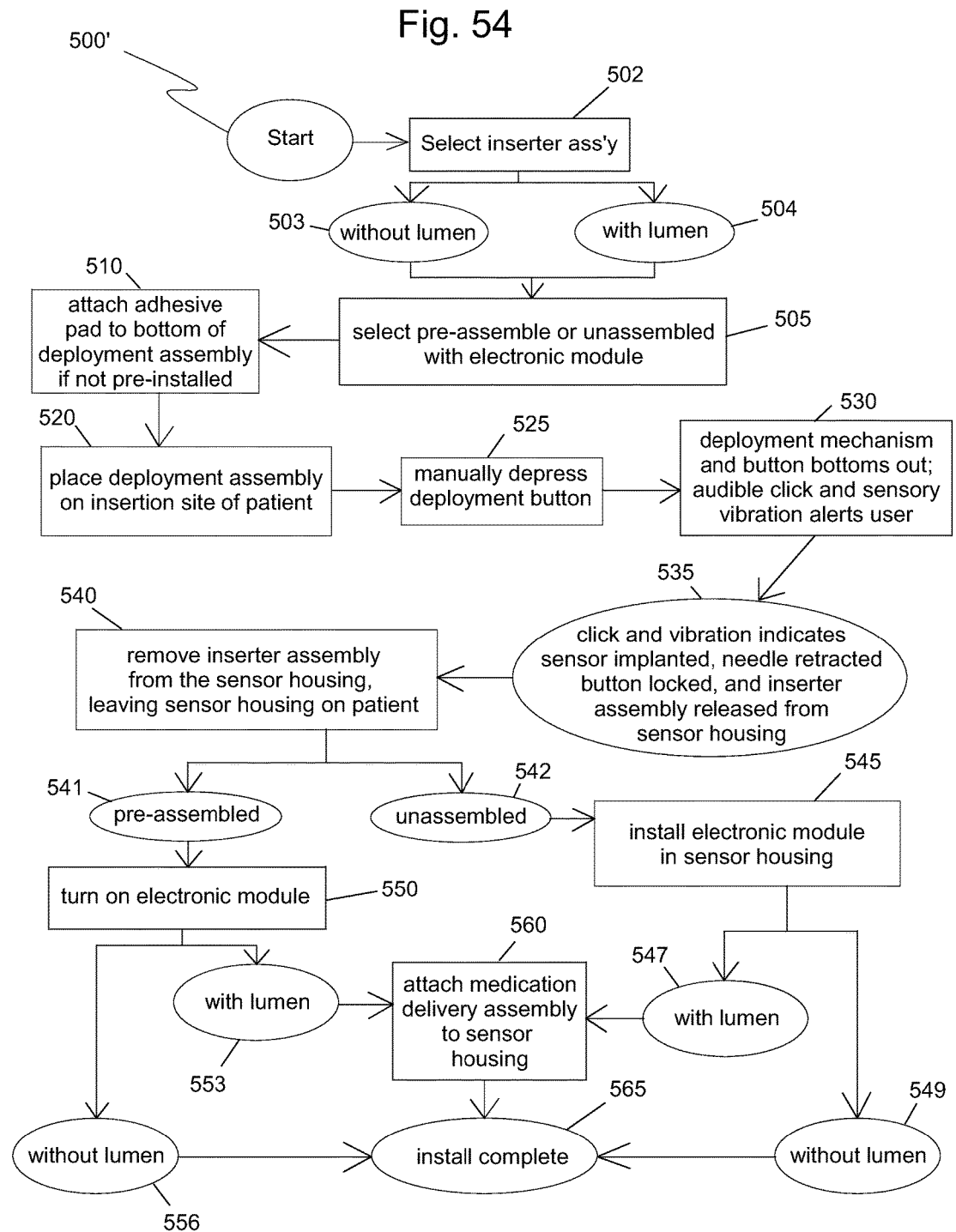

SUBCUTANEOUS SENSOR INSERTER AND METHOD

BACKGROUND OF THE INVENTION

1. Field of the Invention

The present invention relates generally to glucose monitoring sensors. More particularly, the present invention relates to glucose monitoring sensors and an inserter assembly therefor for continuous glucose monitoring in a patient.

2. Description of the Prior Art

Lancets are well-known devices commonly used in the medical field to make small punctures in a patient's skin in order to obtain samples of blood. They are utilized in hospitals, other medical facilities, and by private individuals such as diabetics for testing droplets of blood for various analytes. Typically, lancets are used only once in order to reduce the risk of HIV, hepatitis and other blood-borne diseases. The lancet or sharp of these devices is driven into the patient's skin by a small spring that is cocked by a technician or user prior to use. The lancet is covered with a protective, safety cap that keeps the end of the lancet sterile and is removed before use.

A variety of lancet devices are available for use by patients and/or healthcare practitioners. One lancet device is configured for multiple and/or repeated uses. In this variety, the user typically pushes a button or other device on a lancet injector to cause a lancet to penetrate the skin of a patient. More commonly, the lancet device effectively encases and fires the lancet into the patient's skin in order to puncture in an accurate, standardized and consistent manner. The lancet injector may also be provided with an adaptor cap to control and adjust the depth of penetration of the needle of the lancet.

Integrated lancet and sensor devices have been developed that combine the lancet and test strip or sensor into a single package. These integrated devices are typically used with a lancet injector where the integrated lancet and test strip is removed from the lancet injector and connected to a meter after acquisition by the test strip of the blood sample produced by the lancet, or used with a meter with built-in lancet injector.

More recently, continuous glucose monitoring devices have been developed for implanting into a patient's skin. Continuous monitoring systems typically use a tiny implantable sensor that is inserted under the skin, or into the subcutaneous fat layer to check analyte levels in the tissue fluid. A transmitter sends information about the analyte levels by way of, for example, a wire to a monitor or wirelessly by radio waves from the sensor to a wireless monitor. These devices are typically implanted for three to seven days of use to monitor in real-time a patient's glucose level.

One such device is disclosed in U.S. Pat. No. 5,299,571 to John Mastrototaro. The device is an apparatus for implantation of in-vivo sensors. The apparatus includes a housing, a dual-lumen tube extending therefrom, and an in-vivo sensor received within one of the lumens of the tube. A needle is received within the other lumen of the tube, and is used to insert the tube through the skin. After implantation, the needle is removed, and the flexible tube and sensor remain beneath the skin.

U.S. Patent Application Publication 2010/0022863 (2010, Mogensen et al.) discloses an inserter for a transcutaneous sensor. The inserter includes a needle unit and a sensor housing. The needle unit includes a needle hub and a carrier body. The sensor housing and the needle hub are releasably connected and when they are connected, the insertion needle is placed along the sensor (e.g. surrounding the sensor wholly or partly). The carrier body guides the movement relative to the housing between a retracted and an advanced position. When released, the needle unit and the sensor housing are forced by a spring unit to an advanced position where the needle and sensor are placed subcutaneously. Upwardly-bent parts on the leg of the housing set the insertion angle of about 30° into the skin of the patient.

U.S. Patent Application Publication 2012/0226122 (2012, Meuniot et al.) discloses an inserter device for an analyte sensor. The device includes a housing that is positioned above the subcutaneous fat layer, a blade shuttle, and a sensor shuttle. A spring is compressed between the blade shuttle and the sensor shuttle. The blade shuttle and sensor shuttle move towards the subcutaneous fat layer. When a spring force is released by the spring, the blade shuttle moves towards and pierces into the subcutaneous fat layer creating a pathway into the subcutaneous fat layer. The analyte sensor is implanted by the sensor shuttle by following the blade shuttle into the pathway created by the blade shuttle. The blade shuttle is then retracted from the subcutaneous fat layer, leaving the analyte sensor in the fat layer.

U.S. Patent Application Publication 2013/0256289 (2013, Hardvary et al.) discloses a diagnostic device. The diagnostic device has partially retractable hollow guide needles for the intradermal placement of diagnostic elements fixedly connected to measuring means within this device. This obviates the need to remove the guide needle and to connect the diagnostic elements to the measuring means after placement into the skin.

SUMMARY OF THE INVENTION

Continuous glucose monitoring (CGM) devices have been slow to be adopted by many patients due to the pain and long term discomfort of initial deployment and long term use (3 to 7 days). Currently available devices are commonly compared and criticized on CGM user forums for their pain of deployment.

Pain of deployment can be shown to be directly related to the design of the device. Axons that pass through the subcutaneous layer and end in the epidermis are called nociceptors. These specialized neurons transmit pain messages. The density of these pain receptors ranges between 2 and 2500 neurites/mm² just below the skin surface, and varies greatly depending on location. The probability and magnitude of a pain response during any incision is proportional to the number of affected nociceptors and the trauma inflicted upon these nociceptors. With nociceptors located throughout the thickness of the epidermis, a deeper incision is more likely to trigger a pain response due to the increased likelihood of trauma to more nociceptors.

When inserted into subcutaneous tissue, the combined cross sectional area of a sensor and introducer is proportional to the force of insertion and also to the probability and magnitude of triggering pain response. FIG. 1 is a graph 10 showing the maximum peak force 12 of insertion (lbs.) of various commercial inserter sets plotted against the measured cross section area 14 of the inserter set (in²×10⁻⁴). As can be seen by a linear regression of the data points in FIG. 1, the peak force increases linearly with cross sectional area with a regression line 16 represented by equations 1 and 1a, which have an $R^2$ value of 0.932. Data in graph 10 is for needles inserted at 90 degrees to the skin surface regardless of the intended insertion angle of the particular needle.

$$\text{peak force (lb}_f\text{)} = (0.3998)(\text{cross sectional area (in}^2\text{)}) + 0.0556 \text{ lb}_f \quad (1)$$

$$\text{peak force (N)} = (0.0223)(\text{cross-sectional area (m}^2\text{)}) + 1.100 \text{ N} \quad (1a)$$

Among the tested needles for graph 10 in FIG. 1 and graph 20 in FIG. 2, Brand A is a 22 gauge split needle with a lumen, Brand B is a 22-24 gauge needle with a bi-lumen, Brand C is a 23-24 gauge split needle with a single lumen, and Brand D is a 26 gauge needle. A split needle means that about a third of the needle is removed for a distance creating a skive cut in the needle. The Brand A needle with lumen has the highest peak force. The Brand C needle has a peak force that is slightly less than the larger 22 gauge Brand A split needle. The Brand D needle is a needle intended for insertion at 45 degrees to the skin surface. It is notable that the peak force increases by 11% when inserting a needle at 45 degrees compared to 90 degrees to the skin surface. Thus, when used as intended, the peak force for Brand D needle would be 11% greater than as shown in FIG. 1.

It is important to note that the sensor of the present invention was installed in various needle sizes and also tested for peak insertion force. As can be seen from the graph, the sensor of the present invention in a 22 gauge split needle has a lower peak insertion force than the comparable Brand C needle. Also, the sensor of the present invention in a 24 gauge split needle had a lower peak insertion force than the Brand D 26 gauge needle notwithstanding having a larger cross-sectional area than the Brand D needle. The needle with the lowest peak force (FIG. 1) and lowest work (FIG. 2) is the sensor of the present invention in a 27 gauge XTW Skive Cut needle with an oval cross-sectional shape.

The cross sectional area of an inserter set (i.e. needle and sensor) also strongly correlates with the relative intensity of pain of insertion as reported by users of these devices. The Brand D device is considered by users as being much more comfortable than the earlier Brand A system. The present invention the same or a larger needle gauge has a better (lower) peak insertion force of a comparable brand needle as seen from FIGS. 1 and 2.

FIG. 2 is a graph 20 showing work 22 (lb-in) plotted against the combined cross sectional area 24 (in$^2$×10$^{-4}$) of the sensor and introducer of various commercial introducer sets. For insertion of a sensor and introducer in combination, the length or depth of insertion into subcutaneous tissue is proportional to the work energy (force times distance) and also proportional to the probability and magnitude of triggering pain response from the user. As can be seen by a linear regression of the data points of FIG. 2, the work increases linearly with cross sectional area with a regression line 26 represented by equations 2 and 2a, which have an R$^2$ value of 0.9715.

$$\text{Work (lb-in)} = (0.0439)(\text{cross sectional area (in}^2\text{)}) + 0.0133 \quad (2)$$

$$\text{Work (N-m)} = (6.23\text{E}-5)(\text{cross-sectional area (m}^2\text{)}) + 1.50\text{E}-3 \text{ N-m} \quad (2a)$$

FIG. 3 is a graph 30 with typical force of insertion 32 (lbs.) plotted against insertion distance 34 (in) to demonstrate the concept of work energy. FIG. 3 is a plot of data obtained from three separate insertion force measurements for a Brand R inserter with a Brand R sensor. As the sharp penetrates tissue, the force is dynamically recorded. The integral of a curve 36 (i.e., the area 38 under one of curves 36a-36c) is the work energy (lb-in). Work energy (force times distance) is proportional to the incidence of triggering a pain response by users of the inserter. In simple terms, small, shallow incisions hurt less for the reasons stated above. Therefore, an inserter that reduces or minimizes insertion pain is more likely to be adopted by patients.

Reducing or minimizing insertion pain is one criterion for patient acceptance of any continuous monitoring system. Other criteria include the convenience and ease-of-use of the inserter device. Therefore, a need exists for an inserter set and an inserter assembly that reduces or minimizes the patient's pain and inconvenience of inserting a continuous monitoring sensor. The present invention achieves these and other objectives by providing a continuous analyte monitoring inserter apparatus for subcutaneous placement of a sensor into a patient and a sharp/needle that minimizes insertion pain with a reduced cross-sectional area.

In one embodiment of the present invention, a sharp useful for continuous glucose monitoring has an elongated tubular body with a pointed tip. The elongated tubular body has a generally oval or elliptical cross-sectional shape and defines a conduit therethrough. A sharp open region extends a predefined distance from the pointed tip along the elongated tubular body and has a portion of the generally oval tubular body removed, thereby defining an unenclosed concave well within the remaining elongated tubular body. In another embodiment, the sharp includes a continuous monitoring sensor retained in the concave well, where the top surface of the continuous monitoring sensor resides completely within the concave well formed by the wall of the tubular body.

Another aspect of the present invention is an inserter assembly. In one embodiment, the inserter assembly is a single action inserter assembly adapted to substantially simultaneously using a single action perform the steps of (1) implanting the sensor subcutaneously into the patient, (2) fixedly seating a sensor deployment assembly that includes the sensor within a sensor housing attached to the patient, (3) retracting a needle used to implant the sensor, and (4) releasing the inserter assembly from the sensor housing. In one embodiment, the action of retracting the needle is performed by retracting the needle into the inserter assembly. In another embodiment, the inserter assembly further includes implanting a lumen along with the sensor subcutaneously in the patient.

In another embodiment, the inserter assembly includes a deployment button containing a needle deployment mechanism. The needle deployment mechanism has a needle carrier incorporating a sharp and a needle carrier catch that temporarily prevents the needle carrier from moving. The deployment button is movably received in a housing body, where the housing body has a sensor deployment assembly that connects in mating agreement to the sharp. The sharp extends beyond the sensor deployment assembly into the sensor housing and contains the sensor, which is not fixedly attached to the sharp. A sensor housing is releasably received within the housing body.

In another embodiment, the inserter assembly includes a housing body having a first body end and a second body end. A deployment button is at least partially disposed in and slidable within the housing body through the first body end, where the deployment button is movable between a first position and a second position. The second position may be a locked position. A deployment mechanism slidably disposed within the deployment button is movable between a ready position, an insertion position, and a retracted position. The deployment mechanism has a needle.

A sensor deployment assembly is disposed within the housing body and removably mated with the deployment mechanism. The sensor deployment assembly has a needle bore in which the needle is disposed when the deployment mechanism is in the ready position. A sensor is partially disposed within the needle or the needle bore, where the deployment mechanism, the needle, and the sensor define a deployment axis. The sensor has an electrode system and an electrical contact portion. In one embodiment, the electrical contact portion is parallel to but spaced from the deployment axis. In another embodiment, the electrical contact portion extends transversely away from the deployment axis. In one embodiment, for example, the electrical contact portion extends substantially perpendicularly from the deployment axis.

The inserter assembly also includes a sensor housing disposed at and removably retained by the second body end of the housing body. The sensor housing has a bottom surface that defines a sensor opening therethrough and aligned with the deployment axis.

Movement of the deployment button from the first position to the second position causes the sensor to be implanted subcutaneously into the patient along the deployment axis, the needle of the deployment mechanism to retract to the retracted position, the sensor deployment assembly to be fixed within the sensor housing, and inserter assembly to release from the sensor housing. In one embodiment, the inserter assembly includes the housing body, the deployment button and the deployment mechanism.

In some embodiments, the movement of the deployment button from the first position to the second position is a single movement causing substantially at the same time the sensor to be implanted subcutaneously into the patient along the deployment axis, the needle of the deployment mechanism to retract to the retracted position, the sensor deployment assembly to be fixed within the sensor housing, and the housing body, the deployment button and the deployment mechanism to release from the sensor housing.

In one embodiment, the single activation has an auditory indication that the sensor is implanted in the patient and the inserter assembly is released from the sensor housing. In another embodiment, the single activation has a sensory indication through the inserter assembly that the sensor is implanted in the patient and the inserter assembly is released from the sensor housing.

In another embodiment, the housing body has a body recess for receiving and retaining a button catch when the deployment button is in the second position.

In another embodiment, the housing body has a body catch retaining the sensor housing partially within the housing body. The body catch is released from the sensor housing by the deployment button when the deployment button is oriented in the second position.

In another embodiment, the inserter assembly further includes a lumen disposed on the needle, where the inserter assembly substantially simultaneously implants the lumen with the sensor subcutaneously into the patient In another embodiment, the sensor deployment assembly includes a sensor deployment body, a sensor deployment guide, and a sensor carrier. The sensor deployment body has a sensor deployment locking mechanism configured to engage the sensor housing when the button is moved to the second locked position, thereby locking the sensor deployment assembly with the sensor housing. In one embodiment, the sensor deployment locking mechanism is one or more resilient deployment catches on the sensor deployment assembly biased to engage a deployment catch surface on the sensor housing. Similarly, the deployment locking mechanism may be one or more resilient deployment catches on the sensor housing that are biased to engage respective deployment catch surfaces on the sensor deployment assembly.

The sensor deployment guide is attached to the sensor deployment body and positioned to stop travel of the deployment assembly when the deployment button is moved to the second locked position. For example, the deployment guide comes in contact with the sensor housing to stop travel of the deployment assembly. The sensor carrier is attached to the sensor deployment guide, secures the sensor, and has a board-receiving face. The sensor carrier also defines a sensor bore extending transversely from and in communication with the needle bore. The sensor extends through the sensor bore and along the board-receiving face. In one embodiment, the board-receiving face is substantially parallel to but spaced apart from the deployment axis, where the sensor bends over the sensor carrier. In other embodiments, the board-receiving face is on top surface of the sensor carrier.

In some embodiments, the sensor deployment assembly further includes a sensor board with electronic coupling pads electrically coupled to the electrical contact portion of the sensor. The sensor board mates with the board-receiving face and in electrical communication with the electrical contact portion of the sensor. The electronic coupling pads are positioned to be electrically coupled to measuring electronics.

In another embodiment, the board-receiving face is on a top sensor carrier surface and extends transversely to the deployment axis. In such an embodiment, a sensor board mates with the board-receiving face and has electronic coupling pads positioned to electrically couple to measuring electronics. The sensor extends through the sensor bore and along the sensor board with the electrical contact portion of the sensor electrically coupled to the electronic coupling pads.

In some embodiments, the sensor carrier defines a sensor groove along the top sensor carrier surface, where the sensor extends through the sensor groove on its way to the board-receiving face or sensor board.

In some embodiments, the deployment axis is substantially perpendicular to the bottom surface of the sensor housing, where the bottom surface of the sensor housing is configured to contact the patient during implantation of the sensor.

In some embodiments, the inserter assembly includes a lumen with a portion of the lumen sealingly fixed to the sensor deployment assembly and extending through the needle opening to a lower lumen end. In some embodiments, the lumen is a single lumen tube sized to receive the needle and the sensor therein, where the electrode system on the sensor extends from the lower lumen end of the single lumen tube. In some embodiments, a working electrode of the electrode system is spaced from the lower lumen end of the single lumen tube by about 4 mm to about 7 mm. In other embodiments, the working electrode is spaced from the lower lumen end by about 2 mm to about 10 mm.

In other embodiments, the lumen is a dual lumen tube defining a first lumen tube for receiving the needle therethrough and a second lumen tube for receiving the sensor. The second lumen tube defines a second lumen side opening adjacent an upper lumen end and in communication with the needle bore. The second lumen tube also defines one or more second lumen electrode opening adjacent the lower lumen end to expose an electrode system on the sensor to a sample to be measured. In some embodiments, it is contemplated that the needle may be a solid needle; in other embodiments, the needle defines a passageway therethrough. Accessible through the second lumen side opening, the working electrode of the electrode system in some embodiments is spaced from the lower lumen end of the single lumen tube by about 4 mm to about 7 mm. In other embodiments, the working electrode is spaced from the lower lumen end of the single lumen tube by about 2 mm to about 10 mm.

In other embodiments, the inserter assembly includes a sealing cover or cover assembly that is releasably attachable to a top of the sensor deployment assembly. The sealing cover includes resilient sensor housing engagement tabs, where each has a tab catch configured to be received within a corresponding engagement tab receiver in the sensor housing to lock the sealing cover to the sensor housing. The sealing cover also has a sealing member on a bottom surface that aligns with and seals into the needle bore.

In some embodiments, the sealing cover defines a delivery bore with a first bore end and a second bore end at a delivery bore opening through a bottom surface of the sealing cover. In some embodiments, the sealing cover includes a flexible medication delivery tube connected to the first bore end of the delivery bore.

In yet other embodiments, the inserter assembly includes an electrical component housing that is releasably attachable to the sensor housing and configured to receive and transmit electrical signals generated by the electrode system on the sensor.

In other embodiments, the inserter assembly includes a cover assembly that is releasably attachable to a top of the sensor deployment assembly. The cover assembly has a sensor housing engagement mechanism configured to engage the sensor housing to lock the cover assembly to the sensor housing. A sealing member on a bottom surface of the cover assembly aligns with and forms a seal between the delivery bore and the needle bore. A sensor board with electronic coupling pads is electrically coupled to the electrical contact portion of the sensor, where the sensor board mates with the board-receiving face with the electronic coupling pads positioned for being electrically coupled to measuring electronics. The cover assembly also includes an electrical component configured to receive and transmit electrical signals generated by the electrode system on the sensor. The electrical component has electrical contacts coupled to the electronic coupling pads on the sensor board.

In other embodiments, the inserter assembly includes a resilient button catch on the housing body or the sensor housing, where the button catch is biased to engage a button catch surface on the other of the housing body or the sensor housing when the deployment button is in the second position. The inserter assembly may also include a resilient needle-carrier catch on the deployment button or the needle carrier, where the needle-carrier catch is biased to disengage a second catch surface on the other of the deployment button or the needle carrier when the deployment button is moved to the second position. The inserter assembly may also include a resilient housing catch on the housing body or the sensor housing, where the housing catch is biased to disengage a housing catch surface on the other of the housing body or the sensor housing when the button in moved to the second position.

In another aspect of the invention, a method of inserting an in-vivo analyte sensor subcutaneously for continuous analyte monitoring of a patient includes the steps of providing a single action inserter assembly having a needle, an implantable sensor, a deployment button for implanting the implantable sensor using the needle and for retracting the needle, and a sensor housing for retaining the implanted sensor in an implanted orientation once deployed by the deployment button; and using a single action to activate the deployment button of the single action inserter assembly that causes the following actions to substantially simultaneously occur: (1) implanting the sensor subcutaneously into the patient, (2) fixedly seating the sensor within the sensor housing attached to the patient, (3) retracting the needle into the inserter assembly, and (4) releasing the inserter assembly from the sensor housing.

In another embodiment of the method, the providing step includes providing a single action inserter assembly that has a lumen disposed on the needle and the using step includes implanting the lumen subcutaneously into the patient with the sensor and fixedly seating the lumen within the sensor housing attached to the patient.

In another aspect of the present invention, a continuous analyte monitoring inserter apparatus for subcutaneous placement of a sensor into skin of a patient minimizes pain to a patient. In one embodiment, the apparatus has a single action inserter assembly having a housing body with a first body end and a second body end. A deployment button is partially disposed in and slidable within the housing body through the first body end, where the deployment button being movable between a first position and a second position. A sensor housing is partially disposed within and removably retained in the second body end. A needle is movably disposed within the single action inserter assembly. The needle has a cross-sectional shape that minimizes a peak force of insertion into the skin of the patient. An implantable sensor is partially disposed within the needle. The inserter assembly is adapted to substantially simultaneously implant the sensor subcutaneously into the patient, retract the needle, fix the sensor within the sensor housing and release the inserter assembly from the sensor housing with a single activation of the deployment button caused by moving the deployment button from the first position to the second position while minimizing pain to the patient.

In another embodiment, a longitudinal portion of the needle has a skive cut along a length of the needle from a sharp end of the needle to a predefined location.

In another embodiment, the needle is oriented substantially perpendicular to a surface of the single action inserter, where the surface is a portion of the sensor housing and intended for placement against the skin of the patient.

In another embodiment, the needle has a cross-sectional shape of an oval, an ellipse, an egg-shape, or an oblong shape. In another embodiment, the longitudinal portion of the needle has a cross-sectional shape of an oval, an ellipse, an egg-shape, or an oblong shape.

In another aspect of the present invention is a method of minimizing pain when inserting an in-vivo analyte sensor subcutaneously for continuous analyte monitoring of a patient. In one embodiment, the method includes providing a single action inserter assembly having a needle with a cross-sectional shape that minimizes a peak force of insertion into the skin of the patient, an implantable sensor, a deployment button for implanting the implantable sensor using the needle and for retracting the needle, and a sensor housing for retaining the implanted sensor in an implanted orientation once deployed by the deployment button; and using a single action to activate the deployment button of the single action inserter assembly that causes the following actions to substantially simultaneously occur: (1) implanting the sensor subcutaneously into the patient, (2) fixedly seating the sensor within the sensor housing attached to the patient, (3) retracting the needle used to implant the sensor into the inserter assembly, and (4) releasing the inserter assembly from the sensor housing, wherein the needle and the single action minimizes pain when inserting the sensor subcutaneously.

In another embodiment of the method, the providing step includes providing a needle with a skive cut along a longitudinal portion of the needle from a sharp end of the needle to a predefined location along the length of the needle.

In another embodiment of the method, the providing step includes providing a needle that is oriented substantially perpendicular to a surface of the single action inserter, where the surface is a portion of the sensor housing and intended for placement against the skin of the patient.

In another embodiment of the method, the providing step includes providing a needle with an oval, elliptical, egg-shaped, or oblong cross-sectional shape. In another embodiment of the method, the providing step includes providing a needle with the longitudinal portion having an oval, elliptical, egg-shaped, or oblong cross-sectional shape.

In another aspect of the present invention, a method of making a sharp includes providing a longitudinal tubular body having a first end and a second end; compressing the longitudinal tubular body to have a substantially oval and/or elliptical cross-sectional shape; removing a portion of the tubular body proximate the first end and extending a predefined distance towards the second end where the portion is parallel to a major axis of the oval/elliptical cross-sectional shape; and forming a sharp tip on the first end.

In yet another aspect of the present invention, a method of continuous analyte monitoring includes placing an inserter assembly on an insertion site of a patient. The inserter assembly has a sensor carrier, an inserter set with a sharp and an analyte sensor, and a deployment assembly. The deployment assembly includes a deployment button, a housing body, and a deployment mechanism. The method also includes the steps of pressing the deployment button of the introducer set, thereby deploying the introducer set into subcutaneous tissue of the patient; retracting the deployment assembly and removing the sharp from the patient while leaving the analyte sensor deployed in the sensor carrier and in the patient; and removing the deployment assembly from the sensor carrier.

BRIEF DESCRIPTION OF THE DRAWINGS

FIG. 3 is a graph showing data for one inserter set of the prior art, where insertion force is plotted against the distance of insertion and where the area under a curve is the work energy.

FIG. 4 is a perspective view of one embodiment of a sharp of the present invention showing the sharp tip, a sharp open region, and a portion of the sharp body.

FIG. 5 is an end perspective view of the sharp of FIG. 4 showing the concave well defined by the sharp open region.

FIG. 5A is a diagram representing the cross-sectional area of the sharp open region of the sharp of FIG. 5 with a sensor disposed in the concave well.

FIG. 8 is a graph showing data for one inserter set of the present invention, where insertion force is plotted against the distance of insertion and where the area under a curve is the work energy.

FIG. 15 is an enlarged perspective view of the sensor carrier with sensor showing the back side of one embodiment of the sensor.

FIG. 16 is an enlarged perspective view of the sensor carrier with sensor showing the front side of the sensor and the proximal end portion of the sensor shown in FIG. 15.

FIGS. 17 and 18 are enlarged front and back perspective views of the sensor shown in FIGS. 15-16, respectively.

FIG. 21 is an enlarged perspective view of the sensor, sensor board and the electronic component housing.

FIG. 22 is an enlarged side view of the sensor, sensor board and the electronic component housing shown in FIG. 21.

FIG. 24 is a sectional view of a sensor carrier with a single lumen configuration.

FIG. 24A is an enlarged view of the sensor carrier with the single lumen configuration shown in FIG. 24.

FIG. 24B is an enlarged perspective view of another embodiment of a sensor carrier with sensor and single lumen showing the back side of the sensor carrier.

FIG. 24C is an enlarged perspective view of the sensor carrier with sensor and single lumen showing the front side of the sensor and the proximal end portion of the sensor shown in FIG. 24B.

FIG. 24D is an enlarged cross-sectional view of the sensor carrier shown in FIG. 24B.

FIG. 24E is a bottom view of the sensor carrier shown in FIG. 24B.

FIG. 34 is a perspective view of another embodiment of an inserter assembly of the present invention.

FIG. 35 is a front view of the inserter assembly of FIG. 34.

FIG. 36 is a side, cross-sectional view of the inserter assembly of FIG. 34 as taken along line E-E with the button and deployment mechanism in respective first or up positions.

FIG. 37 is an enlarged, cross-sectional view of the sensor deployment assembly of FIG. 36.

FIG. 38 is a rear, cross-sectional view of the inserter assembly of FIG. 34.

FIG. 46 is an enlarged, perspective view of the electronic circuit board assembly of the electronic module partially shown in FIG. 45.

FIG. 47 is an enlarged, perspective view of the electronic module housing of the electronic module shown in FIG. 45.

FIG. 48 is side and top perspective view of another embodiment of a sensor housing assembly of the present invention showing a dual lumen and a medication delivery assembly connected to the sensor housing assembly.

FIG. 49 is an exploded view of the sensor housing assembly of FIG. 48 showing various components.

FIG. 54 is a flow chart showing the steps of the process that occurs when an inserter assembly of the present invention is used to implant an analyte sensor subcutaneously in a patient.

DETAILED DESCRIPTION OF THE PREFERRED EMBODIMENT

Figure 1:
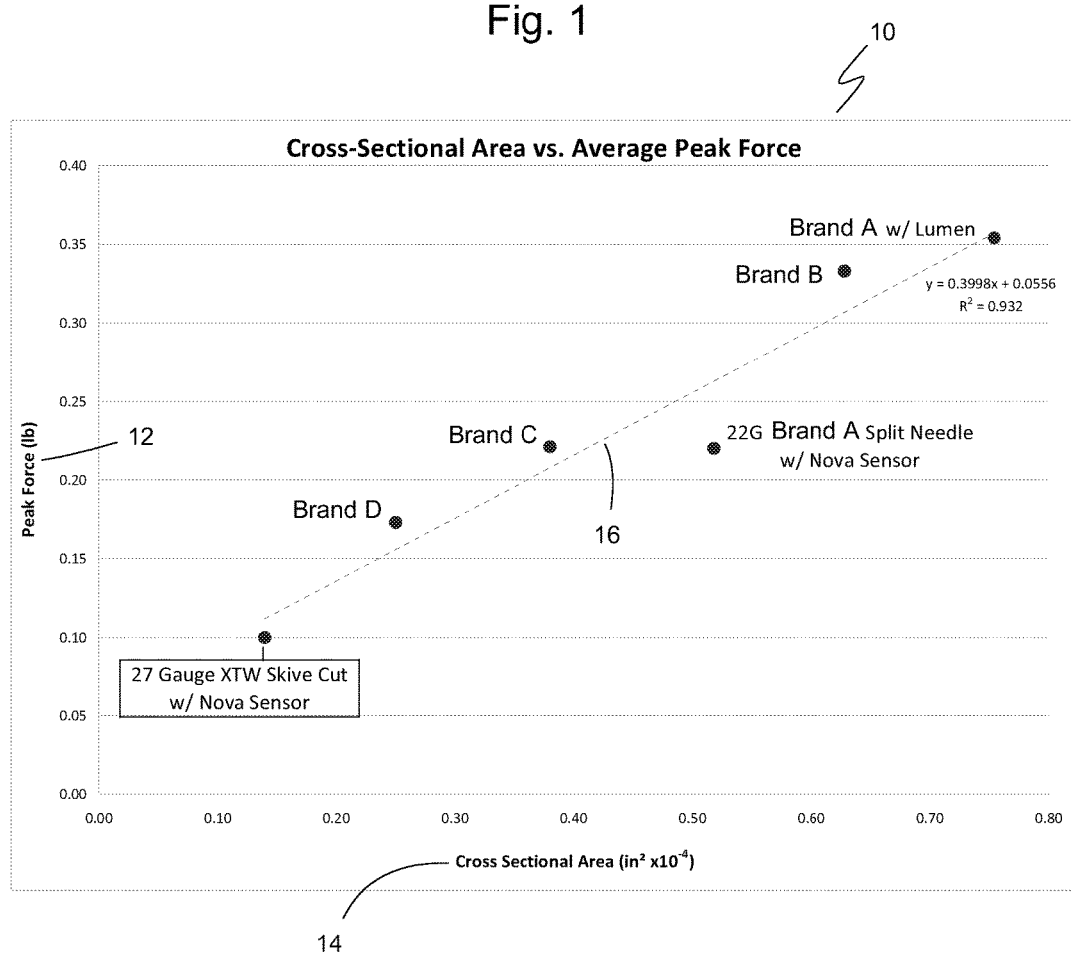
FIG. 1 is a graph showing insertion force data for various commercial inserter sets of the prior art, where maximum peak force of insertion is plotted against the measured cross sectional area of the inserter set.
Figure 2:
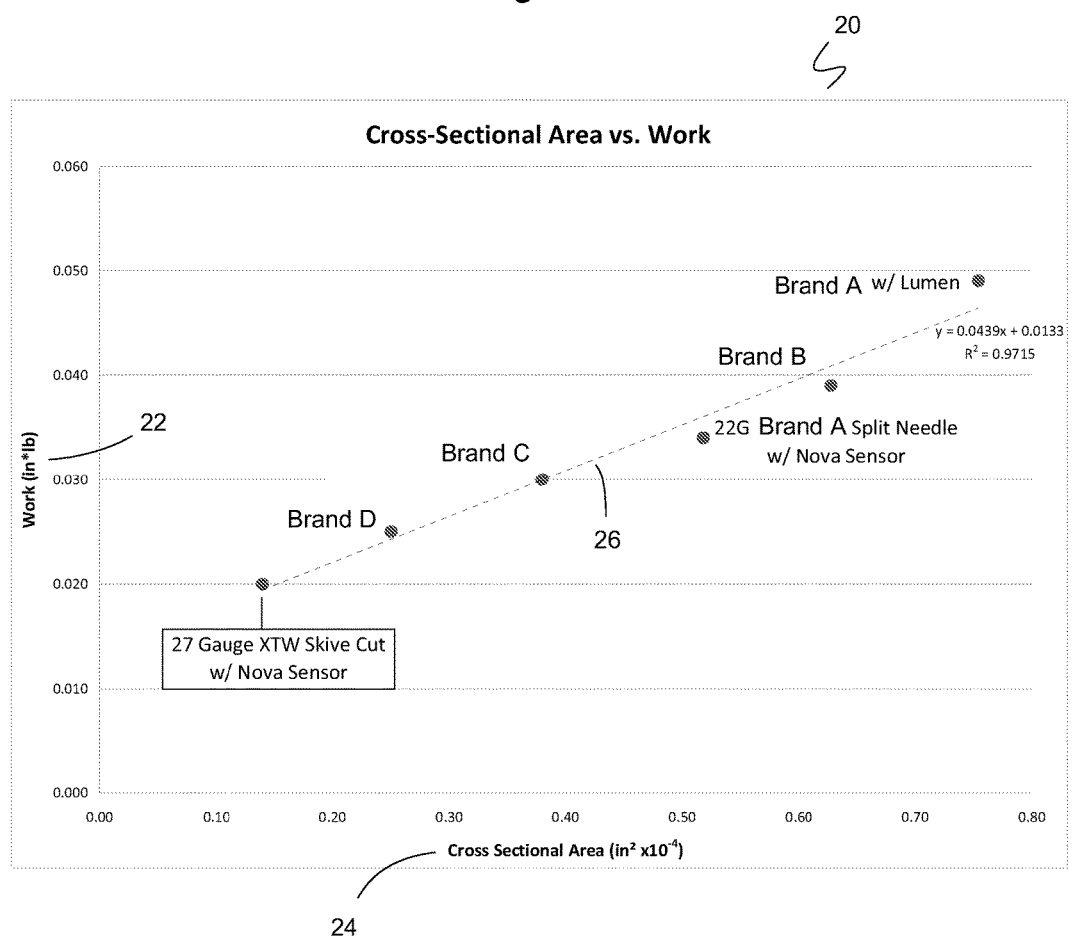
FIG. 2 is a graph showing data for various commercial inserter sets of the prior art, where the work of insertion is plotted against the measured cross sectional area of the inserter set.

Exemplary embodiments of the present invention are illustrated in FIGS. 4-54. FIGS. 4 and 5 illustrate perspective views of one embodiment of a sharp 100 of the present invention. Sharp 100 includes a sharp body 102, a sharp open region 104, and a sharp tip 106. Sharp body 102 is an annular section of sharp 100 that extends longitudinally and defines an enclosed conduit 101 therethrough. In one embodiment, sharp 100 is made from 27 gauge XTW stainless tubing having an outside diameter of about 0.016 inch (0.41 mm) nominal and an inside diameter of about 0.012 inch (0.30 mm) nominal. The tubing is then flattened to have an oval or elliptical shape with an outside height 108 along the minor axis of the oval or elliptical shape of about 0.0120 inch (0.30 mm).

A wire EDM machining operation is used to remove a portion of the tubing wall 103 along sharp 100 a predefined distance to define sharp open region 104, thereby reducing the overall height 110 of sharp 100 along the minor axis of the oval or elliptical shape at sharp open region 104 to about 0.008 inches (0.20 mm). The wire EDM machining operation can be performed on cylindrical tubing or on flattened, oval tubing as described above. Sharp open region 104 is a section of an annulus that extends longitudinally with the tubing wall 103 along the length of sharp open region 104 defining an unenclosed concave well 114 from sharp tip 106 to sharp body 102.

Figure 6:
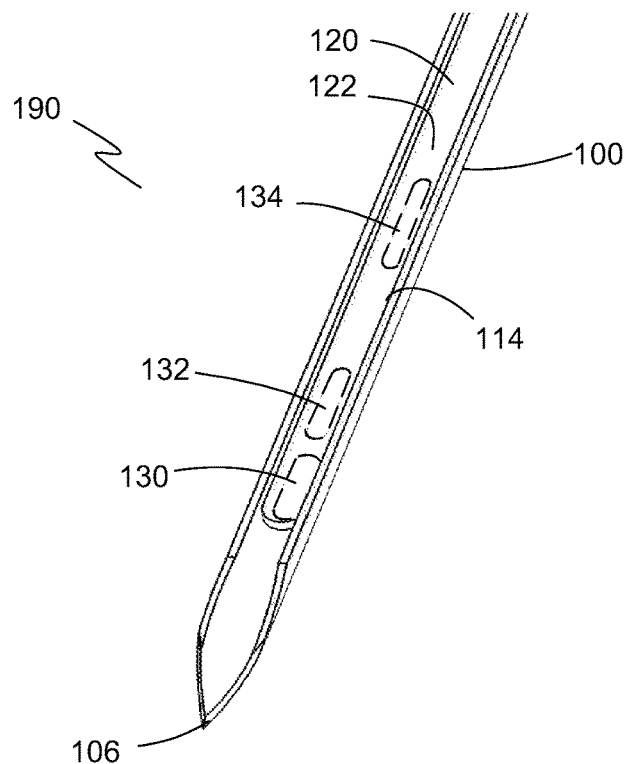
FIG. 6 is a perspective view of an inserter set of the present invention showing a portion of the sharp of FIG. 4 with a continuous monitoring sensor disposed in the concave well.
Figure 7:
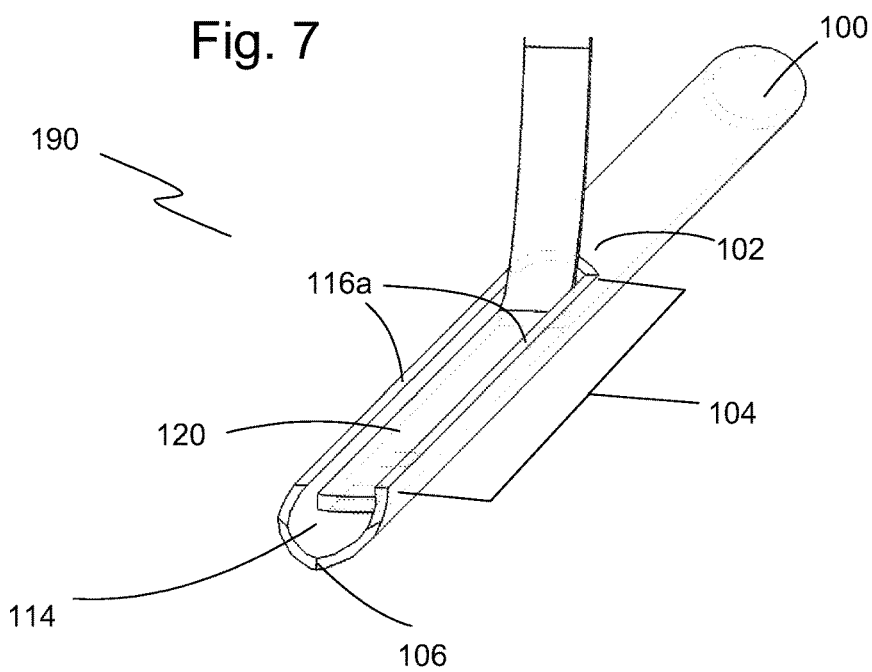
FIG. 7 is an end perspective representation of the inserter set of the present invention showing the continuous monitoring sensor disposed in the concave well.

Concave well 114 is sized to receive a continuous monitoring sensor 120 (shown in FIGS. 6-7). In one embodiment, concave well 114 is sized to receive a continuous monitoring sensor 120 having a size up to about 0.012 (0.30 mm) wide by about 0.004 (0.10 mm) thick. In one embodiment, a continuous monitoring sensor top surface 122 is positioned flush with or below a top surface 116a of tubing wall 116 along sharp open region 104. The incision of such a sharp and sensor combination has a cross sectional area 112 of about $1.33 \times 10^{-3}$ in$^2$ (0.81 mm$^2$), where cross sectional area 112 is defined within outside surface 100a of tubing wall 103 and top surface 116a of tubing wall 116 at sharp open region 104 (also shown in FIG. 5A). Having continuous monitoring sensor 120 disposed in concave well 114 of sharp 100 minimizes the combined cross sectional area of the sharp and sensor as compared to cylindrical sharps of the same tubing or cylindrical sharps with a sharp open region but a continuous monitoring sensor that extends out of the sharp open region. As a result, the insertion force for sharp 100 with continuous monitoring sensor 120 is considerably lower than the insertion force of prior art insertion sets.

Referring to FIGS. 6 and 7, portions of an embodiment of an inserter set 190 of the present invention are shown. Inserter set 190 has a continuous monitoring sensor 120 disposed in concave well 114 of sharp 100. As shown in FIG. 6, continuous monitoring sensor 120 has a working electrode 130, a counter electrode 132, and a multi-segmented reference electrode 134 along a sensor top surface 122. In one embodiment as shown in FIG. 7, continuous monitoring sensor 120 extends along all or a major portion of sharp open region 104 from sharp tip 106 to sharp body 102 and at least partially into sharp body 102. In one embodiment, continuous monitoring sensor does not occupy sharp tip 106 so as to retain a smooth sloped profile of sharp 100 at tip 106.

Figure 6A:
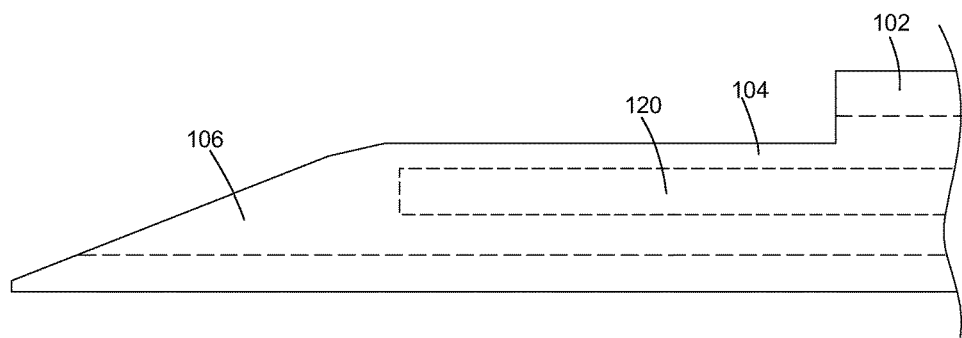
FIG. 6A is a side view of a portion of the inserter set of FIG. 6 showing the continuous monitoring sensor disposed in the concave well of the sharp.

FIG. 6A is a side view of part of inserter set 190 with continuous monitoring sensor 120 disposed in concave well 114 of sharp 100. Sharp 100 is constructed so that continuous monitoring sensor 120 is securely held in concave well 114 during insertion into skin tissue by frictional engagement with an inside surface 100b of tubing wall 103. Optionally, a water-soluble adhesive or other compound (not shown) is applied between continuous monitoring sensor 120 and concave well 114, where the water-soluble adhesive or other compound dissolves and releases continuous monitoring sensor 120 when sharp 100 is deployed into skin tissue.

Figure 7A:
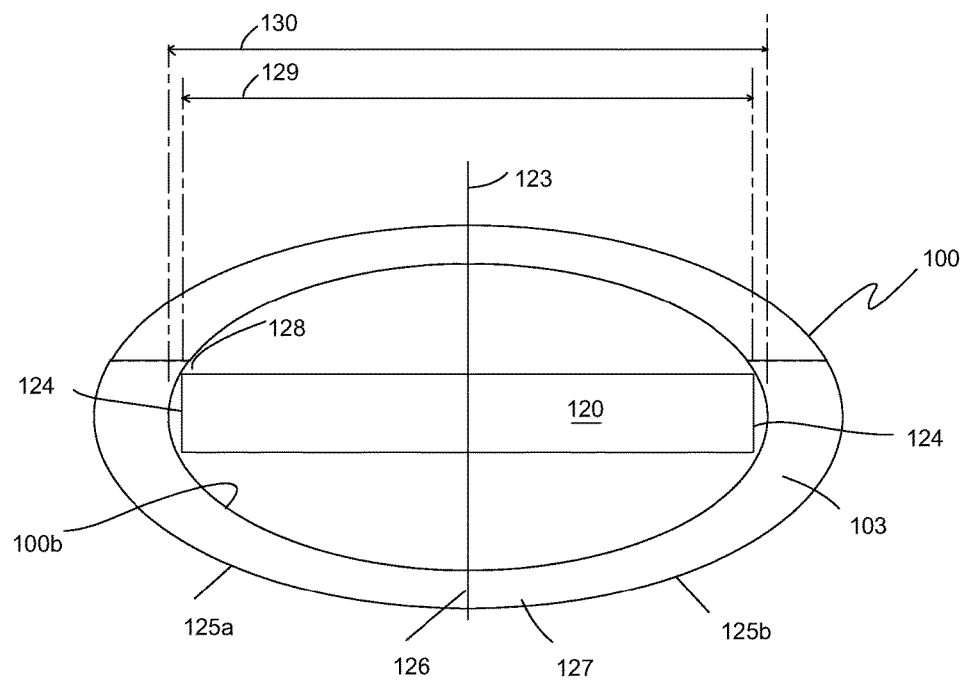
FIG. 7A is an end representation of an inserter set of the present invention showing the shape of the sharp and concave well with a continuous monitoring sensor disposed in the concave well.

In one embodiment shown in an end view of FIG. 7A, tubing wall 103 along sharp open region 104 (shown in FIGS. 6A & 7) occupies more than 180° of the oval shape. From a vertical line 123 bisecting the oval into right and left halves 125a, 125b, tubing wall 103 extends more than 90° along the elliptical/oval paths away from vertical line 123 on each half 125a, 125b from a point of intersection 126 between vertical line 123 and lower portion 127 of oval. As a result, tubing wall 103 extends upward and then curves back toward vertical line 123 to define an opening 128 in sharp open section 104 that has a reduced width 129 compared to a maximum width 130 of concave well 114. Since tubing wall 103 arcs toward vertical line 123, reduced width 129 of opening 128 restricts continuous monitoring sensor 120 from exiting through opening 128. In one embodiment, sidewalls 124 of continuous monitoring sensor 120 frictionally engage an inside surface 100b of tubing wall 103. For enhanced frictional engagement, continuous monitoring sensor 120 optionally has a cross-sectional shape that substantially matches that of concave well 114 along one or more sides of continuous monitoring sensor 120. Therefore, continuous monitoring sensor 120 may be installed and removed from sharp 100 by sliding it into or out through sharp tip 106 (shown in FIG. 6). After insertion, sharp 100 is removed from the tissue and continuous monitoring sensor 120 remains in the tissue. Thus, sharp 100 can be retracted while continuous monitoring sensor 120 remains in the tissue for continuous glucose monitoring.

Referring now to FIG. 8, a plot 80 shows insertion force data for inserter set 190 of the present invention with force of insertion 82 plotted vs. the distance 84 of insertion. Each of plotted lines 86 in FIG. 8 represents a separate measurement at a different, nearby insertion site. The force of insertion 82 (lb) is plotted against the distance or depth of insertion 84 (inches). As shown in FIG. 8, the force of insertion 82 is substantially constant with only modest increases beyond a depth 84 of about 0.1 inches (2.5 mm), even when the insertion depth 84 is about 0.3 inches (7.6 mm). By inserting sharp 100 in a direction perpendicular to the tissue surface, inserter set 190 can deposit continuous monitoring sensor 120 into the critical subcutaneous layer with minimal trauma to the tissue. The typical insertion depth during use is from 4 mm to 7 mm for accurate measurement of subcutaneous glucose. Other inserter designs insert a sharp at angles of about 45 degrees (more or less) thus increasing length of insertion by 41%. Work energy (force times distance; the area under a curve 86) has been shown to be proportional to the incidence of pain response reported by users.

To further reduce or minimize the pain of insertion, sharps 100 of the present invention are used in an inserter assembly 200 that deploys continuous monitoring sensor 120 into skin tissue. Introducer designs that rely on the patient to drive sharp 100 into the patient's own tissue greatly benefit the patient by providing low-force and low-work designs. This benefit derives from psychological reasons as well as from the practical aspect of having to insert a sharp into a relatively soft abdomen or hip.

Figure 9:
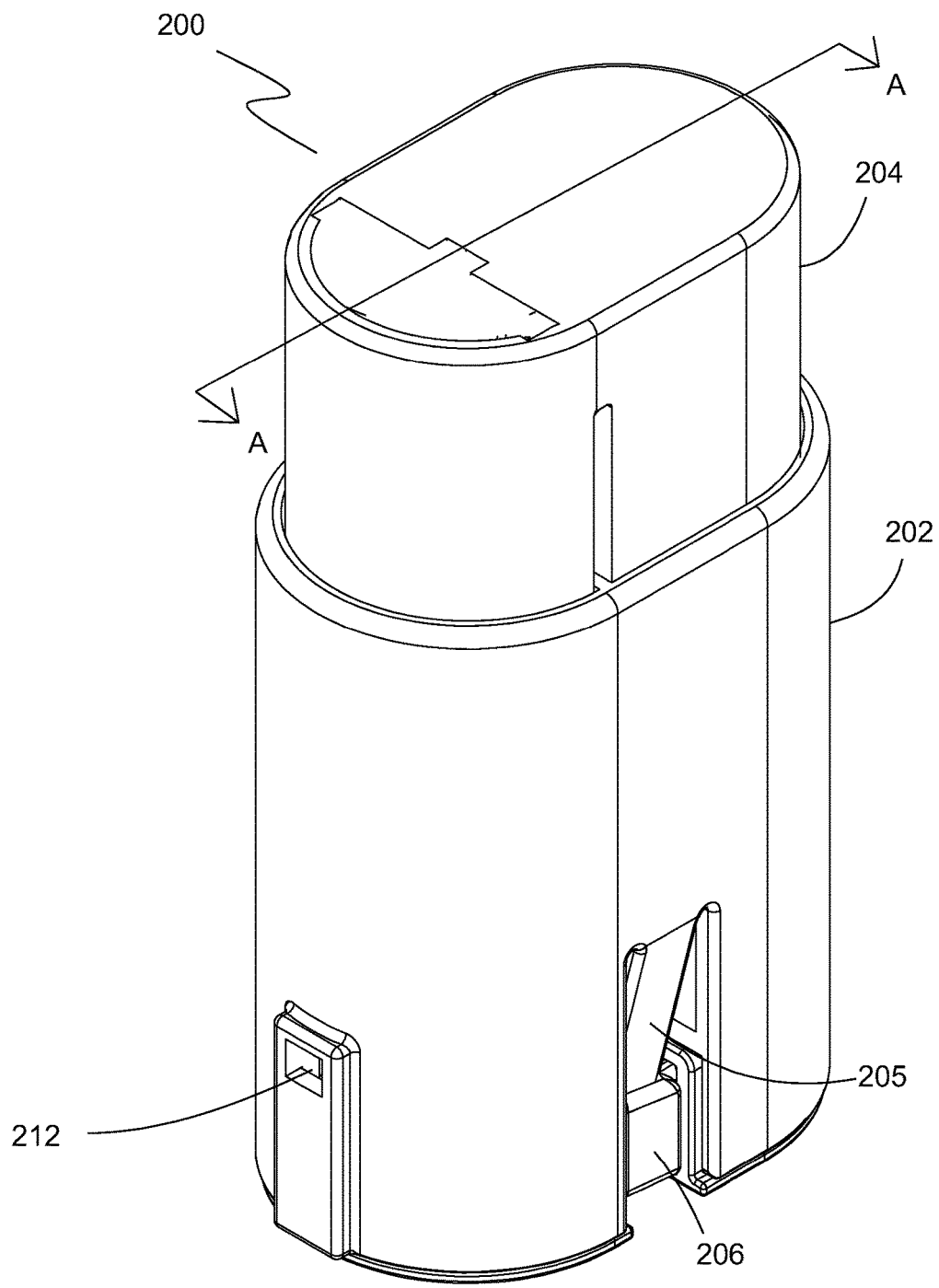
FIG. 9 is a perspective view of one embodiment of an inserter assembly of the present invention showing the top, end, and side surfaces.

Referring now to FIG. 9, a perspective view shows one embodiment of an inserter assembly 200 of the present invention that includes a housing body 202 and a deployment button 204 slidably received in housing body 202. A sensor housing 206 is removably attachable to housing body 202. Housing body 202, sensor housing 206, and deployment button 204 are collectively referred to herein as a deployment assembly 1000. A deployment mechanism 208 (shown in FIG. 10) is operable with deployment button 204, housing body 202, and sensor housing 206. Housing body 202 includes one or more recesses 212 for engagement with deployment button 204 as is discussed in more detail below with reference to FIG. 10. Housing body 202 also includes a locking mechanism 205 (e.g., resilient tab, clip, protrusion, etc.) that engages sensor housing 206 and retains it together with the inserter assembly 200 forming the deployment assembly 1000. Locking mechanism 205 is discussed in more detail below.

Figure 10:
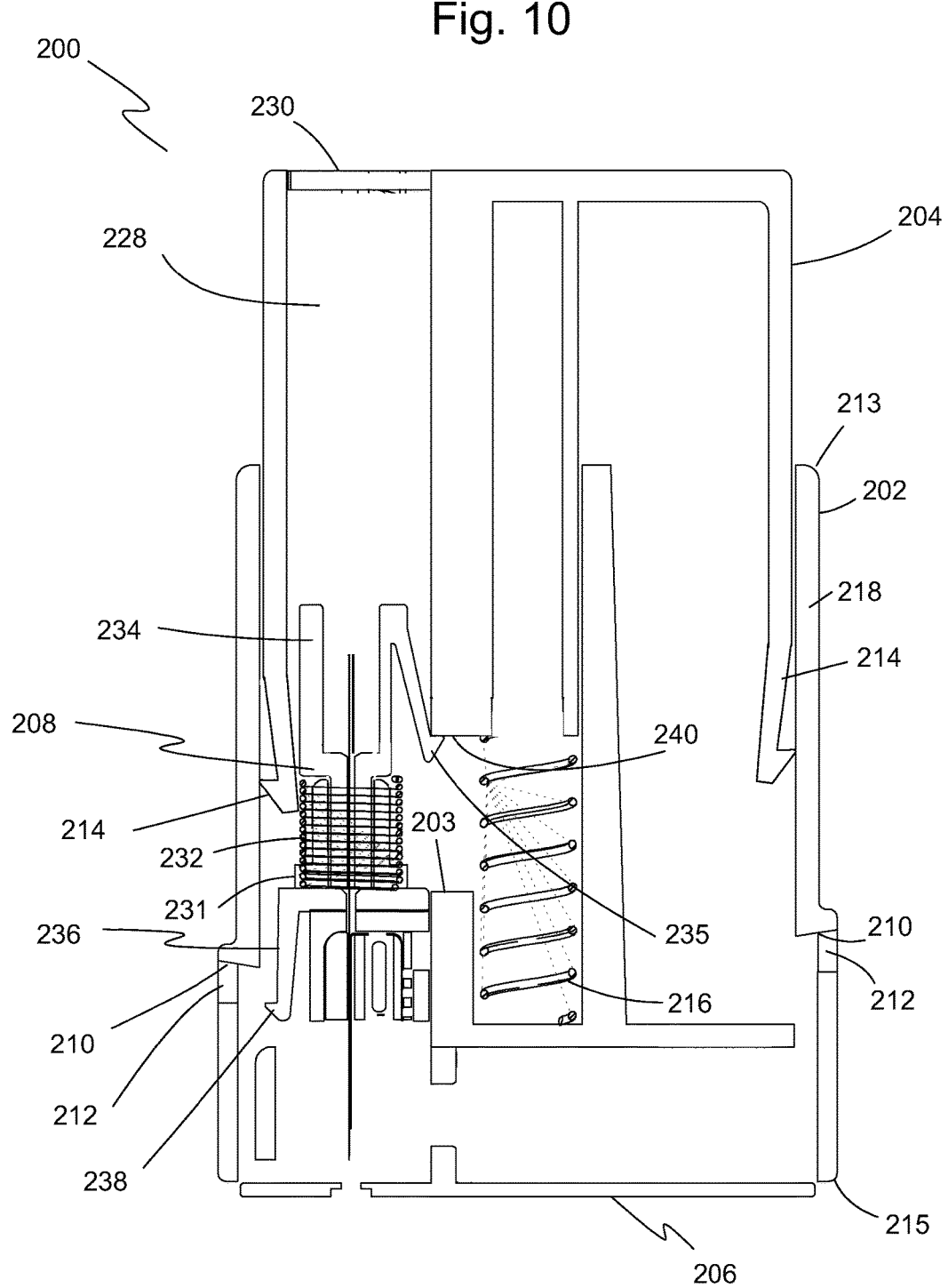
FIG. 10 is a side, cross-sectional view of the inserter assembly of FIG. 9 as taken along line A-A with the button and deployment mechanism in respective first or up positions.

FIG. 10 shows a side, cross-sectional view of inserter assembly 200 taken along line A-A of FIG. 9. Housing body 202 has a first body end 213 and a second body end 215 with deployment button 204 at least partially disposed in and slidable within housing body 202 through first body end 213. Housing body 202 includes at least one first catch surface 210 defined by a recess 212, opening, ledge, protrusion, or other structure. First catch surface 210 is constructed and sized to engage a corresponding resilient locking catch 214 on deployment button 204 when a user presses deployment button 204 into housing body 202 from a first or ready position (shown in FIG. 10) to a second or inserted position (shown in FIG. 11). One or more springs 216 (e.g., coil spring) disposed between deployment button 204 and housing body 202 bias deployment button 204 towards the first or ready position as shown in FIG. 10. When deployment button 204 is in the first (ready position), locking catch 214 is held inward in tension by abutment with housing wall 218. When the user presses deployment button 204 down, the tension on locking catch 214 causes locking catch 214 to move outward towards its resting, non-tensioned/non-compressed position to engage first catch surface 210. Of course, housing body 202 and deployment button 204 can be configured so that first catch surface 210 is on deployment button 204 and locking catch 214 is on housing body 202. Other releasable locking mechanisms known in the art are also acceptable. In one embodiment, inserter assembly 200 includes at least two first catch surfaces 210 and corresponding locking catches 214 as shown in FIG. 10.

Deployment mechanism 208 is slidably received in a deployment mechanism cavity 228 in deployment button 204. A deployment cap 230 closes mechanism cavity 228 and can be removed for access to deployment mechanism 208. Deployment mechanism 208 includes a deployment spring 232, a needle/sharp carrier 234 with a needle carrier catch 235, and a sensor deployment assembly 236 with a resilient deployment catch 238. Deployment spring 232 (e.g., a coil spring) is disposed between spring support component 231 and needle carrier 234 in a tensioned orientation. Needle carrier catch 235 prevents needle carrier 234 from being moved towards deployment cap 230 by deployment spring 232. When the user presses deployment button 204, needle carrier catch 235 is released from button catch surface 240 by carrier release surface 203 of housing body 202 and deployment spring 232 then biases needle carrier 234 towards a deployment cap 230.

Figure 11:
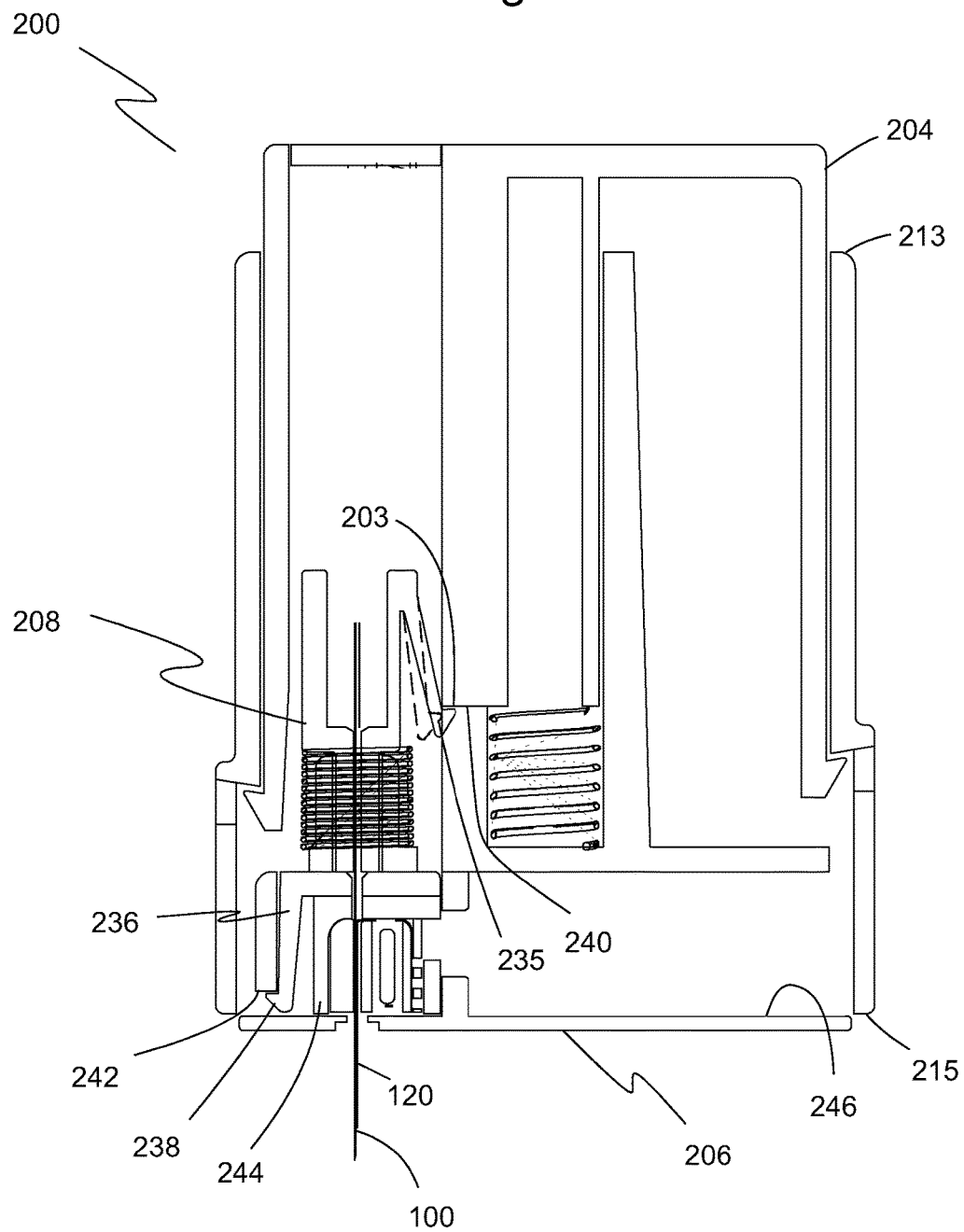
FIG. 11 is a side, cross-sectional view of the inserter assembly of FIG. 10 shown with the button and deployment mechanism in a second or down position.

Referring now to FIG. 11, a side, cross-sectional view of inserter assembly 200 is shown with deployment button 204 and deployment mechanism 208 in their respective second positions (needle inserted positions). When the user presses button 204, deployment mechanism 208 moves downward towards sensor housing 206 due to engagement between a button catch surface 240 and carrier catch 235. At the end of travel for deployment button 204, a deployment guide 244 abuts a floor 246 or other structure of sensor housing 206 to stop the travel of deployment button 204 and of deployment mechanism 208. In its second carrier position (inserted position), sensor deployment assembly 236 is positioned within sensor housing 206 and deployment body catch 238 engages base catch surface 242. In the second carrier position, the deployed continuous monitoring sensor 120 is retained by sensor housing 206 and is positioned for electrical communication with electronic module 300 (internal electrical/electronic components not shown for clarity) attached to sensor housing 206. Simultaneously with retention of continuous monitoring sensor 120 in sensor housing 206, carrier catch 235 contacts carrier release surface 203. This causes carrier catch 235 to move to a second carrier catch orientation as shown by the dashed outline of carrier catch 235 and to disengage from button catch surface 240 with an audible "click" thereby allowing deployment spring 232 to automatically return carrier assembly 208 to a third carrier position (up position) with sharp 100.

Figure 12:
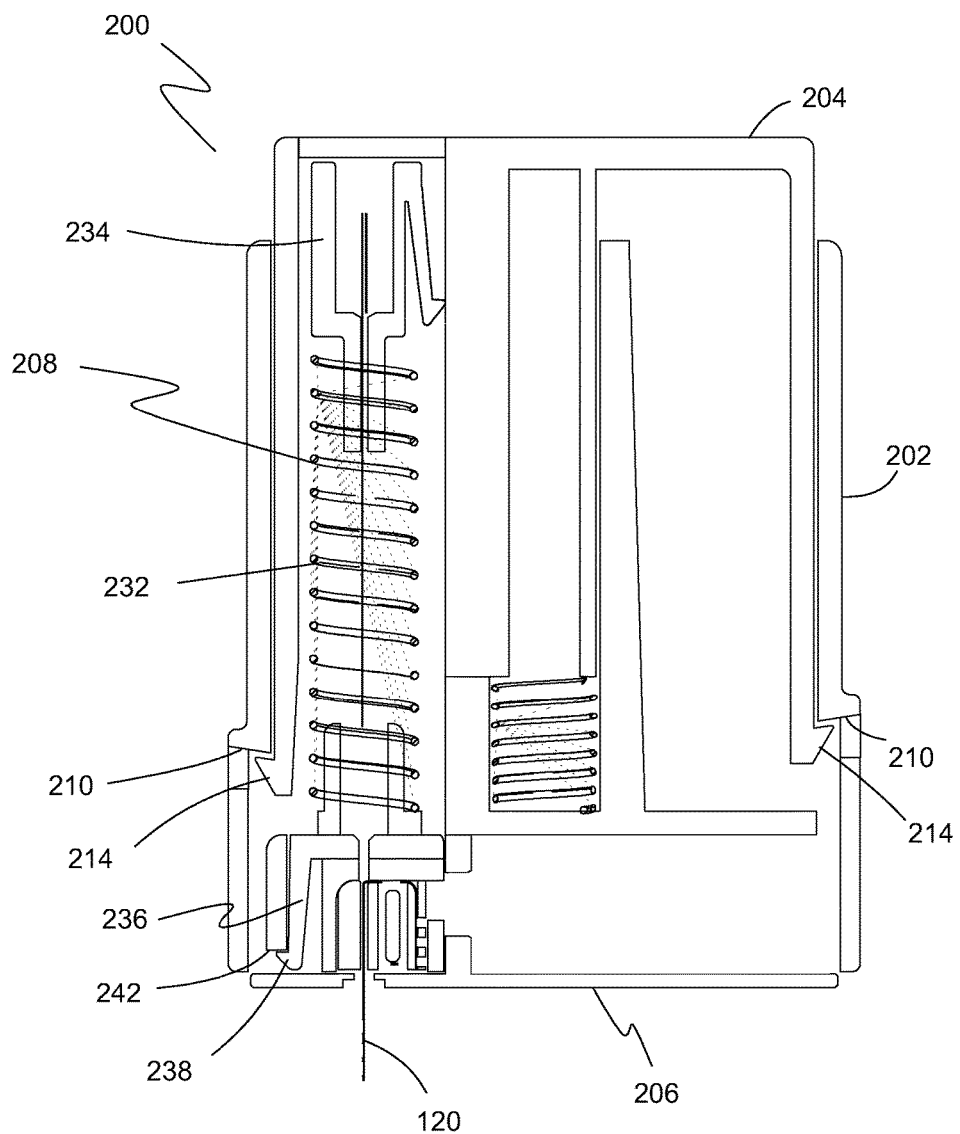
FIG. 12 is a side, cross-sectional view of the inserter assembly of FIG. 10 shown with the button in the second position and the deployment mechanism in a retracted position.

FIG. 12 shows a side, cross-sectional view of inserter assembly 200 with deployment button 204 in its second position (down position), sensor 120 deployed, and deployment mechanism 208 having returned to its third carrier position (up or retracted position). Deployment body catch 238 remains engaged with base catch surface 242 to maintain sensor deployment assembly 236 engaged with sensor housing 206. Locking catch(es) 214 also remain engaged with first catch surface(s) 210 to maintain button 204 in its second position. With continuous monitoring sensor 120 now deployed, housing body 202 with deployment button 204 and deployment mechanism 208 (aka the deployment assembly) may be disengaged from sensor housing 206 and removed, leaving sensor housing 206 in place on the patient for continuous glucose monitoring. It is important to note that, even though the cross-sectional shape, insertion angle, and sharpness of the insertion needle are aspects of the invention that reduce the amount of perceived pain experienced by the user upon insertion, the described single-action feature of the present invention is another aspect of the invention that also reduces the amount of pain the user perceives upon insertion even when other needles in the prior art are used such as, for example, needles having larger cross-sectional diameters and higher insertion peak forces.

Figure 13:
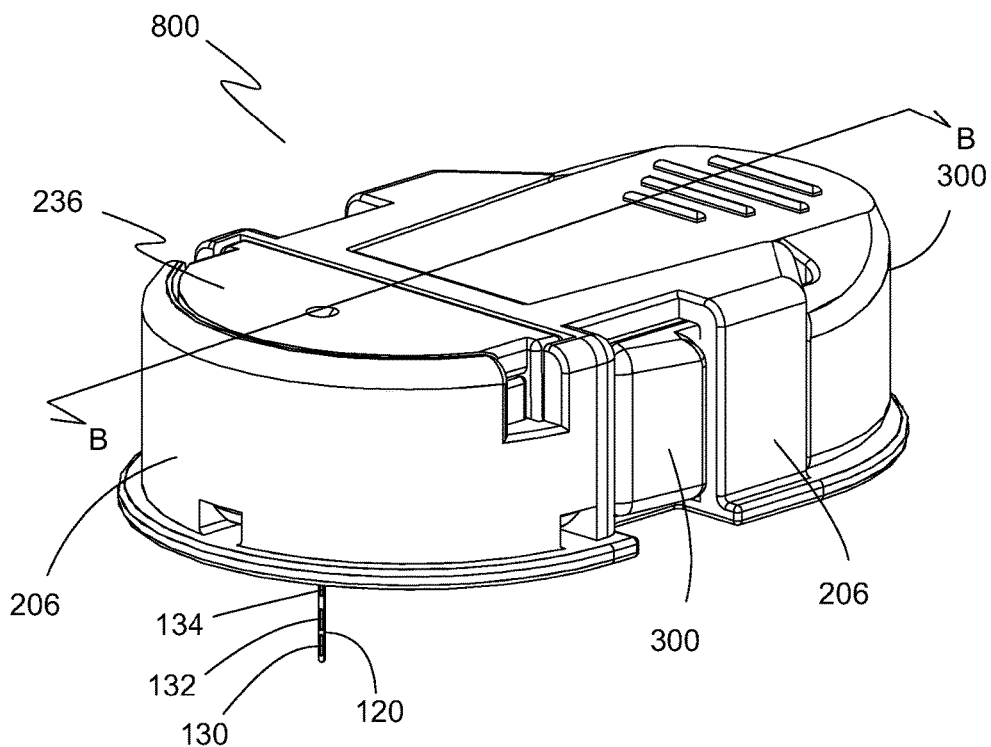
FIG. 13 is a side and top perspective view of one embodiment of a sensor housing assembly of the present invention.
Figure 14:
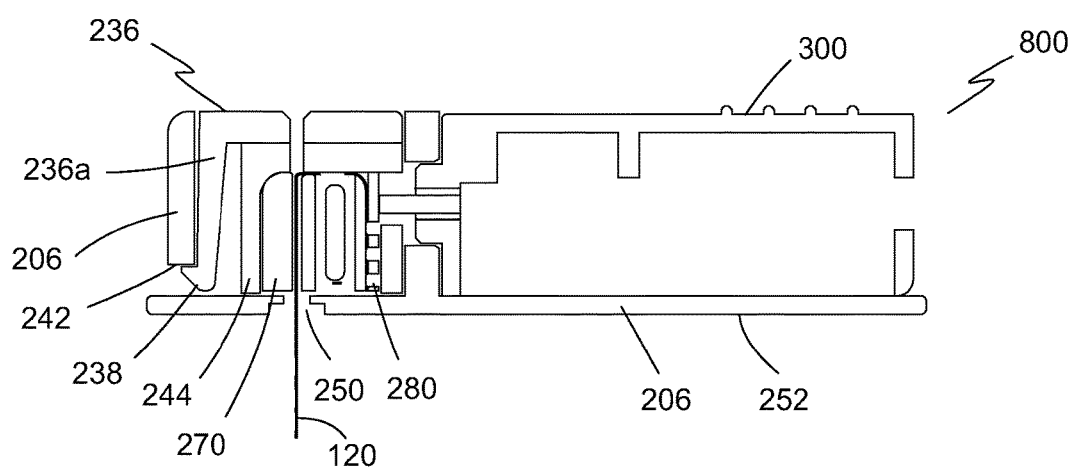
FIG. 14 is a side, cross-sectional view of the sensor housing assembly of FIG. 13 as taken along line B-B of FIG. 13.

Referring now to FIG. 13, a top perspective view shows an embodiment of sensor housing assembly 800 separate from inserter assembly 200. Also shown attached to sensor housing 206 is electronic module 300. Electronic module 300 is removably attachable to sensor housing 206 and, thus, re-usable with other inserter assembly 200. Continuous monitoring sensor 120 is shown in wireframe in order to show the relative positions of working electrode 130, counter electrode 132, and reference electrode 134 since electrodes 130, 132, 134 are on the hidden side of sensor 120 in this view. FIG. 14 shows a side cross-sectional view of sensor housing assembly 800 as taken along line B-B of FIG. 13. Sensor deployment assembly 236 remains with sensor housing 206 due to continued engagement between deployment body catch 238 and base catch surface 242. Sensor deployment assembly 236 includes a deployment body 236a, deployment guide 244, a sensor carrier 270, and a sensor board 280. Continuous monitoring sensor 120 extends through a sensor opening 250 in bottom 252 of sensor housing 206 when implanted subcutaneously in a patient. Working electrode 130, counter electrode 132, and reference electrode 134 (shown in FIG. 13) are electrically coupled to electrical components (not shown) disposed in or a part of electronic module 300, which electrical components are configured to read, transmit, display, and/or record glucose measurements. Although a glucose sensor is described and used in this embodiment, it is contemplated that other analytes may be similarly measured using the present invention and would involve substituting the glucose sensor with an appropriate analyte sensor for the analyte to be measured.

Turning now to FIGS. 15 and 16, there are illustrated enlarged views of one embodiment of the sensor carrier 270 and sensor 120. Sensor carrier 270 has a sensor/needle bore 272 that receives sharp 100 and sensor 120, a sensor anchor space 274 with a sensor wrap bar 275 and sensor groove 276 formed in a carrier board-receiving surface 278. As shown, sensor 120 wraps around sensor wrap bar 275 in sensor anchor space 274. Sensor proximal portion 120a, which has a plurality of contact pads 121 for electrically coupling electrodes 130, 132 and 134 to measuring electronics, is disposed within sensor groove 276. It is the flexibility of sensor 120 that permits such an orientation (i.e. wrapping)

without damaging the electrical conduits embedded within sensor 120 that electrically couple electrodes 130, 132, 134 to contact pads 121. FIGS. 17 and 18 illustrate only sensor 120 enlarged to show the bent orientation of sensor 120 when mounted in sensor carrier 270. It is contemplated that sensor 120 may have a length that is shorter where wrapping the sensor is not required and, in fact, the looping of the sensor 120 around wrap bar 275 is unnecessary. Sensor 120 could be secured to sensor carrier 270 using other known techniques so long as the sensor proximal portion 120*a* is either disposed within sensor groove 276 or configured to position the plurality of contact pads 121 for electrically coupling electrodes 130, 132 and 134 to measuring electronics.

Figure 19:
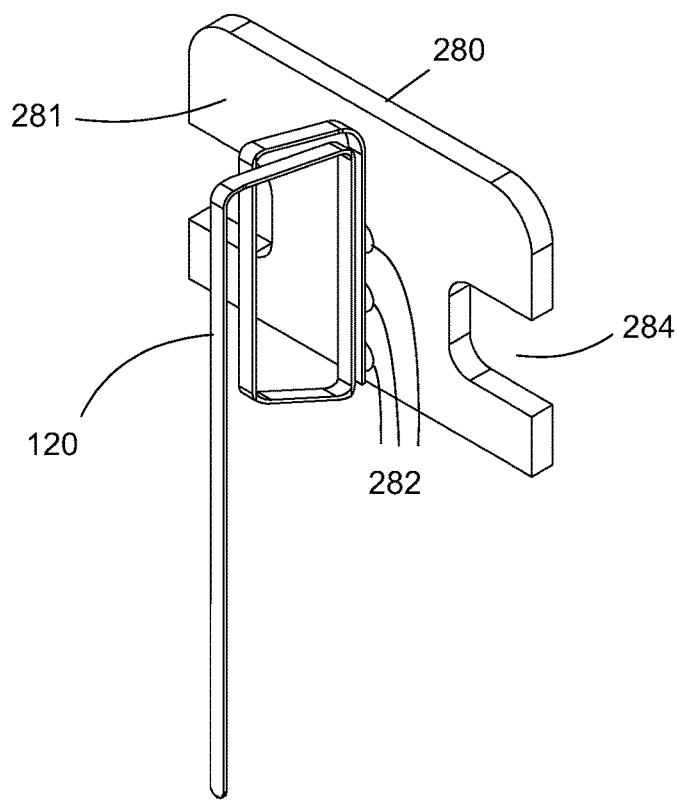
FIG. 19 is an enlarged perspective view of the back side of the sensor and sensor board.
Figure 20:
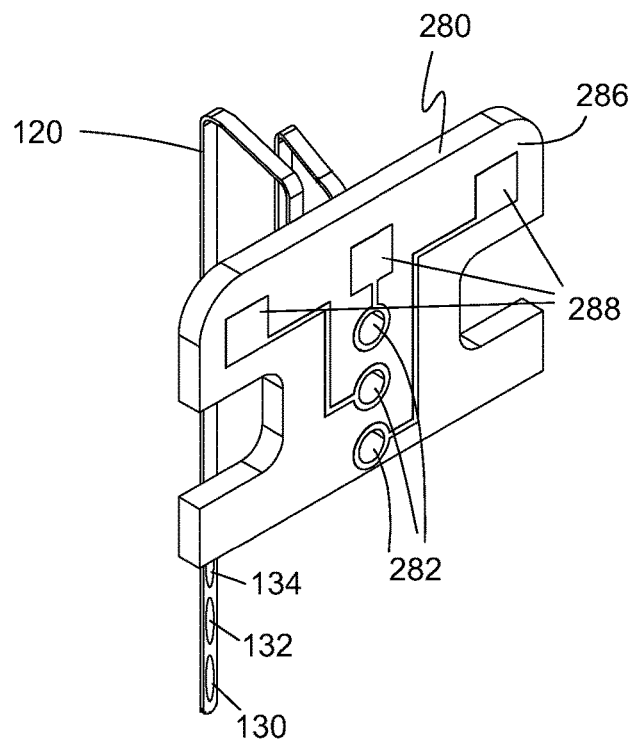
FIG. 20 is an enlarged perspective view of the front side of the sensor and sensor board.

FIGS. 19 and 20 illustrate enlarged views of sensor 120 and sensor board 280. Sensor board 280 has one or more board notches 284 configured to attach to/mate with carrier board-receiving surface 278 of sensor carrier 270 (See FIG. 16), and a sensor side 281. Sensor side 281 includes electrical coupling elements 282 that are electrically coupled to sensor contact pads 121 and therefore to electrodes 130, 132 and 134. Sensor board 280 also has component module housing side 286 with a plurality of electronic coupling pads 288.

FIGS. 21 and 22 illustrate perspective and side views, respectively, of sensor 120, coupled to sensor board 280 and electronic module 300. Electronic module 300 has at least one module housing arm 304 for removable attachment to mating receptacles in sensor housing 206. Extending from an electrical coupling side 306 is a plurality of electrical coupling elements 308 that align and electrically couple with the plurality of electronic coupling pads 288 of sensor board 280. Electronic module 300 contains all of the electrical components required to enable sensor 120 to work as well as to provide the means for reading, transmitting, displaying, and/or recording glucose and/or other analyte measurements.

In one embodiment, sensor housing 206 has a very compact form factor measuring 1.5 inches (7.1 mm) long by 1.0 (25.4 mm) wide by 0.3 (7.6 mm) high that is very small and convenient to the patient.

Continuous Monitoring System with Lumen

Figure 23:
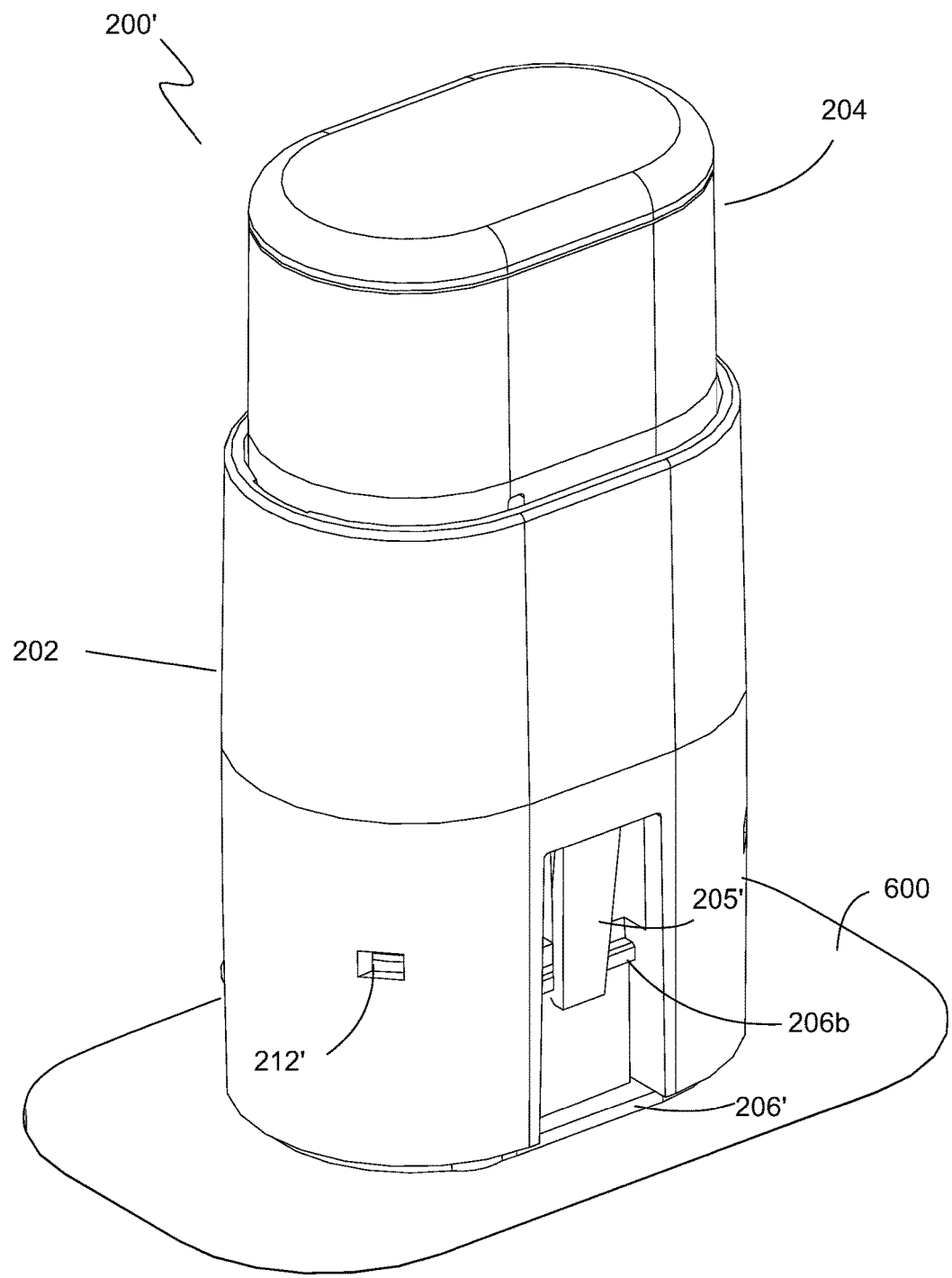
FIG. 23 is a perspective view of another embodiment of an inserter assembly of the present invention.

FIG. 23 illustrates another embodiment of an inserter assembly 200' for a continuous monitoring system. Like the embodiment shown in FIG. 9, an inserter assembly 200' includes a housing body 202, a deployment button 204 slidably received in housing body 202, and a sensor housing 206' that is removably attachable to housing body 202. As previously disclosed, housing body 202, sensor housing 206', and deployment button 204 are collectively referred to herein as a deployment assembly 1000. Housing body 202 includes one or more recesses 212' for engagement with deployment button 204 and also includes a locking mechanism 205' (e.g., resilient tab, clip, protrusion, etc.) that engages sensor housing 206' and retains it together with the deployment assembly 1000. Locking mechanism 205' functions in the same way as previously discussed with respect to inserter assembly 200 except for the position of the locking mechanism relative to the housing body 202 and deployment button 204. The main difference between the embodiment illustrated in FIG. 23 and the embodiment in FIG. 9 is the position of recesses 212' in housing body 202 and of locking mechanism 205'. Recesses 212' in FIG. 23 are offset from a transverse axis of housing body 202, which allows for incorporation of two needle carrier catches 235 (shown in FIGS. 31-33). Locking mechanism 205' is positioned to latch and hold sensor housing 206' at a housing outside catch surface 206*b* whereas locking mechanism 205' is positioned to latch and hold sensor housing 206' at a housing inside catch surface 206*a*. In both embodiments, locking mechanism 205, 205' release sensor housing 206, 206' (respectively) when the sensor is deployed. Also shown in FIG. 23 is an adhesive component 600 that is attached to the bottom of the sensor housing 206' and secures sensor housing 206' to the patient upon deployment of the continuous monitoring system.

Turning now to FIG. 24, there is illustrated a cross-sectional view of sensor housing 206' containing a sensor deployment assembly 236 with a lumen 900 and the electronic module 300'. FIG. 24A is an enlarged view of area M shown in FIG. 24. Sensor deployment assembly 236 remains with sensor housing 206' due to continued engagement between deployment body catch 238 and base catch surface 242. Sensor deployment assembly 236 includes a deployment body 236*a*, deployment guide 244, a sensor carrier 270*a* with a single lumen tube 973 fixedly attached to sensor carrier 270*a*, and a sensor board 280. Continuous monitoring sensor 120 and single lumen tube 973 extend through a sensor opening 250 in bottom 252 of sensor housing 206'. Sensor opening 250 has a sensor opening grommet 251 to center sensor carrier 270*a* and provides a moisture resistant seal between sensor opening 250 of sensor housing 206', lumen tube 973, and sensor carrier 270*a*. Grommet 251 is swaged down by the compression of the elastic material of deployment guide 244 and sensor carrier 270*a*, thus forming a compression tight seal between sensor opening 250 and sensor housing 206'. Also shown deployed onto sensor deployment assembly 236 is a medication delivery assembly 400, which is discussed in greater detail below. Working electrode 130, counter electrode 132, and reference electrode 134 of an electrode system 135 (shown in FIG. 24B) are electrically coupled to electrical components (not shown) disposed in or a part of electronic module 300', which electrical components are configured to receive and transmit electrical signals generated by electrode system 135. Although a glucose sensor is described and used in this embodiment, it is contemplated that other analytes may be similarly measured using the present invention and would involve substituting the glucose sensor with an appropriate analyte sensor for the analyte to be measured.

FIGS. 24B and 24C illustrate enlarged views of sensor carrier 270*a* and sensor 120. Sensor carrier 270*a* has a sensor/needle bore 272, single lumen 973 that receives sharp 100 (shown in FIGS. 31-32) and sensor 120, and a sensor groove 276 formed in a carrier top 271*a* and in carrier board-receiving surface 278. As shown, sensor 120 bends around sensor carrier 270*a* from a top of needle bore 272 and extends into sensor groove 276. Sensor proximal portion 120*a*, which has a plurality of contact pads 121 for electrically coupling electrodes 130, 132 and 134 to measuring electronics placed within electronic module 300', is disposed within sensor groove 276. It is the flexibility of sensor 120 that permits such an orientation (i.e. bending) without damaging the electrical conduits embedded within sensor 120 that electrically couple electrodes 130, 132, 134 to contact pads 121. Sensor 120 is secured to sensor carrier 270*a* using known techniques so long as the sensor proximal portion 120*a* is either disposed within sensor groove 276 or configured to position the plurality of contact pads 121 for electrically coupling electrodes 130, 132 and 134 to measuring electronics.

FIG. 24D illustrates an enlarged cross-sectional view of sensor carrier 270*a* along line C-C. At a carrier bottom surface 271, there is formed a grommet receiving recess 275 that surrounds a carrier bottom protrusion 275a that extends beyond carrier bottom surface 271 and has needle bore 272 therethrough. Grommet receiving recess 275 and carrier bottom protrusion 275a have tapered sides to better create a moisture-resistant seal with grommet 251. FIG. 24E illustrates a bottom view of the sensor carrier 270a showing grommet receiving recess 275 as circular, but recess 275 may have any other form.

Figure 25:
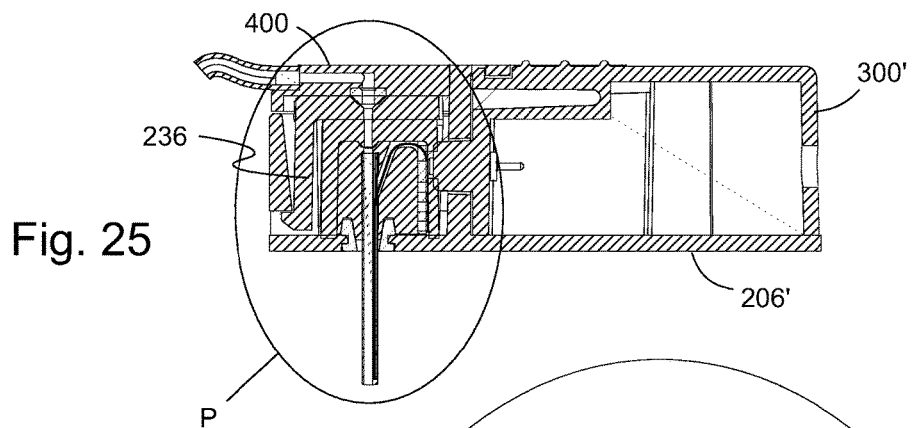
FIG. 25 is a sectional view of a sensor carrier with sensor and a dual lumen configuration.
Figure 25A:
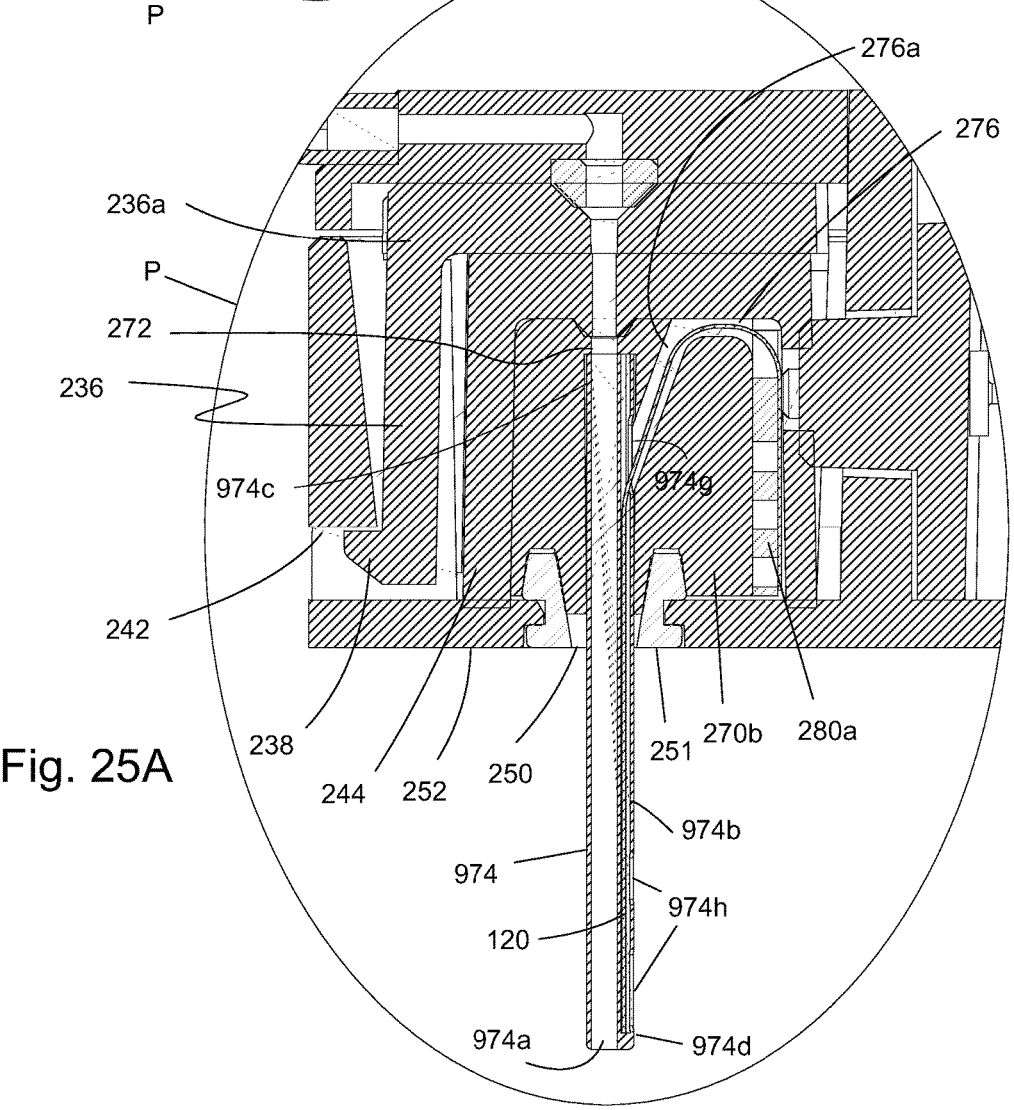
FIG. 25A is an enlarged view of the sensor carrier with the sensor and the dual lumen configuration shown in FIG. 25.

Turning now to FIG. 25, there is illustrated a cross-sectional view of sensor housing 206' containing a sensor deployment assembly 236 with a dual lumen and the electronic module 300'. FIG. 25A is an enlarged view of area P shown in FIG. 25. Sensor deployment assembly 236 remains with sensor housing 206' due to continued engagement between deployment body catch 238 and base catch surface 242. Sensor deployment assembly 236 includes a deployment body 236a, deployment guide 244, a sensor carrier 270b with a dual/double lumen tube 974 fixedly attached to sensor carrier 270b, and a sensor board 280a. Continuous monitoring sensor 120 and double lumen tube 974 extend through a sensor opening 250 in bottom 252 of sensor housing 206'. Sensor opening 250 has a sensor opening grommet 251 to center sensor carrier 270b and provides a moisture resistant seal between sensor opening 250 of sensor housing 206', lumen tube 974, and sensor carrier 270b. Grommet 251 is swaged down by the compression of the elastic material of deployment guide 244 and sensor carrier 270b, thus, forming a compression tight seal between sensor opening 250 and sensor housing 206'. As can be seen in FIG. 25A, double lumen tube 974 has first lumen tube 974a for the sharp/needle 100 and a second lumen tube 974b for sensor 120. Second lumen tube 974b has a second lumen side opening 974g adjacent an upper lumen end 974c that communicates with a sensor bore 276a that communicates at a transverse angle with needle bore 272 and with sensor groove 276. Adjacent a lower lumen end 974d are one or more second lumen electrode openings 974h, which expose electrode system 135 (shown in FIG. 24B) on sensor 120 to a sample to be measured. Also shown deployed onto sensor deployment assembly 236 is a medication delivery assembly 400. Working electrode 130, counter electrode 132, and reference electrode 134 of an electrode system 135 (shown in FIGS. 25C and 25E) are electrically coupled to electrical components (not shown) disposed in or a part of electronic module 300', which electrical components are configured to receive and transmit electrical signals generated by electrode system 135.

Figure 25B:
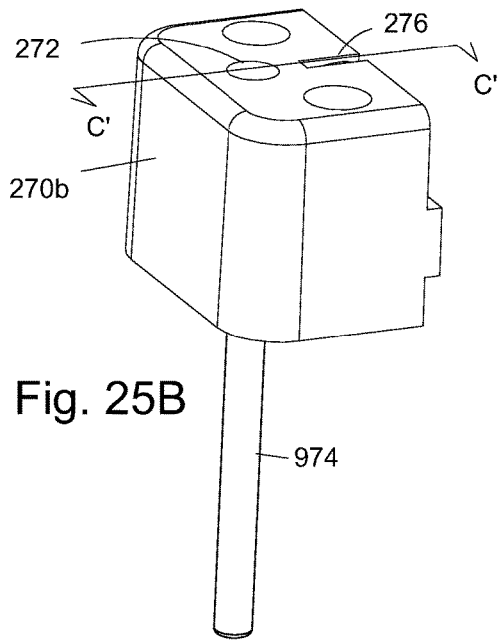
FIG. 25B is an enlarged perspective view of another embodiment of a sensor carrier with sensor and single lumen showing the back side of the sensor carrier.
Figure 25C:
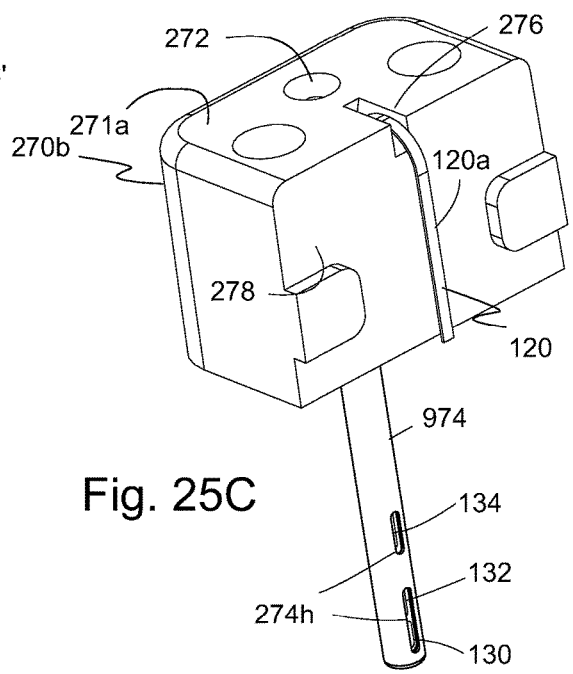
FIG. 25C is an enlarged perspective view of the sensor carrier with sensor and single lumen showing the front side of the sensor and the proximal end portion of the sensor shown in FIG. 25B.

FIGS. 25B and 25C illustrate enlarged views of another embodiment of sensor carrier 270b and sensor 120. Sensor carrier 270b has a sensor/needle bore 272, dual/double lumen tube 974 that receives sharp 100 and sensor 120, and a sensor groove 276 formed in carrier top 271a but not in carrier board-receiving surface 278. As shown, sensor 120 bends around sensor carrier 270b from needle bore 272 at the junction of sensor bore 276a up to sensor groove 276 in carrier top 271a and across from and in spaced relationship with carrier board-receiving surface 278. Sensor proximal portion 120a has a plurality of contact pads 121 for electrically coupling electrodes 130, 132 and 134 to measuring electronics, where contact pads 121 face carrier board-receiving surface 278. It is the flexibility of sensor 120 that permits such an orientation (i.e. bending) without damaging the electrical conduits embedded within sensor 120 that electrically couple electrodes 130, 132, 134 to contact pads 121. Sensor 120 is secured to sensor carrier 270b using known techniques so long as the sensor proximal portion 120a is either disposed against sensor board 280 or configured to position the plurality of contact pads 121 for electrically coupling electrodes 130, 132 and 134 to measuring electronics.

Figure 25D:
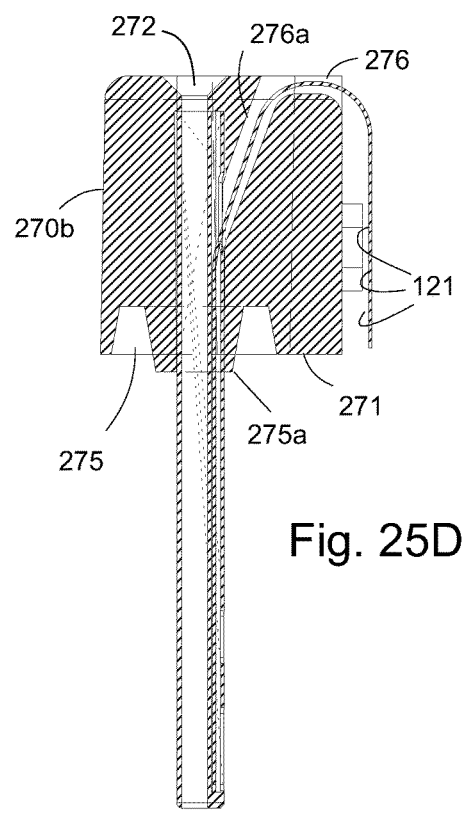
FIG. 25D is an enlarged cross-sectional view of the sensor carrier shown in FIG. 25B.

FIG. 25D illustrates an enlarged cross-sectional view of sensor carrier 270b along line C'-C'. At a carrier bottom surface 271, there is formed a grommet receiving recess 275 that surrounds a carrier bottom protrusion 275a that extends beyond carrier bottom 271 and has needle bore 272 therethrough. Grommet receiving recess 275 and carrier bottom protrusion 275a each have tapered sides to better create a moisture-resistant seal with grommet 251.

Figure 25E:
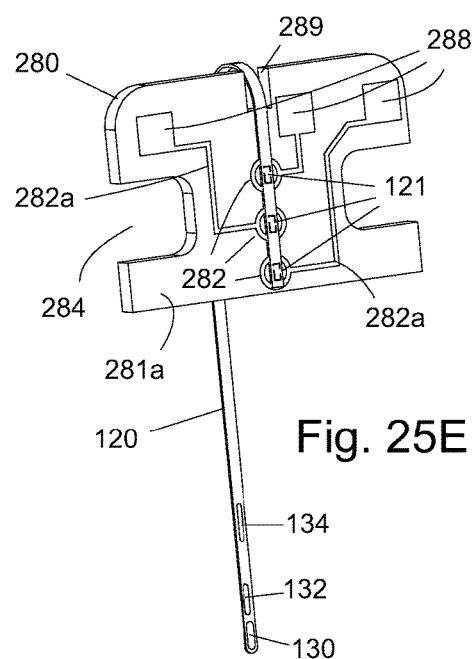
FIG. 25E is an enlarged perspective view of the back side of the sensor and sensor board.

FIG. 25E illustrates a rear perspective view of sensor board 280 and sensor 120. Sensor board 280 has one or more board notches 284 configured to mate with carrier board-receiving surface 278 of sensor carrier 270b. In the dual/double lumen arrangement, sensor board has a top board notch 289 to accommodate the bend of sensor 120 for positioning sensor proximal end 120a against an outer sensor side 281a of sensor board 280 for coupling sensor contact pads 121 of sensor 120 to the electrical coupling elements 282 that electrically connect to traces 282a which, in turn, are electrically coupled to a plurality of electronic coupling pads 288. As is evident from the figures, the reason for this arrangement of the contact pads 121 of sensor 120 facing the outer sensor side 281a of sensor board 280 is that the dual lumen 974 requires that electrode system 135 face toward the sensor board 280 causing the contact pads to face toward the lumen wall; unlike the single lumen configuration where the electrode system 135 faces away from sensor board 280. Also in this double lumen embodiment, the middle electrical coupling pad 288 is offset from the center because of sensor proximal portion 120a needing to contact the outer sensor side 281a of sensor board 280 and because sensor proximal portion would interfere with the electrical contact between middle electrical coupling pad 288 and the corresponding electrical contact of the electronic module 300'.

Figure 26:
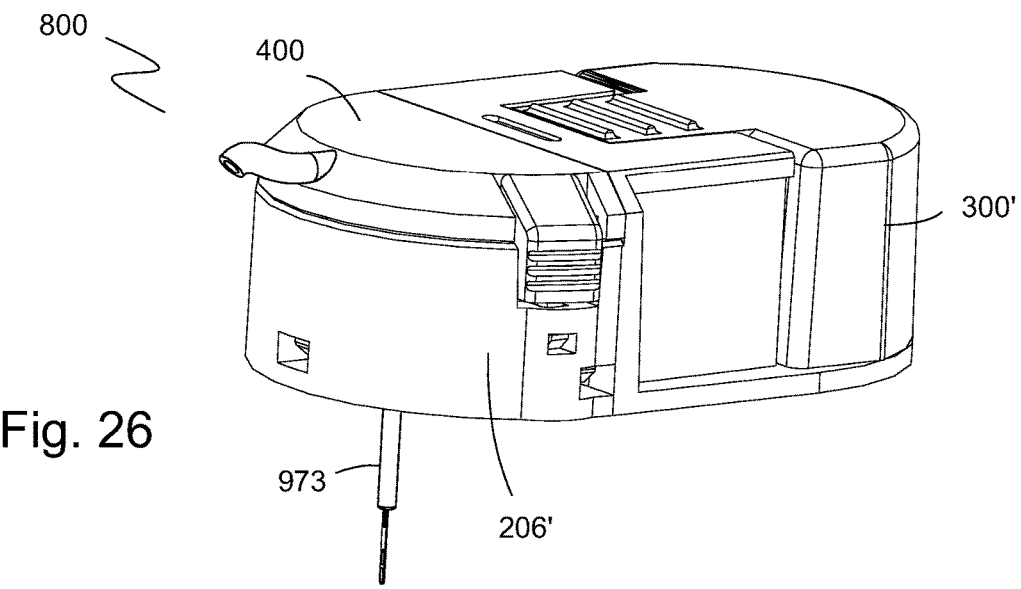
FIG. 26 is a perspective view of the sensor housing assembly with the single lumen showing a medication delivery assembly for mating to the lumen in the sensor carrier.
Figure 27:
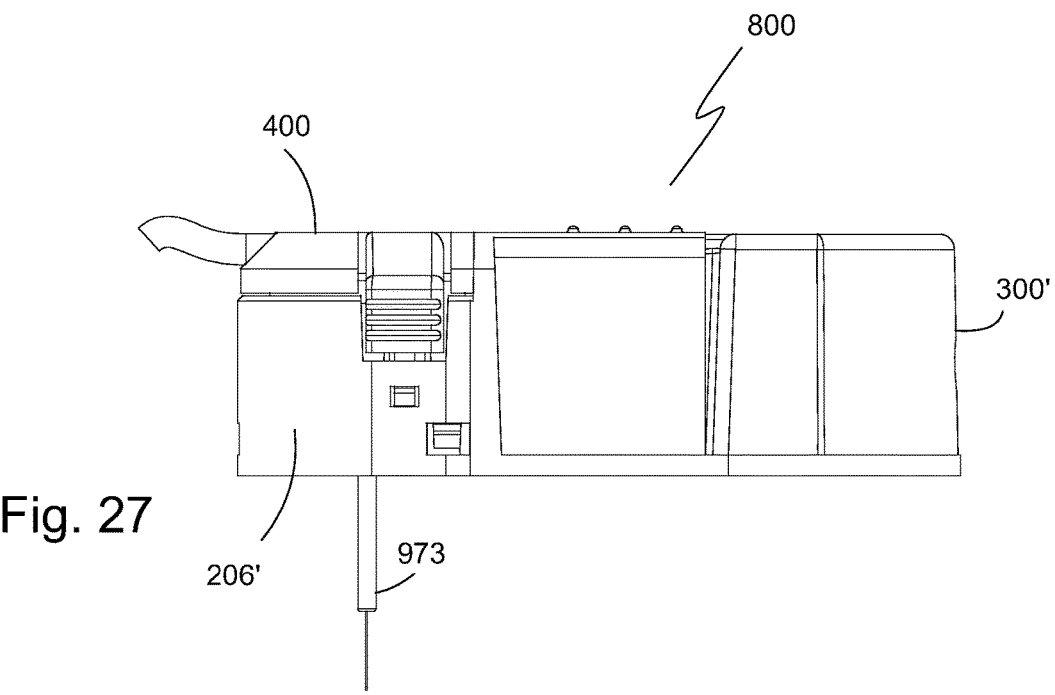
FIG. 27 is a side elevation view of the sensor housing assembly of FIG. 26.
Figure 28:
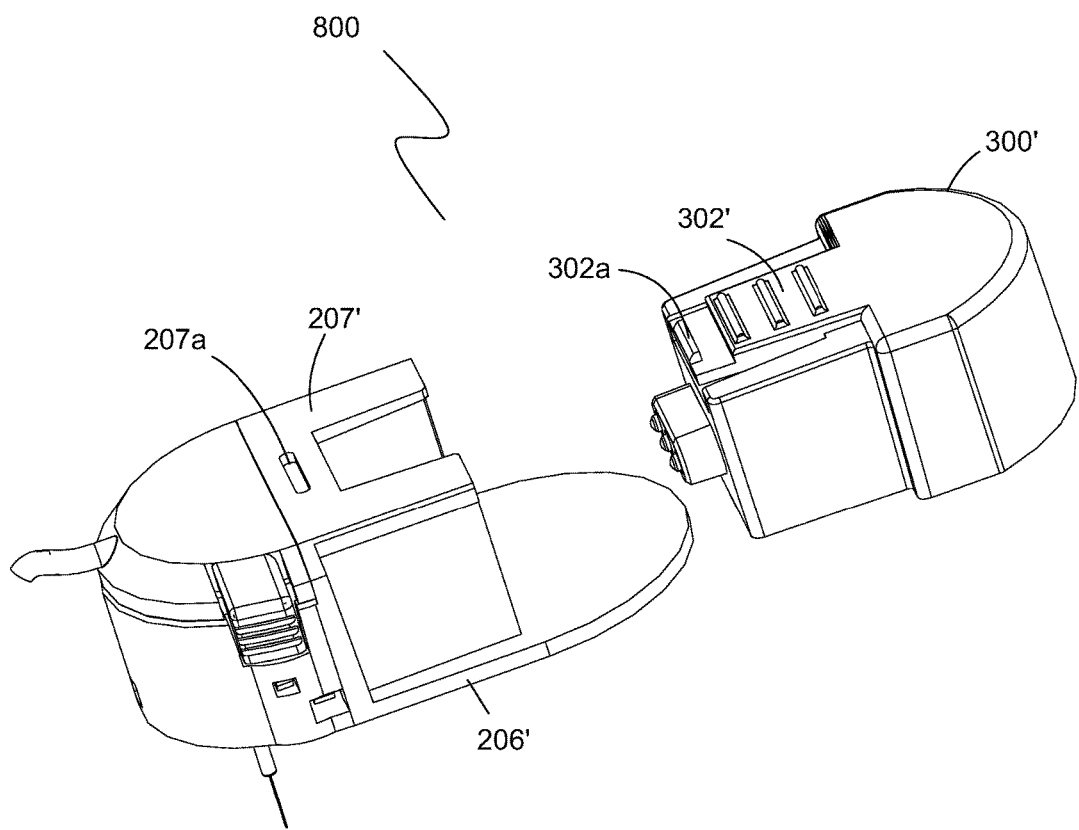
FIG. 28 is a partially exploded, perspective view of the sensor housing assembly of FIG. 26 with the single lumen and showing the electronic module decoupled from the sensor housing.

Turning now to FIGS. 26, 27 and 28, there are illustrated perspective, side and expanded views of the sensor housing assembly 800. As seen in FIGS. 26 and 27, sensor housing assembly 800 includes sensor housing 206', electronic module 300' releasably attached to sensor housing 206' and medication delivery assembly 400 releasably attached to the top of sensor deployment assembly 236 that is captured within sensor housing 206'. In the embodiment illustrated, sensor carrier 270a (shown in FIG. 24) has a single lumen tube 973. FIG. 28 illustrates the difference in how electronic module 300' mechanically couples to sensor housing 206' compared to the embodiment shown in FIG. 21. Component housing 300' has a top resilient tab 302' that has a tab catch 302a that mates with a tab catch slot 207a in a top 207' of sensor housing 206' whereas component housing 300 illustrated in FIG. 21 has side resilient tabs 304.

Figure 29:
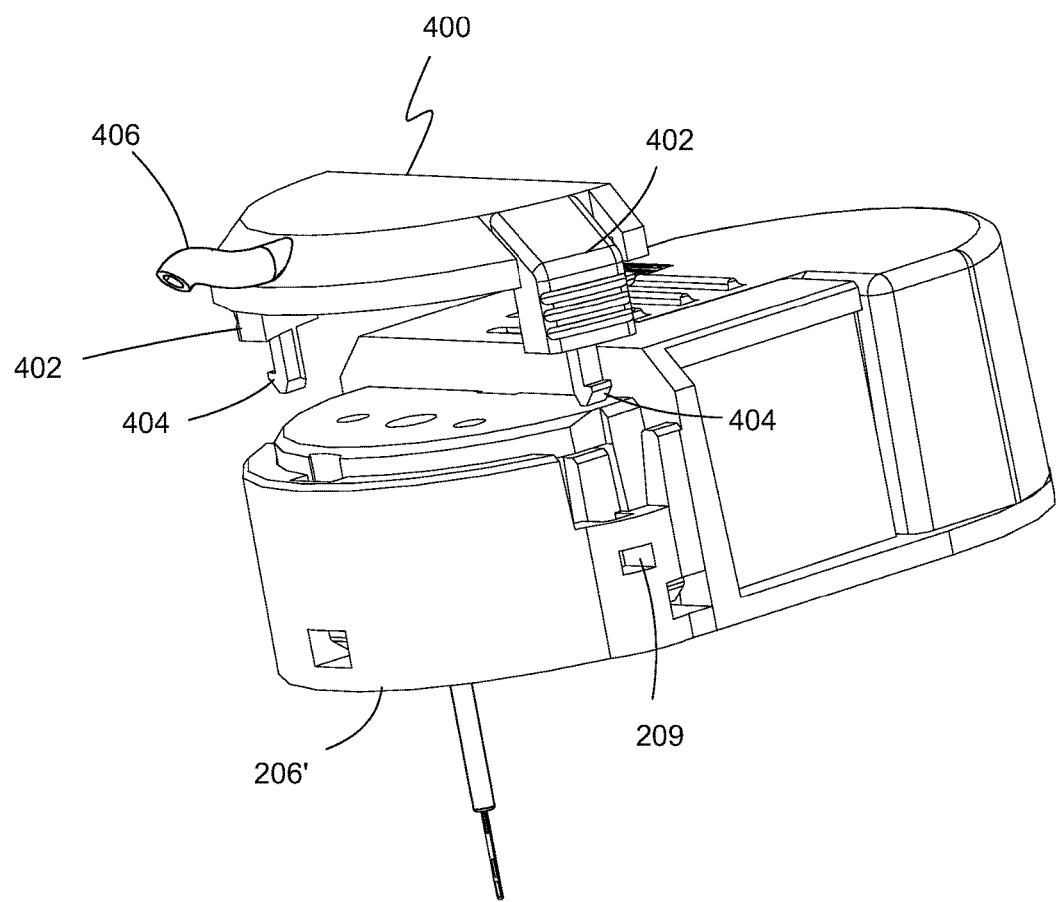
FIG. 29 is a partially exploded, perspective view of the sensor housing assembly with the single lumen and showing the medication delivery assembly decoupled from the sensor housing.

FIG. 29 illustrates medication delivery assembly 400 decoupled from sensor housing 206'. Medication delivery assembly 400 has a pair of resilient sensor housing engagement tabs 402, each with an engagement tab catch structure 404 extending from a respective engagement tab 402. Engagement tab catch structure 404 is received within an engagement tab receiver 209 in sensor housing 206'. A flexible medication delivery tube 406 is connected to medication delivery assembly 400.

Figure 30:
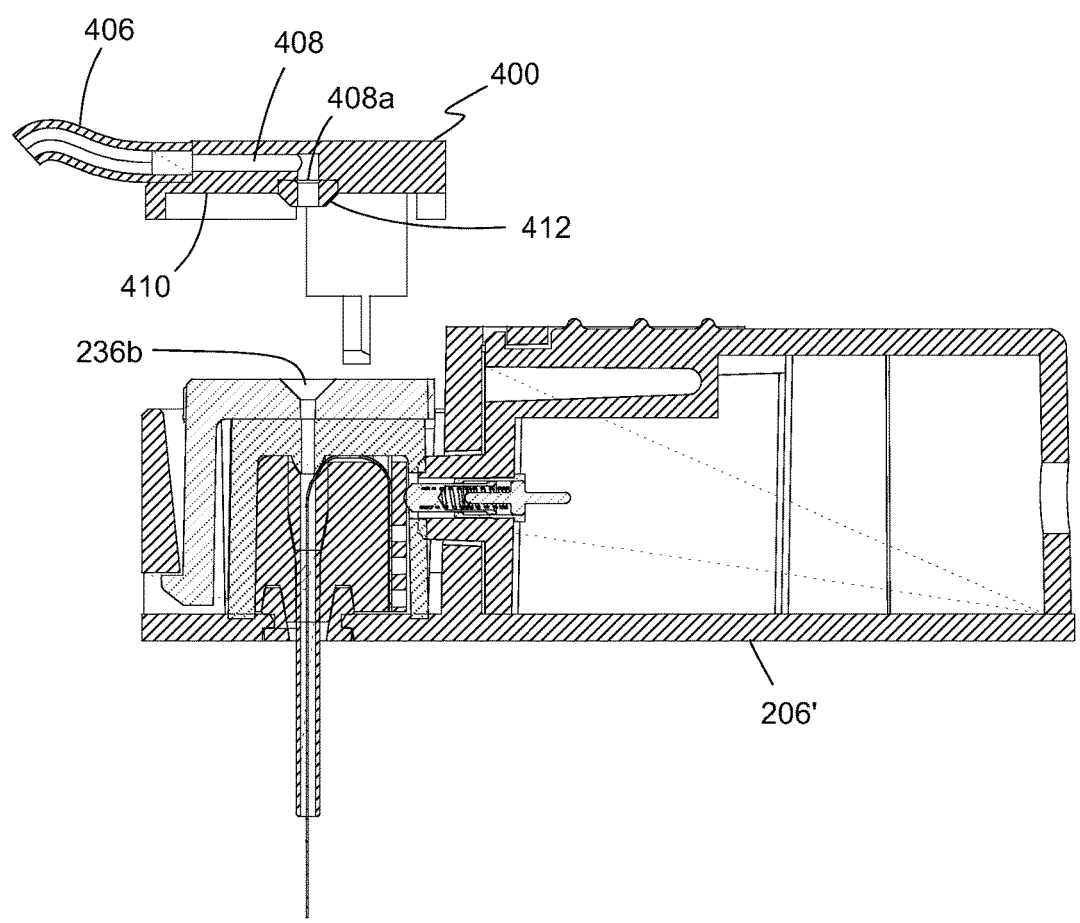
FIG. 30 is a sectional, side view of the sensor housing assembly and medication delivery assembly of FIG. 29.

Turning now to FIG. 30, there is illustrated a side, sectional, elevation view of the medication delivery assembly 400 shown in FIG. 29. Medication delivery assembly 400 has a delivery bore 408 that communicates on one end with delivery tube 406 and ends at delivery bore opening 408a in a bottom surface 410 of assembly 400. Delivery bore opening 408a has a sealing member 412 that aligns with and seals into needle bore opening 236b in a top surface 236c of deployment body 236a. It is contemplated that a sealing cover 450 (not shown) may be used to plug needle bore opening 236b when medication delivery assembly 400 is not used or temporarily removed from sensor housing 206'. Sealing cover 450 would have all of the structural features of delivery assembly 400 except that there would be no delivery bore 408, delivery tube 408 or delivery bore opening 408a.

Figure 31:
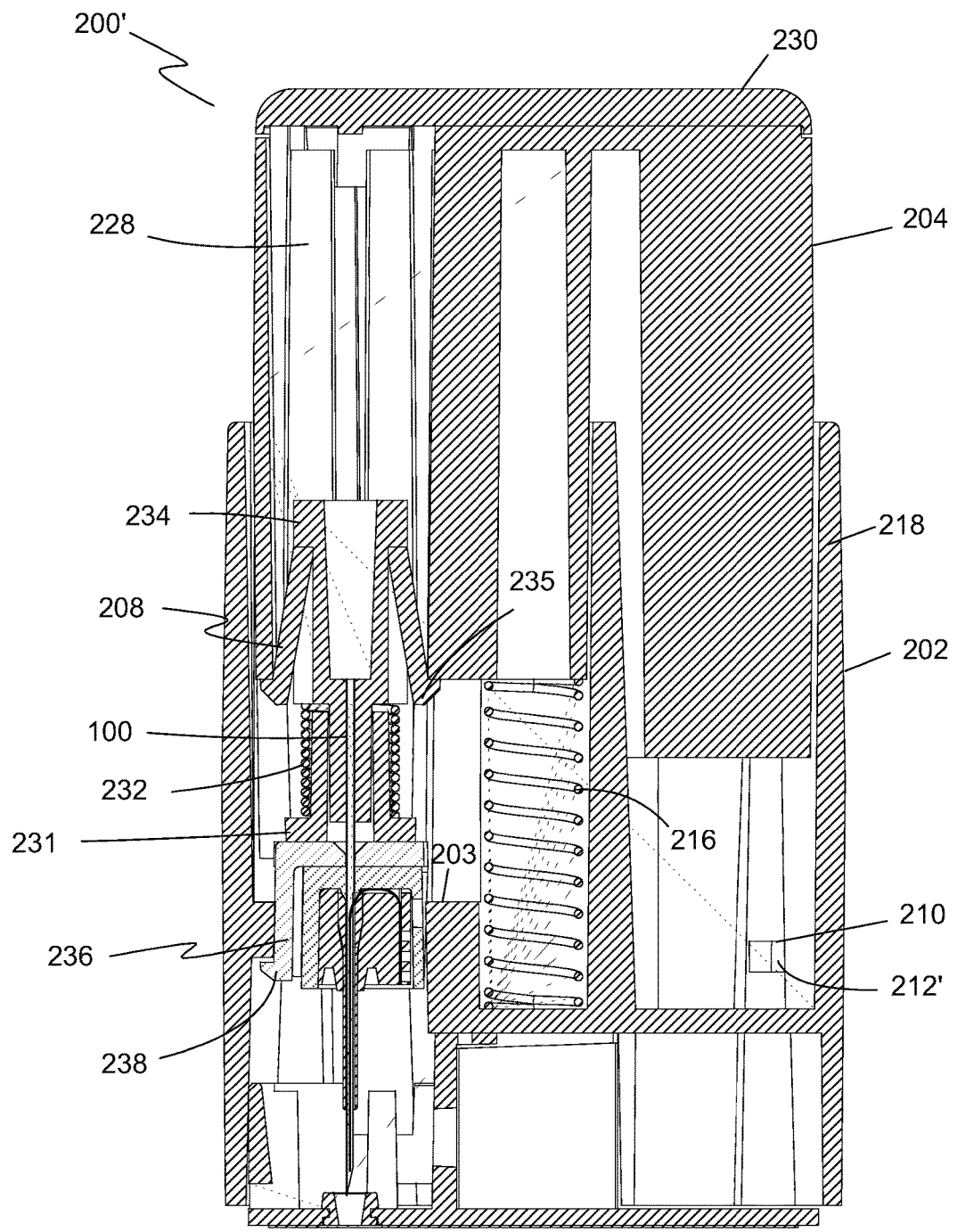
FIG. 31 is a sectional, side view of the inserter assembly of FIG. 23 shown in a pre-insertion position.

FIG. 31 shows a side, cross-sectional, elevation view of inserter assembly 200'. Housing body 202 includes at least one first catch surface 210 defined by a recess 212', opening, ledge, protrusion, or other structure. First catch surface 210 is constructed and sized to engage a corresponding resilient locking catch 214 (hidden from view) on deployment button 204 when a user presses deployment button 204 into housing body 202 from a first or ready position (shown in FIG. 31) to a second or inserted position (shown in FIG. 32). One or more springs 216 (e.g., coil spring) disposed between deployment button 204 and housing body 202 bias deployment button 204 towards the first or ready position as shown in FIG. 31. When deployment button 204 is in the first (ready position), locking catch 214 (hidden from view) is held inward in tension by abutment with housing wall 218 (more clearly shown in the first embodiment in FIG. 10). When the user presses deployment button 204 down, the tension on locking catch 214 causes locking catch 214 to move outward towards its resting, non-tensioned position to engage first catch surface 210 when locking catch aligns with recess 212'. Of course as previously disclosed, housing body 202 and deployment button 204 can be configured so that first catch surface 210 is on deployment button 204 and locking catch 214 is on housing body 202. Other releasable locking mechanisms known in the art are also acceptable. In one embodiment, inserter assembly 200' includes at least two first catch surfaces 210 and corresponding locking catches 214.

Deployment mechanism 208 is slidably received in a deployment mechanism cavity 228 in deployment button 204. A deployment cap 230 closes mechanism cavity 228 and can be removed for access to deployment mechanism 208. Deployment mechanism 208 includes a deployment spring 232, a needle/sharp carrier 234 with a needle carrier catch 235 and a sharp/needle 100, and a sensor deployment assembly 236 with a resilient deployment catch 238. Deployment spring 232 (e.g., a coil spring) is disposed and supported by a spring support component 231 on one end and connected to needle carrier 234 on an opposite end. Spring support component 231 is integrally formed with deployment button 204 or fixedly attached to deployment button 204 within deployment mechanism cavity 228. Spring support component 231 retains deployment spring 232 within deployment button 204. Deployment spring 232 is disposed between spring support component 231 and needle carrier 234 in a tensioned/compressive orientation. Needle carrier catch 235 prevents needle carrier 234 from being moved within deployment mechanism cavity 228 towards a deployment cap 230 by deployment spring 232. When the user presses deployment button 204, needle carrier catch 235 is released by carrier release surface 203 of housing body 202 and deployment spring 232 then biases needle carrier 234 towards deployment cap 230 thereby moving needle/sharp 100 out of the way after having inserted lumen 973, 974 and sensor 120 subcutaneously in the patient.

Figure 32:
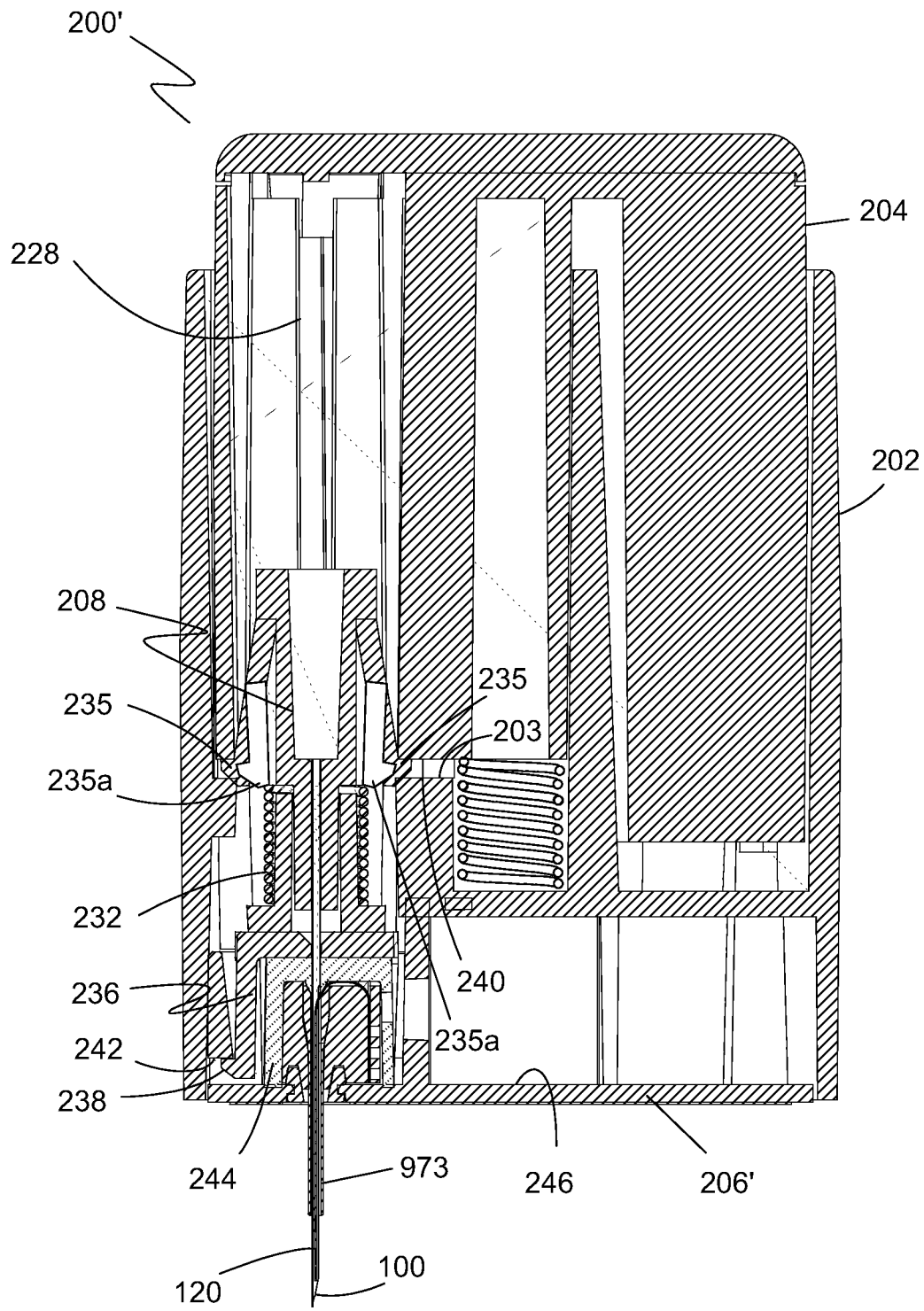
FIG. 32 is a sectional, side view of the inserter assembly of FIG. 23 shown in an intermediate, sensor inserting position.

Referring now to FIG. 32, a side, cross-sectional view of inserter assembly 200' is shown with deployment button 204 and deployment mechanism 208 in their respective second positions (needle inserted positions). When the user presses button 204, deployment mechanism 208 moves downward towards sensor housing 206' due to engagement between a button catch surface 240 and carrier catch 235. At the end of travel for deployment button 204, a deployment guide 244 abuts a floor 246 or other structure of sensor housing 206' to stop the travel of deployment button 204 and of deployment mechanism 208. In its second carrier position (inserted position), sensor deployment assembly 236 is positioned and retained within sensor housing 206' because deployment body catch 238 engages base catch surface 242. In the second carrier position, the deployed continuous monitoring sensor 120 and lumen 973 of sensor deployment assembly 236 are retained by sensor housing 206' and sensor 120 is positioned for electrical communication with electronic module 300' (internal electrical/electronic components not shown for clarity) attached to sensor housing 206'. Simultaneously with retention of continuous monitoring sensor 120 in sensor housing 206', carrier catch 235 contacts carrier release surface 203. This causes carrier catch 235 to move to a second carrier catch orientation as shown by the dashed outline of carrier catch 235a and to disengage from button catch surface 240 with an audible "click" thereby allowing deployment spring 232 to automatically return carrier assembly 208 to a third carrier position (up position) with sharp 100.

Figure 33:
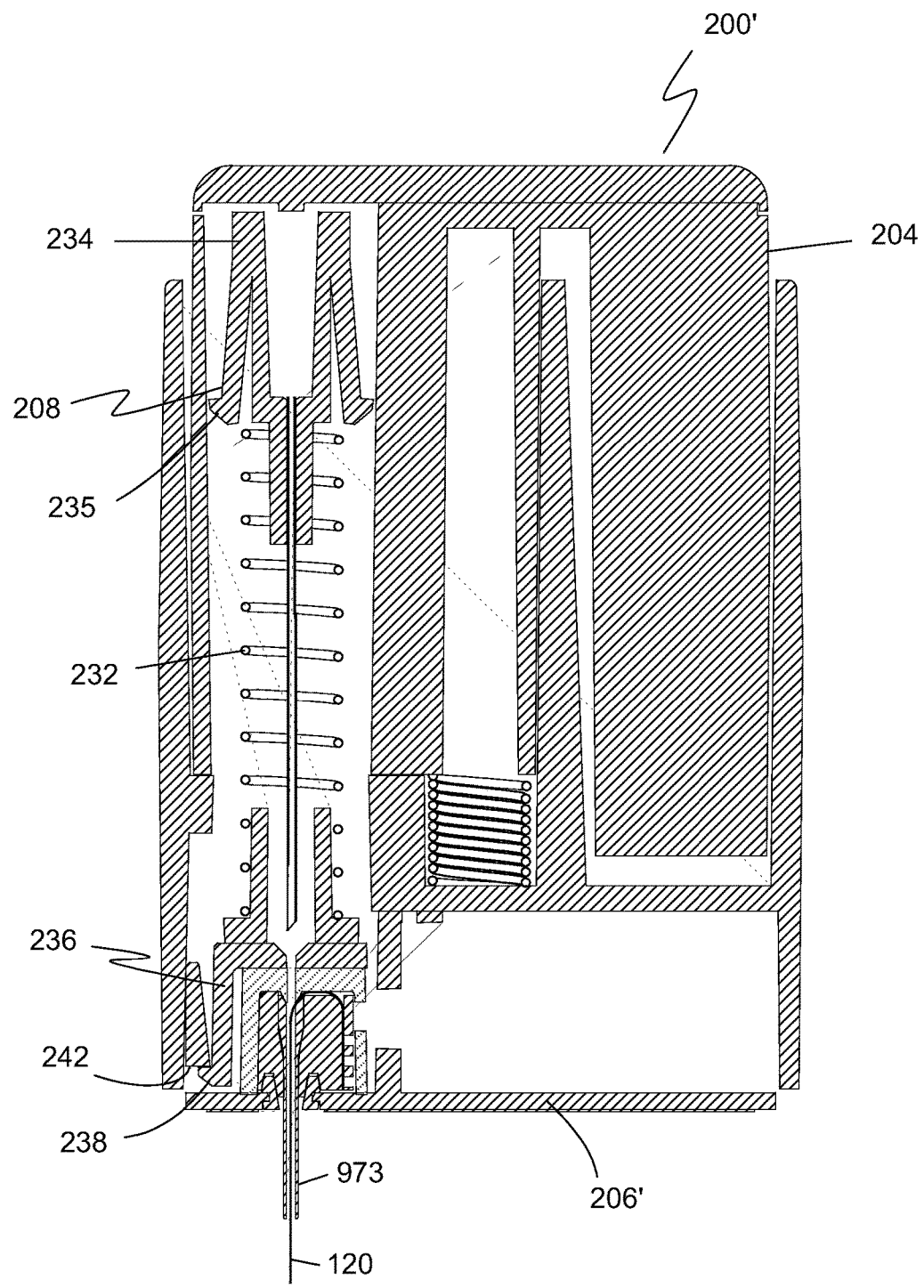
FIG. 33 is a sectional, side view of the inserter assembly of FIG. 23 shown in a post-insertion position with the needle carrier in a retracted position and immediately prior to separation of the introducer housing and deployment button from the sensor housing.

FIG. 33 shows a side, cross-sectional view of inserter assembly 200' in a post sensor deployment position with deployment button 204 in its second position (down position), sensor 120 and lumen 973 deployed, and deployment mechanism 208 having returned to its third carrier position (up position). Deployment body catch 238 remains engaged with base catch surface 242 to maintain sensor deployment assembly 236 engaged with sensor housing 206'. Locking catch(es) 214 also remain engaged with first catch surface(s) 210 to maintain button 204 in its second position. With continuous monitoring sensor 120 now deployed, housing body 202 with deployment button 204 and deployment mechanism 208 (aka the deployment assembly) may be disengaged from sensor housing 206' and removed, leaving sensor housing 206' in place on the patient for continuous glucose monitoring and automatic insulin delivery.

In one embodiment, sensor housing 206' has a very compact form factor measuring 1.5 inches (7.1 mm) long by 1.0 (25.4 mm) wide by 0.3 (7.6 mm) high that is very small and convenient to the patient.

Continuous Monitoring System with Top-Mounted Electronics Module

FIG. 34 illustrates another embodiment of an inserter assembly 200" for a continuous monitoring system. Like the embodiments shown in FIG. 9 and FIG. 23, an inserter assembly 200" includes a housing body 202, a deployment button 204 slidably received in housing body 202, and a sensor housing 206" that is removably attachable to housing body 202. As previously disclosed, housing body 202, sensor housing 206", and deployment button 204 are collectively referred to herein as a deployment assembly 1000. Housing body 202 includes one or more recesses 212' for engagement with deployment button 204 and also includes a locking mechanism 205' (e.g., resilient tab, clip, protrusion, etc.) that engages housing outside catch surface 206b on sensor housing 206' and retains it together with the deployment assembly. Locking mechanism 205' functions in the same way as previously discussed with respect to inserter assembly 200' and disengages from sensor housing 206" when the sensor 120 is deployed. Optionally, sensor housing 206" includes an attachment pad 600 disposed on a bottom surface 252. The sensor housing 206" has a lower profile than previously disclosed embodiments.

FIG. 35 is a rear view of inserter assembly 200" with attachment pad 600 disposed on a bottom surface 252 of sensor housing 206". It is understood that attachment pad 600 may be pre-installed on bottom surface 252 of sensor housing 206" or may be applied by the user prior to use of inserter deployment assembly 1000. Attachment pad 600 secures sensor housing 206" to the patient upon deployment of the continuous monitoring system.

FIG. 36 shows a side, cross-sectional view of inserter assembly 200 taken along line E-E of FIG. 34. Housing body 202 includes at least one first catch surface 210 defined by a recess 212', opening, ledge, protrusion, or other structure. First catch surface 210 is constructed and sized to engage a corresponding resilient locking catch 214 (not shown) on deployment button 204 when a user presses deployment button 204 into housing body 202 from a first or ready position (shown in FIG. 10) to a second or insertion position (shown in FIG. 11). One or more springs 216 (e.g., coil spring) disposed between deployment button 204 and housing body 202 bias deployment button 204 towards the first or ready position as shown in FIG. 36. Similarly as discussed above with reference to FIG. 10, when deployment button 204 is in the first (ready position), locking catch 214 (shown in FIG. 10) is held inward in tension by abutment with housing wall 218. When the user presses deployment button 204 down, the tension on locking catch 214 causes locking catch 214 to move outward towards its resting, non-tensioned/non-compressed position to engage first catch surface 210. Of course, housing body 202 and deployment button 204 can be configured so that first catch surface 210 is on deployment button 204 and locking catch 214 is on housing body 202. Other releasable locking mechanisms known in the art are also acceptable. In one embodiment, inserter assembly 200 includes at least two first catch surfaces 210 and corresponding locking catches 214 as shown in FIG. 10.

Deployment mechanism 208 is slidably received in a deployment mechanism cavity 228 in deployment button 204. A deployment cap 230 closes mechanism cavity 228 and can be removed for access to deployment mechanism 208. Deployment mechanism 208 includes a deployment spring 232, a needle/sharp carrier 234 with a needle carrier catch 235, and a sensor deployment assembly 236' with a resilient deployment catch 238. Deployment spring 232 (e.g., a coil spring) is disposed to engage between spring support component 231 and needle carrier 234 in a tensioned orientation. Needle carrier catch 235 prevents needle carrier 234 from being moved towards deployment cap 230 by deployment spring 232. When the user presses deployment button 204 into housing body 202, needle carrier catch 235 is released by carrier release surface 203 of housing body 202 and deployment spring 232 then biases needle carrier 234 towards a deployment cap 230.

FIG. 37 is an enlarged view of sensor deployment assembly 236'. Sensor deployment assembly 236' includes a deployment body 236a, a sensor carrier 270, a sensor board 280', and a needle bore 236b that extends completely through sensor deployment assembly 236'. In this embodiment, the deployment guide 244 has been eliminated and a modified grommet 251' (shown in FIG. 36) has been incorporated to provide enhanced sealing between sensor carrier 270 and sensor housing 206". As illustrated in FIG. 37, sensor 120 is bent so that the electrical contact portion having the plurality of contact pads is perpendicular to the electrodes and the deployment axis.

FIG. 38 is a rear, cross-sectional view of inserter assembly 200". As illustrated, locking mechanism 205' is in its natural state of being inwardly oriented and protrusion 205a engaging a catch surface 206a of the sensor housing 206" to retain sensor housing 206" to housing body 202. As the deployment button is pushed down, a release surface 204a of side walls of the deployment button 204 engage the locking mechanism 205', 205 of the housing body 202 (see also FIG. 53D).

Figure 39:
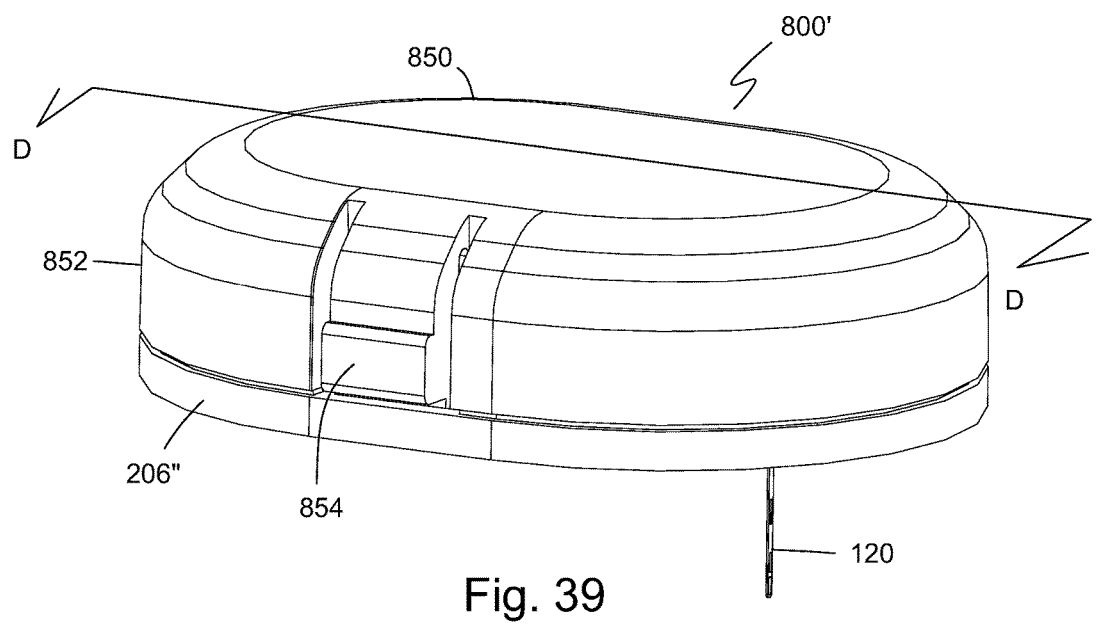
FIG. 39 is a side and top perspective view of another embodiment of a sensor housing assembly of the present invention.

Turning now to FIG. 39, there is illustrated a sensor housing assembly 800'. Sensor housing assembly 800' is fully assembled after the subcutaneous sensor 120 is implanted into a patient's skin and the electronic cover assembly 850 is connected to the sensor housing 206". Electronic cover assembly 850 includes a cover 852 with at least one resilient cover locking tab 854 that secures cover 852 to sensor housing 206".

Figure 40:
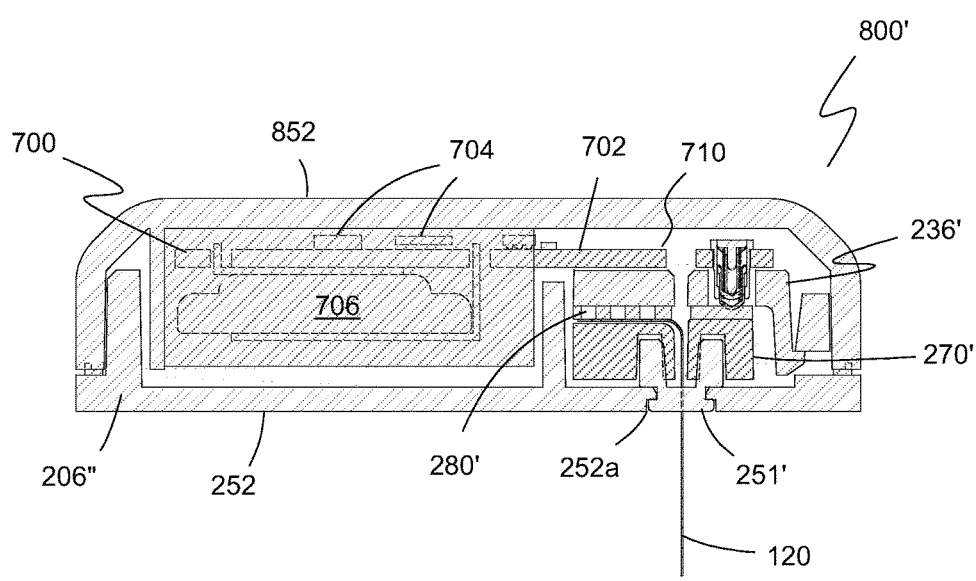
FIG. 40 is a side, cross-sectional view of the sensor housing assembly of FIG. 39 as taken along line D-D of FIG. 39.

FIG. 40 illustrates a cross-section view of the sensor housing assembly 800' taken along line D-D of FIG. 39. As with the previous embodiment shown in FIG. 14, the sensor deployment assembly 236' is retained within sensor housing 206". Sensor 120 extends through a grommet 251' that is secured within a sensor opening 252a in bottom surface 252 of sensor housing 206". The improvement in the structural configuration of grommet 251' along with a modification to the sensor carrier 270' that provides better sealing between grommet 251' and sensor carrier 270', which allows for the elimination of the deployment guide 244 illustrated in FIG. 14.

Cover 852 contains electronic module 700, which has a module circuit board 702, a plurality of electronic components 704 that form the electrical measurement circuit, and a battery 706 to power the circuit. The module circuit board 702 has a sensor deployment assembly portion 710 that is oriented within cover 852 to extend over sensor deployment assembly 236' where sensor deployment assembly portion 710 has a plurality of electrical contacts/connectors that electrically couple the measurement circuit to the respective electrical coupling pads 282' (shown in FIG. 41) of sensor circuit board 280'. When the electronic cover assembly 850 is assembled to sensor housing 206", all of the sensor electrical connections are made between the electronic circuit board 702 and the sensor circuit board 280', including turning on the power from battery 706 to the measurement circuit.

Figure 41:
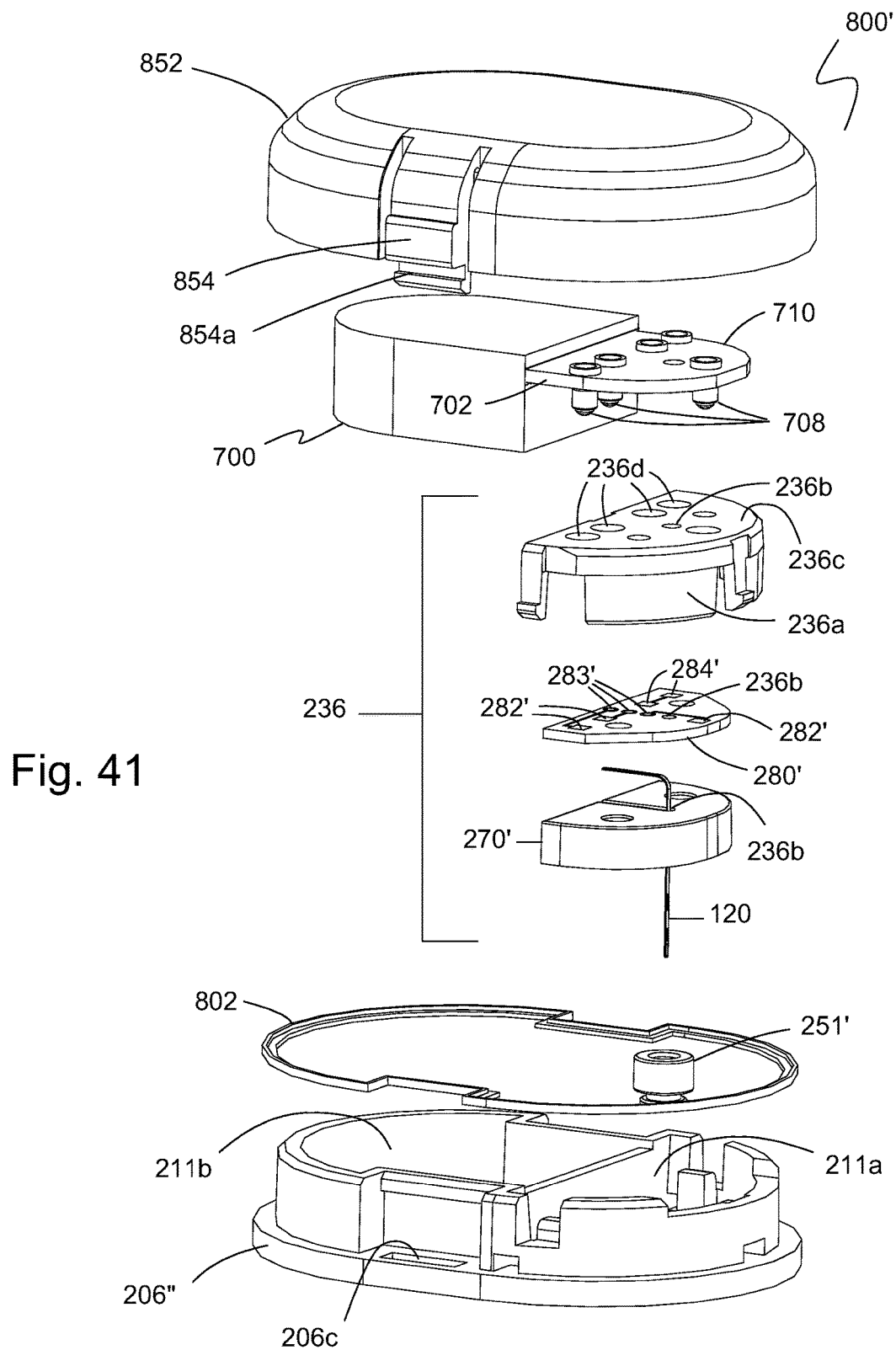
FIG. 41 is an exploded, perspective view of the sensor housing assembly of FIG. 39 showing various components.

Turning now to FIG. 41, there is illustrated an exploded view of the components of the sensor housing assembly 800'. In this embodiment, sensor housing assembly 800' includes sensor housing 206", a housing assembly gasket 802, sensor deployment assembly 236, electronic module 700, and cover 852. Sensor housing 206" includes a sensor deployment assembly recess 211a and an electronic module receiving recess 211b. An assembly gasket 802 is positioned between a perimeter of sensor housing 206" and a perimeter of cover 852 to provide a seal against dust and moisture from entering into sensor housing assembly 800'. A grommet 251' is disposed at a bottom opening 252a in bottom surface 252 of sensor housing 206" to provide a seal between sensor housing 206" and sensor deployment assembly 236.

Sensor deployment assembly 236 includes deployment body 236a, sensor carrier 270', sensor circuit board 280', and sensor 120 coupled to sensor deployment body 236a. Sensor deployment assembly 236 also includes a needle bore 236b through the entire assembly 236 into which sensor 120 is disposed and from which sensor 120 extends. Sensor circuit board 280' has a plurality of electrically conductive electronic coupling pads 282', a plurality of electrically conductive sensor coupling contacts 283' and a plurality of electrically conductive power coupling pads 284'. Power coupling pads 284' close the measurement circuit allowing electrical power from battery 706 to operate the measurement circuit. Deployment body 236a has a plurality of through openings 236d in top surface 236c to accommodate a plurality of electrical connectors 708 allowing the electrical connectors 708 to electrically couple with the sensor circuit board 280'.

Electronic module 700 includes module circuit board 702 with sensor deployment assembly portion 710 that is oriented to extend over sensor deployment assembly 236' where sensor deployment assembly portion 710 has the plurality of electrical connectors 708 that electrically couple the measurement circuit to the respective electrical coupling pads 282', 284' of sensor circuit board 280'. Cover 852 captures assembly gasket 802 between the perimeter of cover 852 and the perimeter of sensor housing 206" by the interlocking of resilient cover locking tab 854 with a mating sensor housing opening 206c where a tab catch surface 854a is matingly captured by a corresponding retaining surface (not shown) in sensor housing opening 206c.

Figure 42:
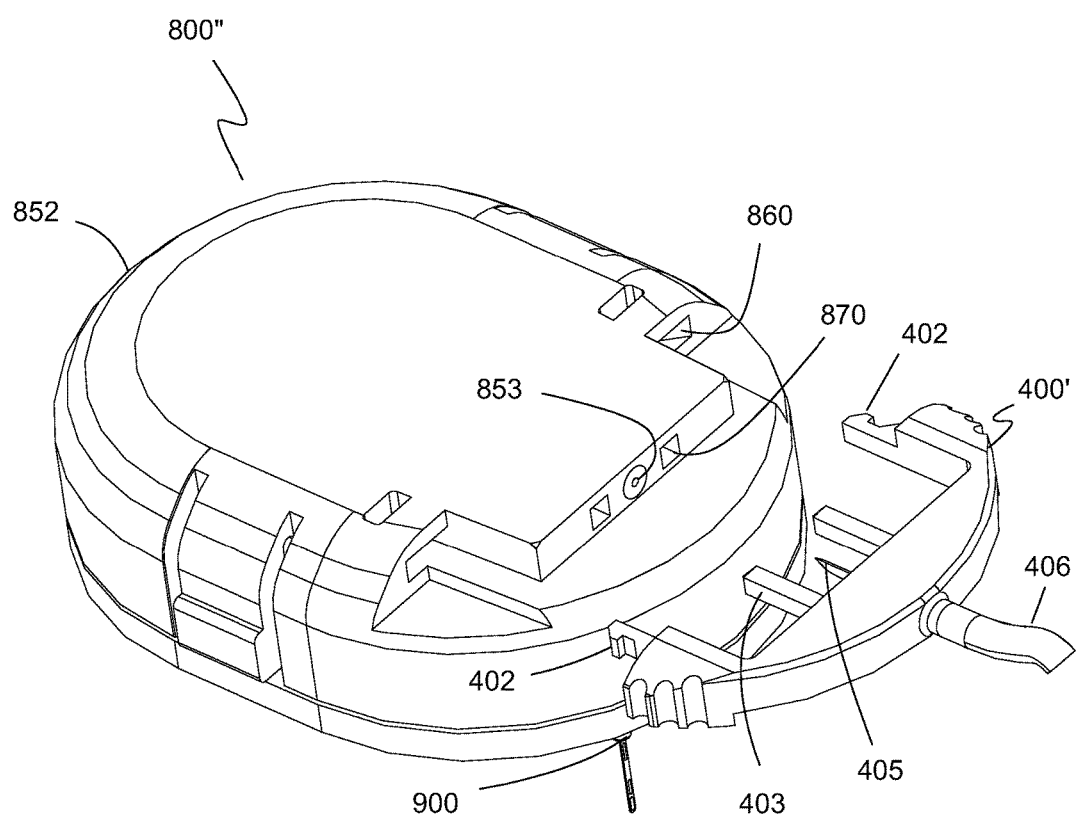
FIG. 42 is side and top perspective view of another embodiment of a sensor housing assembly of the present invention with a single lumen and showing a medication delivery assembly separated from the sensor housing assembly.

Turning now to FIG. 42, there is illustrated another embodiment of a sensor housing assembly 800". In this embodiment, a lumen 900 for medication delivery is incorporated within sensor deployment assembly 236 (shown in FIG. 45). Cover 852 is modified to accept attachment of a medication delivery assembly 400' or a cover plug (not shown). Cover 852 includes a fluid receiving port 853 and at least one delivery assembly retaining slot 860. Medication delivery assembly 400' has a fluid coupling stem 405 that is received into fluid receiving port 853 on one end and to a flexible medication delivery tube 406 on an opposite end. Medication delivery assembly 400' also has at least one resilient cover engagement tab 402 that matingly engages with the at least one delivery assembly retaining slot 860 to capture and retain medication delivery assembly 400' onto cover 852. Medication delivery assembly 400' may optionally include one or more alignment fingers 403 that slide into corresponding finger receiver slots 870 on cover 852 to facilitate alignment and connection of fluid coupling stem 405 to fluid receiving port 853.

Figure 43:
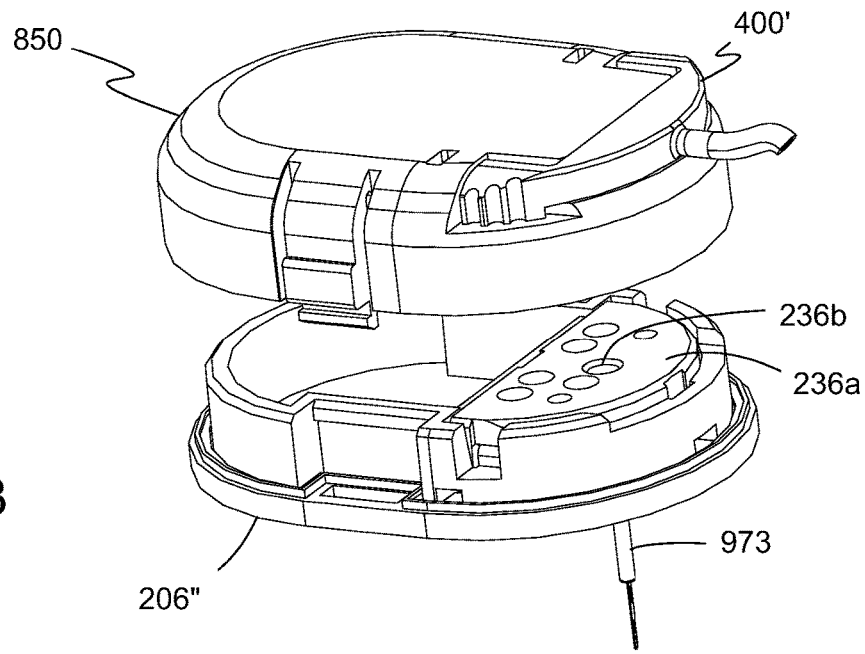
FIG. 43 is a side and top perspective view of the sensor housing assembly of FIG. 42 showing the electronic cover assembly separated from the sensor housing.
Figure 44:
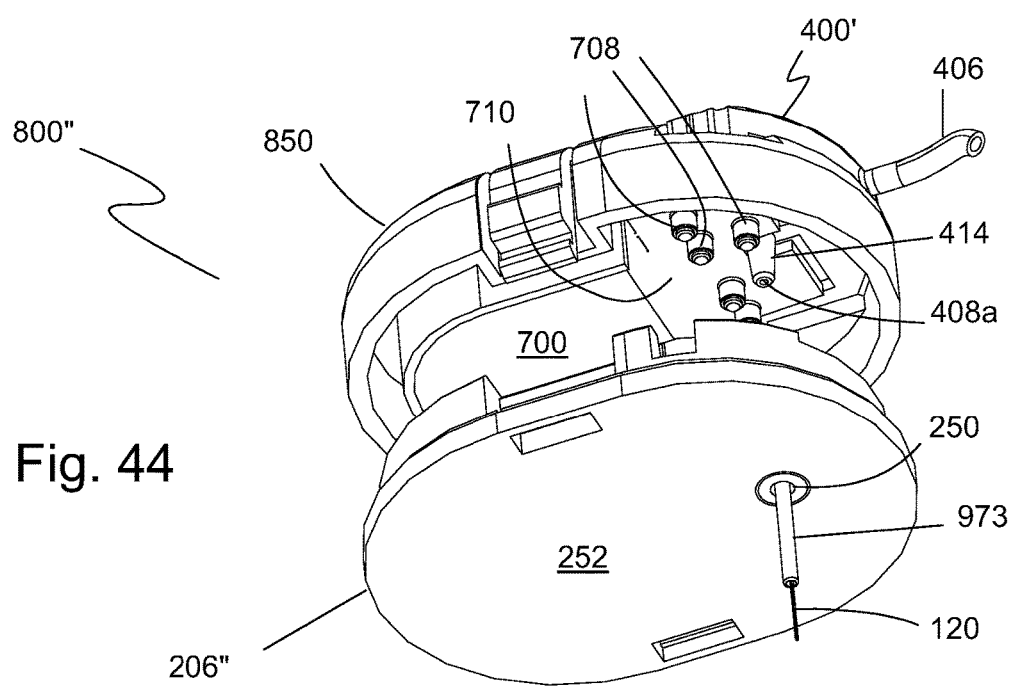
FIG. 44 is a side and bottom perspective view of the sensor housing assembly of FIG. 43.

FIGS. 43 and 44 are views of sensor housing assembly 800" showing sensor housing 206" with sensor deployment assembly 236 deployed within sensor housing 206" and electronic cover assembly 850 separated from sensor housing 206". FIG. 43 illustrates a top perspective view of the sensor deployment assembly 236 inside of sensor housing 206" showing a larger needle bore 236b to accommodate a delivery bore stem 414 shown in FIG. 44. Further and due to the inclusion of lumen 900 and medication delivery assembly 400', the arrangement of one of the plurality of through openings 236 in top surface 236c of deployment body 236a is modified to accommodate insertion of delivery bore stem 414 into needle bore 236b. The bottom perspective view of FIG. 44 shows the underside of electronic cover assembly 850 and the location of electronic module 700 and sensor deployment assembly portion 710 of module circuit board 702. In this embodiment, a single lumen 973 is illustrated and recognizable due to the sensor 120 extending from lumen 973. Lumen 973 extends through sensor opening 250 in bottom surface 252 of sensor housing 206".

Figure 45:
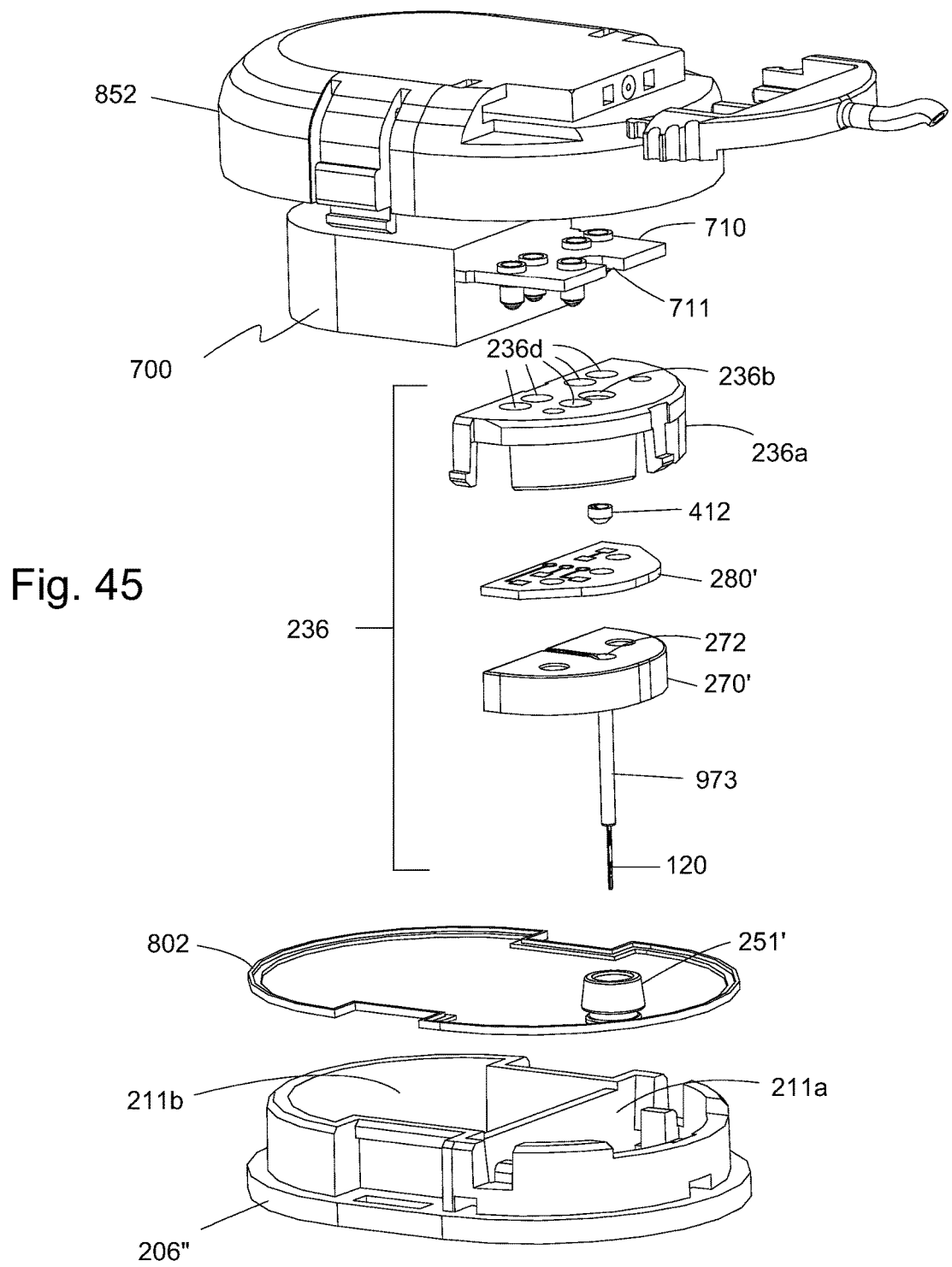
FIG. 45 is an exploded, perspective view of the sensor housing assembly of FIG. 42 showing various components.

Turning now to FIG. 45, there is illustrated an exploded view of sensor housing assembly 800". Like FIG. 41, FIG. 45 shows the various components with the addition of lumen 972 and sealing member 412 within needle bore 236b for sealing delivery bore stem within sensor deployment assembly 236. In addition, sensor deployment assembly portion 710 has an electronic circuit board slot 711 to accommodate delivery bore stem 414 (shown in FIG. 44) therethrough.

FIG. 46 is an enlarged view of the electronic circuit board assembly 701 of the electronic module 700. As can be seen, electronic circuit board 702 has a plurality of electronic components 704 that form the electrical measurement circuit for sensor 120. Also shown electrically coupled on electronic circuit board 702 to the plurality of electronic components 704 is radio antenna 724, which is used for transmitting data to a data receiver and display (not shown). Battery 706 provides electrical power to the plurality of electronic components 704 and radio antenna 724. A sensor deployment assembly portion 710 of circuit board 702 has a plurality of electrical connectors 708 and a circuit board slot 711.

FIG. 47 illustrates an electronic module potted housing 720 from which sensor deployment assembly portion 710 extends. Potted housing 720 is a potting material that encapsulates electronic circuit board assembly 701 and battery 706 shown in FIG. 46. Potted housing 720 prevents a user from viewing and touching the plurality of electronic components 704 and radio antenna 724. Although reference number 722 appears to indicate a slot of sorts from which sensor deployment assembly portion 710 extends, it merely indicates the location in the potting material where the encapsulating material ends and the electronic circuit board continues that is not encapsulated. Electronic circuit board assembly 701, battery 706 and potted housing 720 form electronic module 700.

FIGS. 48 and 49 illustrate a sensor housing assembly 800" with a dual lumen configuration. The notable difference between the structural arrangement of the components in this embodiment compared to the embodiment for a single lumen shown in FIGS. 43-45 is the position of the electrical contact portion 124. Electrical contact portion 124 is situated between sensor circuit board 280' and deployment body 236a whereas in the single lumen embodiment of FIGS. 43-45, electrical contact portion 124 is situated between sensor circuit board 280' and sensor carrier 270'.

Figure 50:
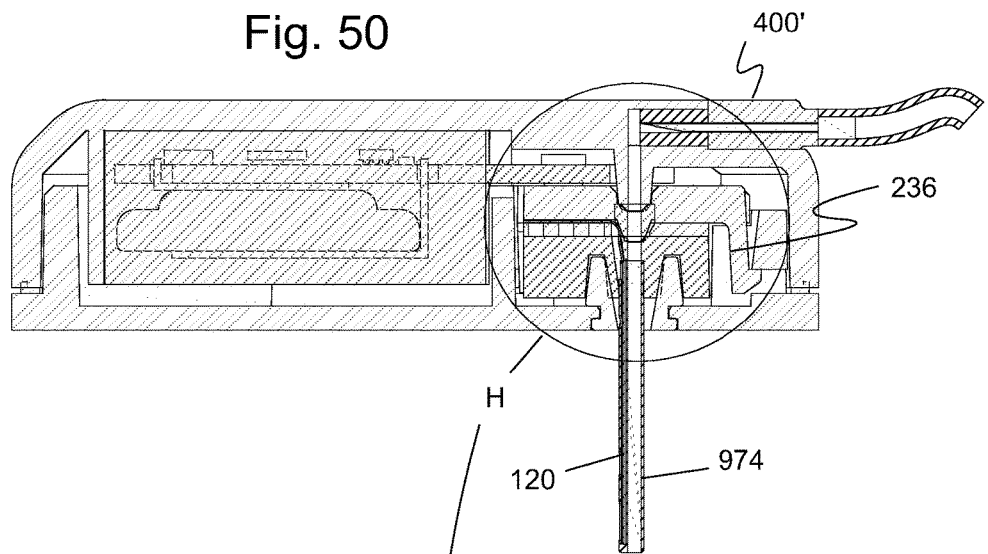
FIG. 50 is a side, cross-sectional view of the sensor housing assembly of FIG. 48 as taken along line G-G of FIG. 48.
Figure 51:
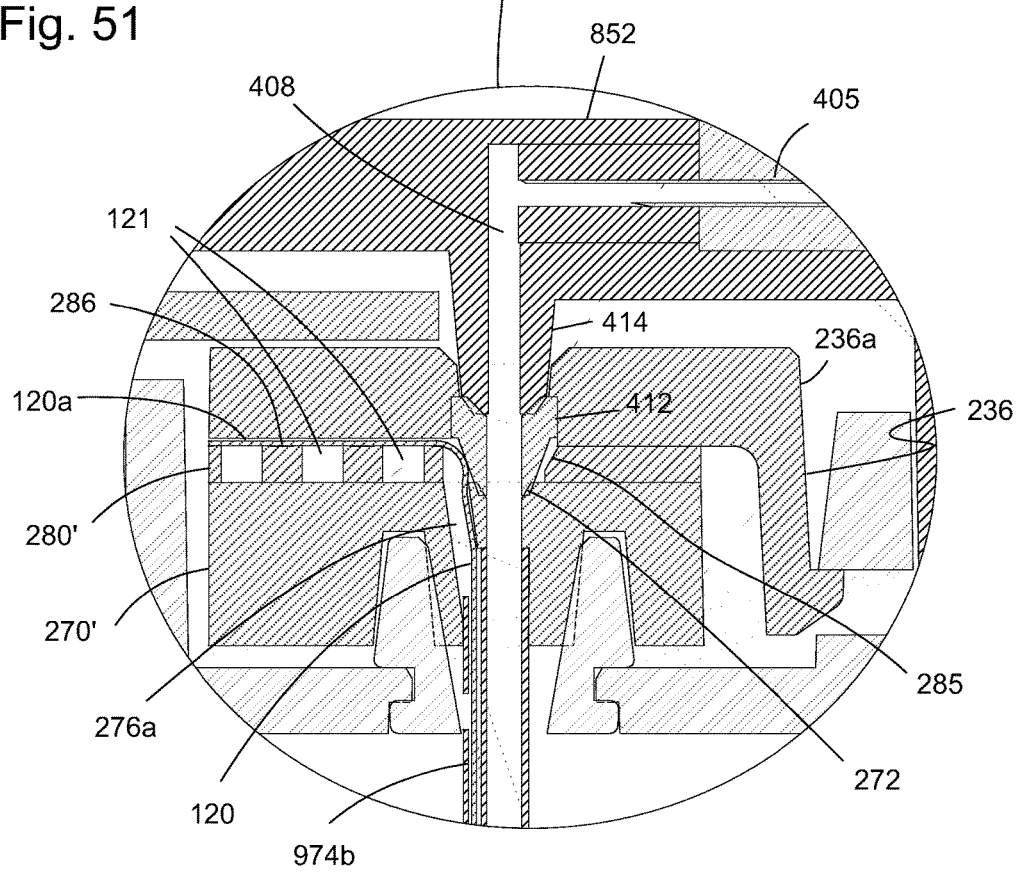
FIG. 51 is an enlarged view of the circled area H of FIG. 50.

FIGS. 50 and 51 illustrate a cross-sectional view showing the relative position of the delivery bore 408 of the medication delivery assembly 400' to the components that form sensor deployment assembly 236 in the dual lumen embodiment. FIG. 51 is an enlarged view of the area delineated by circular indicator H. Delivery bore 408 extends from fluid receiving port 853 to delivery bore opening 408a in delivery bore stem 414. Delivery bore stem 414 fits into needle bore 236b and against sealing member 412. Sealing member 412 extends from deployment body 236a through sensor circuit board 280' and into sensor/needle bore 272 of sensor carrier 270' providing a water-tight seal. Sensor carrier 270' includes a sensor bore 276a that is transverse to sensor/needle bore 272 and communicates with sensor board opening 285 that forms a portion of needle bore 236b. Dual lumen 974 has first lumen tube 974a aligned with needle bore 236b for sharp/needle 100 and a second lumen tube 974b for sensor 120. Second lumen tube 974b communicates with sensor bore 276a. Sensor proximal portion 120a of sensor 120 extends from second lumen tube 974b through sensor bore 276a and sensor board opening 285, and then across a top sensor board surface 286 where the plurality of contact pads 121 electrically couple sensor coupling contacts 283' of sensor circuit board 280'.

There are several advantages of the various embodiments of the present invention. One aspect of the present invention provides an advantage for a nearly pain-free insertion of the sensor subcutaneously into the skin of a patient. Another aspect of the present invention provides the advantage of a single action that implants the sensor 120, retracts the needle/sharp 100, and releases the inserter assembly 200, 200' leaving the sensor housing 206, 206', 206" with the sensor 120 implanted where the sensor housing is ready for receiving the electronic module 300, 700. In still another aspect of the present invention, it may include a lumen 900 and a medication delivery assembly 400, 400' to facilitate delivery of medication in response to the sensor measurements of sensor 120 in a single sensor housing assembly that is attached to the skin of the patient. In yet another aspect of the present invention, another advantage is the inserter assembly design incorporates a further useful feature, which is the safe retraction of the sharp for safe disposal. A sharp is defined by the FDA (the US Food and Drug Administration) as a device with sharp edges that can puncture or cut skin, and includes devices such as needles, syringes, infusion sets and lancets. Improper disposal or handling of sharps can cause accidental needle stick injuries including transmission of Hepatitis B (HBV), Hepatitis C (HBC) and Human Immunodeficiency Virus (HIV). Used sharps must be placed in a "sharps" container such as the BD™ Home Sharps Container, and fully sealed, before checking with local laws on proper disposal.

The mechanism shown in FIGS. 12 and 33 show the sharp fully retracted into the housing. The sharp is fully covered and is not accessible by finger. By design, the device cannot be made to re-deploy the sharp. No special "sharps" container is required to store and dispose of the housing body after sensor deployment. The entire body can be disposed of according to local laws.

Figures 52A, 52B:
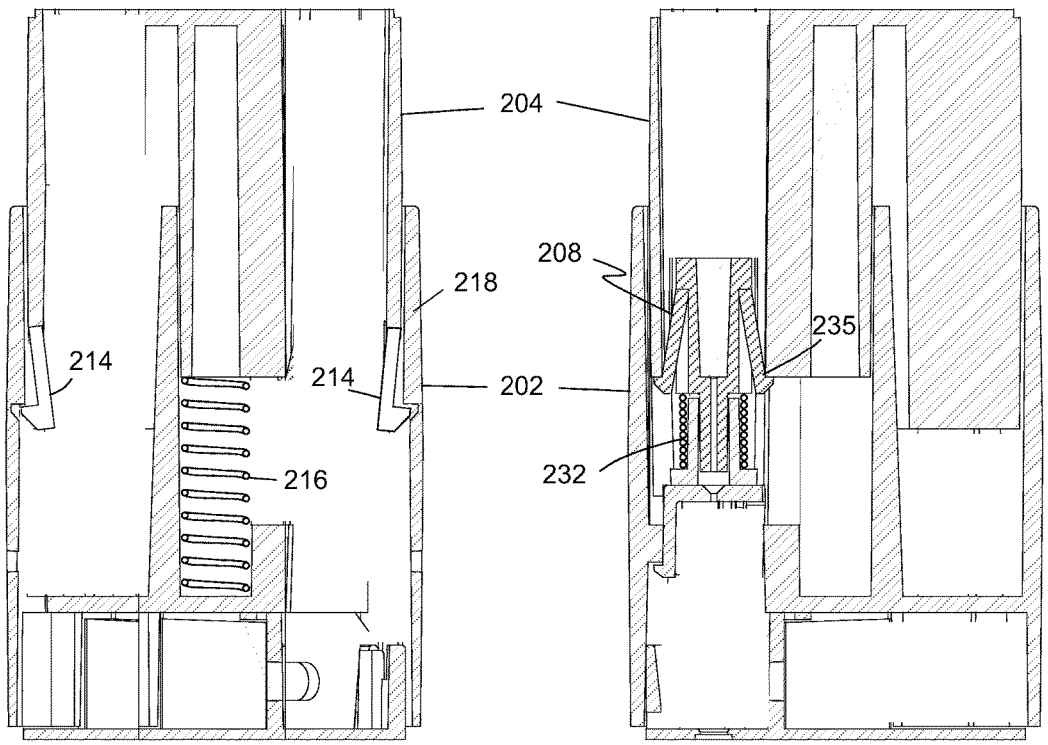
FIGS. 52A, 52B and 52C are simplified cross-sectional views of the inserter assembly showing the position of various inserter catches when the inserter assembly is in the first/ready position.
Figure 52C:
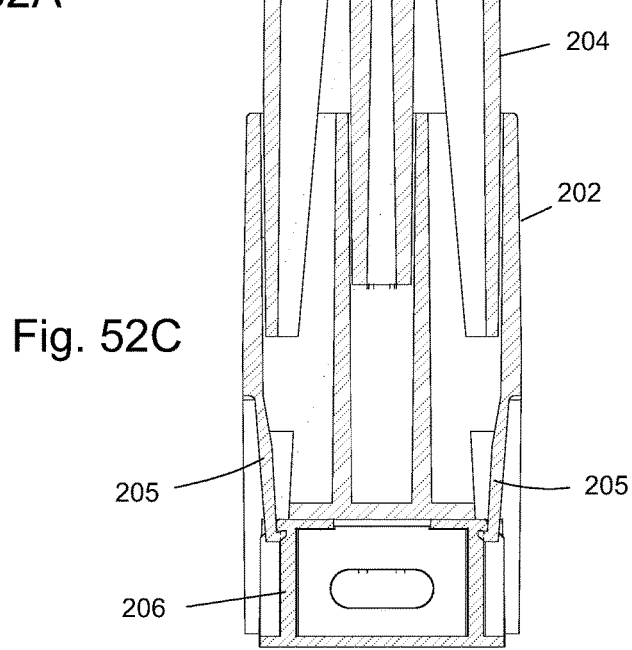

For a better understanding and appreciation of the single action aspect of the present invention, FIGS. 52A-C and 53A-D provide a pictorial cross-sectional illustration in simplified form of this single action aspect. Inserter assembly 200, 200' in FIGS. 52A-C represent the present invention in the ready-to-use position; that is, the assembly is ready for installing a continuous analyte monitoring system on a patient. FIG. 52A shows a cross-sectional view of deployment button 204 in a ready position where the resilient locking catch 214 is tensioned inwardly by the wall 218 of housing body 202. Spring 216 tensions deployment button 204 upwardly while resilient locking catch 214 prevents deployment button 204 from being separated from housing body 202 by spring 216. FIG. 52B shows a different cross-sectional view of deployment mechanism 208 being tensioned by deployment spring 232 where the needle carrier catch 235 prevents any upward movement of deployment mechanism 208 by deployment spring 232. FIG. 52C shows still a different cross-sectional view of housing body 202 where resilient locking mechanism 205 engages sensor housing 206, 206', 206" and retains the sensor housing to the inserter assembly 200, 200'.

Figure 53A:
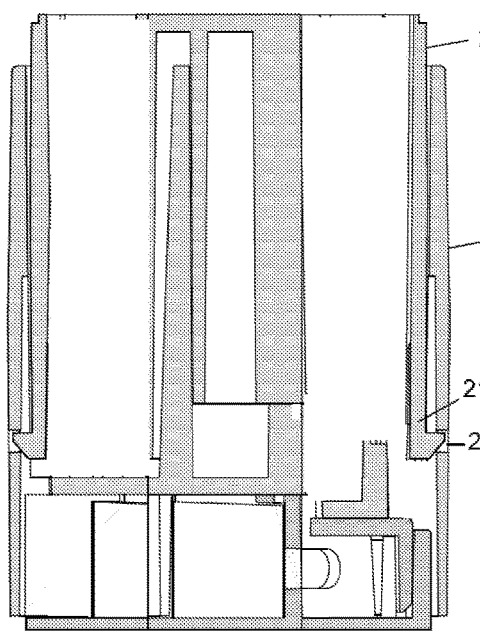
FIGS. 53A, 53B, 53C, and 53D are simplified cross-sectional views of the inserter assembly showing the position of various inserter catches when the inserter assembly has been activated by a single action performed by a user.
Figure 53B:
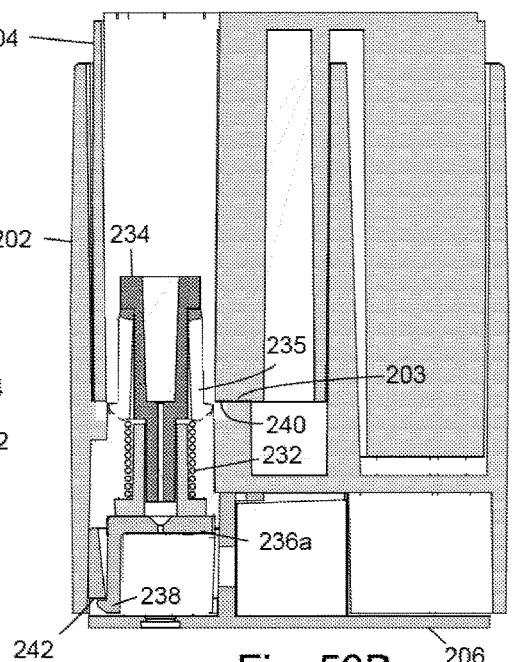
Figure 53C:
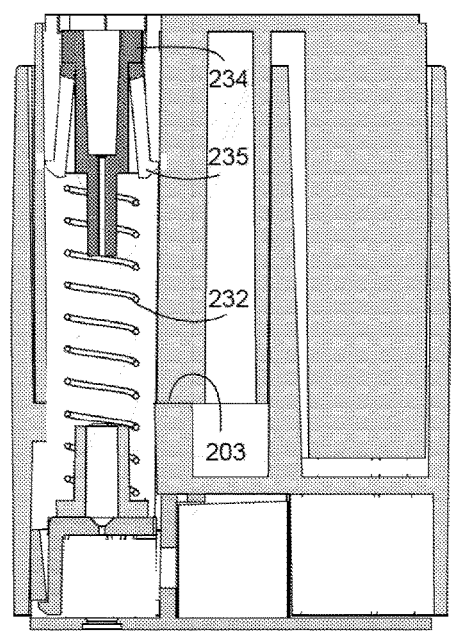
Figure 53D:
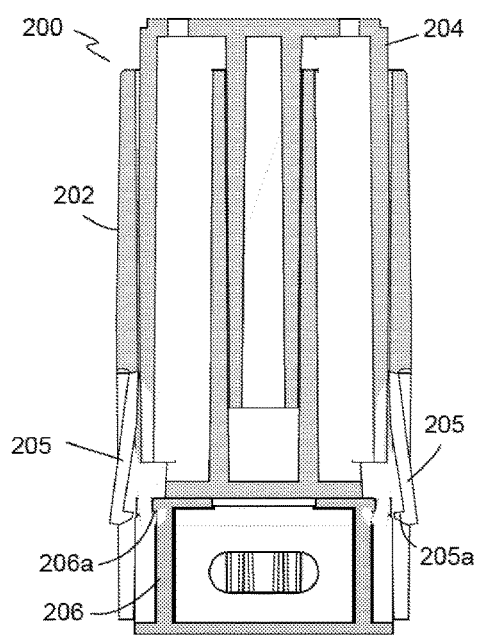

FIGS. 53A-D represent the substantially simultaneous single action of the present invention where the needle 100 implants the sensor 120, the needle 100 retracts, the deployment button 204 gets into a locked position, and the inserter assembly 200, 200' releases from the sensor housing 206, 206', 206". The single action involves simply depressing the deployment button 204. FIG. 53A shows a cross-sectional view of the deployment button 204 in a second, locked position where the resilient locking catch 214 locks into recess 212 of housing 202 when resilient locking catch 214 transforms from the tensioned position to the relaxed position. Substantially simultaneously as the deployment button 204 reaches the second position as FIG. 53B shows in a different cross-sectional view, needle carrier catch 235 contacts carrier release surface 203 and is tensioned towards needle carrier 234 causing carrier catch 235 to disengage from button catch surface 240. As carrier catch 235 disengages from button catch surface 240, sensor deployment assembly 236 is positioned within sensor housing 206 and deployment body catch 238 engages base catch surface 242. FIG. 53C is the same cross-sectional view as in FIG. 53B. FIG. 53C shows needle carrier 234 at an upper end of deployment button 204 and being pushed to that position by spring 232 as spring 232 expands from its tensioned position to a relaxed position when needle carrier catch 235 is released from carrier release surface 203. FIG. 53D shows still a different cross-sectional view of inserter assembly 200, 200' where resilient locking mechanism 205 of housing body 202 is pushed outwardly away from sensor housing 206, 206', 206" by protrusion 205a releasing catch surface 206a, which occurs when deployment button 204 arrives at the second, locked position. This effectively releases the inserter assembly 200, 200' from sensor housing 206, 206', 206" caused by release surface 204a of the deployment button 204 engaging the locking mechanism 205', 205 of the housing body 202. It should be appreciated that, when a user performs this single action after placement on the skin of the patient, the substantially simultaneous occurrence of the locking and releasing of the various catch surface produces a single, audible sound such as, for example, a click, as well as providing a single sensory vibration in the inserter assembly. The audible sound and the sensory vibration also occur substantially simultaneously. This alerts the user that the needle 100 has implanted sensor 120, that the needle 100 has already retracted into the inserter assembly 200, 200', that the inserter assembly 200, 200' has been released from sensor housing 206, 206', 206", and the sensor housing with the sensor 120 remains on the skin of the patient where the sensor housing is ready for receiving the electronic module 300, 700 if it was not already coupled to the sensor housing.

As stated previously, the inserter assembly design incorporates a further useful feature of the present invention, which is the safe retraction of the sharp for safe disposal. A sharp is defined by the FDA (the US Food and Drug Administration) as a device with sharp edges that can puncture or cut skin, and includes devices such as needles, syringes, infusion sets and lancets. Improper disposal or handling of sharps can cause accidental needle stick injuries including transmission of Hepatitis B (HBV), Hepatitis C (HBC) and Human Immunodeficiency Virus (HIV). Used sharps must be placed in a "sharps" container such as the BD™ Home Sharps Container, and fully sealed, before checking with local laws on proper disposal.

The mechanism shown in FIGS. 12 and 33 show the sharp fully retracted into the housing. The sharp is fully covered and is not accessible by finger. By design, the device cannot be made to re-deploy the sharp. No special "sharps" container is required to store and dispose of the housing body after sensor deployment. The entire body can be disposed of according to local laws.

Referring now to FIG. 54, a flow chart illustrates exemplary steps of a method 500' for continuous analyte measurement such as, for example, glucose with or without optional periodic medication delivery. To start, at step 502 select one of an inserter assembly 200, 200', 200" that contains either a sensor deployment assembly 236 with a sensor 120 and without a lumen 900 at step 503 or a sensor deployment assembly 236 with a sensor 120 and a lumen 900 at step 504. At step 505, select an inserter assembly 200, 200', 200" having either a sensor housing 206, 206', 206" unassembled with an electronic module 300, 300' or a sensor housing 206, 206' pre-assembled with an electronic module 300, 300'. At step 510, optionally place a sensor housing adhesive pad 600 configured for use with sensor housing 206, 206', 206" onto the bottom of the sensor housing. It is contemplated that adhesive pad 600 may already be attached to the inserter assembly where the user simply remove a backing for attaching the inserter assembly to a user's skin. It is further contemplated that other modes of adhesively securing the sensor housing 206' to the patient may be used, all as is well known in the art.

At step 520, inserter assembly 200' is placed on the insertion site of the patient with sensor housing 206' and, if optionally attached, sensor housing adhesive pad 600 contacting the patient's skin. In one embodiment, the area of contact is quite small, measuring about 1 inch (25.4 mm) wide by about 1.5 inches (38.1 mm) long. In one embodiment, step 520 includes fixing inserter assembly 200, 200', 200" to the skin using medical grade adhesive tape or the like.

At step 525, the user manually presses button 204 down to its second position (down position) to drive the low-force needle/sharp 100, continuous monitoring sensor 120 and optional lumen 900, as the case may be. Typically, the needle/sharp 100 is inserted about 8 mm into the subcutaneous tissue. Step 525 has been shown to take about 0.1 lbs. of force and be virtually painless to the patient.

At step 530, deployment mechanism 208 "bottoms out" or reaches its furthest downward position towards sensor housing 206, 206', 206". An audible "click" along with a sensory vibration alerts the user. At step 535, the audible click and the sensory vibration indicates to the user that the sensor 120 has been implanted, needle/sharp 100 has retracted back into inserter assembly 200, and inserter assembly 200 has released from sensor housing 206, 206', 206".

During step 535, deployment mechanism 208 automatically retracts or moves from the second carrier position (down position) to a third carrier position (up position), leaving continuous monitoring sensor 120 and optional lumen 900 inserted about 7 mm from the surface of the skin. Needle/sharp 100 is released by the double acting deployment mechanism 208 that quickly retracts needle/sharp 100 and sharp carrier 234.

At step 540, housing body 202, deployment button 204, and deployment mechanism 208 (also collectively referred to as the inserter assembly 200) are removed from sensor housing 206, 206', 206" without requiring any further action to be performed to cause the inserter assembly 200 to release from the sensor housing. As previously described, release of inserter assembly 200 from the sensor housing occurs automatically as deployment button 204 "bottoms out" and causes the release of locking mechanism 205 (e.g., pressing a snap feature) on housing body 202 away from sensor housing 206, 206', 206". The sensor housing is left on the patient. It is noted that manually pressing button 204 down to its second position (down position), which simultaneously moves deployment mechanism 208 and sensor deployment assembly 236, causes movement of deployment button 204, deployment mechanism 208 and sensor deployment assembly 236 to occur in the same linear and parallel direction.

If the inserter assembly 200 selected at step 505 was one pre-assembled with the electronic module, then electronic module 300, 300' is turned on at step 550 by any number of possible mechanisms such as, for example, a switch or removal of a non-electrically conducting substrate between electrical contacts, and the like. If the selected inserter assembly 200 was one without a lumen 900 at step 556, then the install in complete at step 565. If, however, the selected inserter assembly 200 was one with a lumen 900, then the medication delivery assembly 400, 400' is attached to the sensor housing, which then completes the install at step 565.

If the inserter assembly 200 selected at step 505 was an un-assembled with the electronic module, then the electronic module 300, 300' is installed in the sensor housing 206, 206', 206" at step 545. If the selected inserter assembly 200 was one without a lumen 900 at step 556, then the install in complete at step 565. If, however, the selected inserter assembly 200 was one with a lumen 900, then the medication delivery assembly 400, 400' is attached to the sensor housing, which then completes the install at step 565. It is understood that the medication delivery assembly 400, 400' is releasably connected to the needle bore 272 of sensor deployment assembly 236 creating a water-tight seal with a sealing member 412 between a delivery bore 408 and needle bore 272. Delivery tube 406 is connected between delivery bore 408 and a medication delivery module that contains, for example, insulin when the sensor is a glucose sensor.

At step 565, the completed sensor housing assembly is now operational. Whether the electronic module 300, 300', 700 is turned on automatically when the electronic module is assembled to the sensor housing or is manually switched on, the electronic module begins receiving electrical signals generated by sensor 120. The electrical signals generated by sensor 120 that is implanted subcutaneously in a patient are directly related to the analyte concentration in the subcutaneous tissue. In the case of where a glucose sensor is used, the electrical signals generate by sensor assembly 135 are directly related to the glucose concentration in the subcutaneous tissue. Electronic module 300' contains the electronic and/or electrical components that allows for measuring and recording the analyte of interest, which in the case of continuous glucose monitoring, is glucose. The data obtained from sensor 120 may be stored in electronic circuitry of the electronic and/or electrical components in electronic module 300, 300', 700 for simultaneous or later displays and/or transmission of the generated data. The electronic module may also include an inductive charging capability so that the onboard battery source can be conveniently charged without removal from the sensor housing.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. An inserter assembly for implanting a sensor subcutaneously into a patient, the assembly comprising:
   a housing body having a first body end and a second body end;
   a deployment button at least partially disposed in and slidable within the housing body through the first body end, the deployment button being movable from a first position to a second locked position;
   a deployment mechanism slidably disposed within and with respect to the deployment button, the deployment mechanism being movable, within and with respect to the deployment button, between: a ready position, an insertion position, and a retracted position, and the deployment mechanism having a needle;

a sensor deployment assembly disposed within the housing body and removably mated with the deployment mechanism, the sensor deployment assembly having a needle bore in which the needle is disposed when the deployment mechanism is in the ready position, and a sensor partially disposed within the needle bore, wherein the deployment mechanism, the needle, and the sensor define a deployment axis, the sensor having an electrical contact portion wherein the electrical contact portion is bent perpendicularly relative to electrodes and the deployment axis; and a sensor housing disposed at and removably retained by the second body end of the housing body, the sensor housing having a bottom surface and defining a sensor opening therethrough that is aligned with the deployment axis, wherein movement of the deployment button from the first position to the second locked position causes the sensor to be implanted subcutaneously into the patient along the deployment axis, the needle of the deployment mechanism to retract to the retracted position, the sensor deployment assembly to be fixed within the sensor housing, and the housing body, the deployment button and the deployment mechanism to release from the sensor housing.

2. The apparatus of claim 1, wherein the sensor deployment assembly comprises:

a sensor deployment body with a sensor deployment locking mechanism configured to engage the sensor housing when the button is moved to the second locked position, thereby locking the sensor deployment assembly with the sensor housing;

a sensor deployment guide attached to the sensor deployment body and positioned to abut the sensor housing to stop travel of the sensor deployment assembly when the deployment button is moved to the second locked position;

a sensor carrier attached to the sensor deployment guide and securing the sensor, the sensor carrier having a board-receiving face on a top sensor carrier surface and extending transversely to the deployment axis; and a sensor board mated with the board-receiving face and having a plurality of electronic coupling pads positioned for being electrically coupled to measuring electronics, wherein the sensor extends through the sensor bore and along the sensor board with the electrical contact portion of the sensor electrically coupled to the plurality of electronic coupling pads.

3. The apparatus of claim 1, wherein the deployment axis is substantially perpendicular to the bottom surface of the sensor housing.

4. The apparatus of claim 1, wherein the bottom surface of the sensor housing is configured to contact the patient during implantation of the sensor.

5. The apparatus of claim 1, wherein the sensor implanted subcutaneously in the patient has a working electrode of an electrode system on the sensor extending into the patient by about 4 mm to about 7 mm.

6. The apparatus of claim 1, wherein the sensor implanted subcutaneously in the patient has a working electrode of an electrode system on the sensor extending into the patient by about 2 mm to about 10 mm.

7. The apparatus of claim 2, wherein the sensor deployment locking mechanism comprises one or more resilient deployment catch on the sensor deployment assembly biased to engage a deployment catch surface on the sensor housing.

8. The apparatus of claim 1 further comprising:

a resilient button catch on one of the housing body or the sensor housing, the button catch biased to engage a button catch surface on the other of the housing body or the sensor housing when the deployment button is in the second locked position;

a resilient needle-carrier catch on one of the deployment button or the needle carrier, the needle-carrier catch biased to disengage a second catch surface on the other of the deployment button or the needle carrier when the deployment button is moved to the second locked position; and a resilient housing catch on one of the housing body or the sensor housing, the housing catch biased to disengage a housing catch surface on the other of the housing body or the sensor housing when the button is moved to the second locked position.

9. The apparatus of claim 1, wherein the movement of the deployment button from the first position to the second locked position is a single movement causing substantially at the same time the sensor to be implanted subcutaneously into the patient along the deployment axis, the needle of the deployment mechanism to retract to the retracted position, the sensor deployment assembly to be fixed within the sensor housing, and the housing body, the deployment button and the deployment mechanism to release from the sensor housing.

* * * * *